United States Patent
Estell et al.

(10) Patent No.: US 7,332,320 B2
(45) Date of Patent: Feb. 19, 2008

(54) PROTEASE PRODUCING AN ALTERED IMMUNOGENIC RESPONSE AND METHODS OF MAKING AND USING THE SAME

(75) Inventors: David A Estell, San Mateo, CA (US); Fiona A. Harding, Santa Clara, CA (US)

(73) Assignee: Genencor International, Inc., Palo Alto, CA (US)

(*) Notice: Subject to any disclaimer, the term of this patent is extended or adjusted under 35 U.S.C. 154(b) by 158 days.

(21) Appl. No.: 10/498,714

(22) PCT Filed: Dec. 20, 2002

(86) PCT No.: PCT/US02/41235

§ 371 (c)(1),
(2), (4) Date: Jun. 14, 2004

(87) PCT Pub. No.: WO03/057713

PCT Pub. Date: Jul. 17, 2003

(65) Prior Publication Data
US 2005/0148059 A1    Jul. 7, 2005

Related U.S. Application Data

(60) Provisional application No. 60/344,702, filed on Dec. 31, 2001.

(51) Int. Cl.
| C12N 9/54 | (2006.01) |
| C12N 15/57 | (2006.01) |
| C12N 15/74 | (2006.01) |
| A61K 8/66 | (2006.01) |
| C11D 3/386 | (2006.01) |

(52) U.S. Cl. .............. 435/219; 435/69.1; 435/220; 435/221; 435/222; 435/252.3; 435/320.1; 536/23.2; 424/401; 510/300

(58) Field of Classification Search .......... None
See application file for complete search history.

(56) References Cited

U.S. PATENT DOCUMENTS 3,755,560 A    8/1973    Dickert et al. ............ 424/78

(Continued)

FOREIGN PATENT DOCUMENTS

EP    134 267 B1    8/1989

(Continued)

OTHER PUBLICATIONS

Achstetter et al., "New Proteolytic Enzymes in Yeast," *Archives of Biochemistry and Biophysics*, 207(2):445-454 (1981).

(Continued)

*Primary Examiner*—Nashaat T. Nashed
*Assistant Examiner*—William W. Moore
(74) *Attorney, Agent, or Firm*—Kamrin T. MacKnight

(57) ABSTRACT

The present invention provides novel protein variants that exhibit reduced immunogenic responses, as compared to the parental proteins. The present invention further provides DNA molecules that encode novel variants, host cells comprising DNA encoding novel variants, as well as methods for making proteins less allergenic. In addition, the present invention provides various compositions that comprise these proteins that are less immunogenic than the wild-type proteins.

18 Claims, 7 Drawing Sheets

U.S. PATENT DOCUMENTS

| | | | |
|---|---|---|---|
| 3,929,678 A | 12/1975 | Laughlin et al. | 252/526 |
| 4,076,663 A | 2/1978 | Masuda et al. | 260/17.4 GC |
| 4,152,416 A | 5/1979 | Spitzer et al. | 424/46 |
| 4,261,868 A | 4/1981 | Hora et al. | 252/529 |
| 4,387,089 A | 6/1983 | De Polo | 424/59 |
| 4,404,128 A | 9/1983 | Anderson | 252/546 |
| 4,421,769 A | 12/1983 | Dixon et al. | 424/358 |
| 4,486,553 A | 12/1984 | Wesch | 523/179 |
| 4,533,359 A | 8/1985 | Kondo et al. | 8/128 R |
| 4,663,157 A | 5/1987 | Brock | 424/59 |
| 4,760,025 A | 7/1988 | Estell et al. | 435/222 |
| 4,937,370 A | 6/1990 | Sabatelli | 560/45 |
| 4,999,186 A | 3/1991 | Sabatelli et al. | 424/60 |
| 5,073,371 A | 12/1991 | Turner et al. | 424/401 |
| 5,073,372 A | 12/1991 | Turner et al. | 424/401 |
| 5,087,372 A | 2/1992 | Toyomoto et al. | 210/651 |
| 5,182,204 A | 1/1993 | Estell et al. | 435/222 |
| 5,185,258 A | 2/1993 | Caldwell et al. | 435/220 |
| 5,204,015 A | 4/1993 | Caldwell et al. | 252/174.12 |
| 5,352,603 A * | 10/1994 | Vetter et al. | 435/222 |
| 5,453,372 A * | 9/1995 | Vetter et al. | 435/222 |
| 5,482,849 A * | 1/1996 | Branner et al. | 435/222 |
| 5,631,217 A * | 5/1997 | Branner et al. | 510/320 |
| 5,665,587 A * | 9/1997 | Aaslyng et al. | 435/221 |
| 5,700,676 A * | 12/1997 | Bott et al. | 435/221 |
| 5,741,694 A * | 4/1998 | Hastrup et al. | 435/222 |
| 5,766,898 A | 6/1998 | Loevborg | 435/172.3 |
| 5,935,556 A | 8/1999 | Tanner et al. | 424/59 |
| 5,968,485 A | 10/1999 | Robinson | 424/59 |
| 5,972,316 A | 10/1999 | Robinson | 424/59 |
| 6,054,427 A * | 4/2000 | Winslow | 514/6 |
| 6,197,567 B1 * | 3/2001 | Aaslyng et al. | 435/221 |
| 6,300,116 B1 * | 10/2001 | von der Osten et al. | 435/220 |
| 6,303,119 B1 | 10/2001 | Weisgerber et al. | 424/94.63 |
| 6,428,799 B1 * | 8/2002 | Cen et al. | 424/402 |
| 6,541,234 B1 | 4/2003 | Bryan | 435/221 |
| 6,555,660 B2 * | 4/2003 | Nissen et al. | 530/397 |
| 6,569,663 B1 * | 5/2003 | Rubingh et al. | 435/221 |
| 6,586,221 B2 * | 7/2003 | Graycar et al. | 435/219 |
| 6,586,223 B1 | 7/2003 | Sikorski et al. | 435/220 |
| 6,605,458 B1 * | 8/2003 | Hansen et al. | 435/220 |
| 6,642,011 B2 | 11/2003 | Estell | 435/7.24 |
| 6,686,164 B1 * | 2/2004 | Olsen et al. | 435/7.1 |
| 6,946,128 B1 * | 9/2005 | Rubingh et al. | 424/94.64 |

FOREIGN PATENT DOCUMENTS

| | | |
|---|---|---|
| EP | 0 130 756 B1 | 2/1991 |
| EP | 0 251 446 B1 | 12/1994 |
| EP | 0 328 229 B2 | 10/1996 |
| EP | 0 680 745 B1 | 11/2002 |
| WO | WO 89/06279 | 7/1989 |
| WO | WO 92/10755 | 6/1992 |
| WO | WO 94/10191 | 5/1994 |
| WO | WO 95/34280 | 12/1995 |
| WO | WO 96/03964 | 2/1996 |
| WO | WO 96/16636 | 6/1996 |
| WO | WO 96/17929 | 6/1996 |
| WO | WO 96/40791 | 12/1996 |
| WO | WO 97/30148 | 8/1997 |
| WO | WO 98/22085 | 5/1998 |
| WO | WO 99/49056 | 9/1999 |
| WO | WO 00/24372 | 5/2000 |
| WO | WO 01/07578 | 2/2001 |
| WO | WO 00/06110 | 2/2002 |

OTHER PUBLICATIONS

Altschul et al., "Basic Local Alignment Search Tool," J. Mol. Biol., vol. 215, pp. 403-410, 1990.

Cosgrove et al., "Mice Lacking MHC Class II Molecules," Cell, 66:1051-1966 (1991).

CTFA International Cosmetic Ingredient Dictionary, 6th Edition, 1995, pp. 1026-1028 and 1103.

DelMar et al., "A Sensitive New Substrate For Chymotrypsin," Analytical Biochemistry, 99:316-320 (1979).

Giver et al., "Directed evolution of a thermostable esterase," Proc. Natl. Acad. Sci. USA, 95:2809-12813 (1998).

Grusby, Micheal J. et al., "Mice lacking major histocompatibility complex class I and class II molecules," Proc. Natl. Acad. USA, 90:3913-3917 (1993).

Harayami, Shigeaki, "Artificial evolution by DNA shuffling," Trends Biotechnol., 16:76-81 (1998).

Henikoff et al., "Amino acid substitution matrices from protein blocks," Proc. Natl. Acad. Sci. USA, 89:10915-10919 (1992).

Herman et al., "Determination of Glutamic Acid Decarboxylase 65 Peptides Presented by the Type I Diabetes-Associated HLA-DQ8 Class II Molecule Identifies an Immunogenic Peptide Motif," J. Immunol., 163:6275-6282 (1999).

Karlin, et al., "Applications and statistics for multiple high-scoring segments in molecular sequences," Proc. Natl. Acad. Sci. USA, 90:5873-5877 (1993).

Keifer et al. "Identification of a Second Human Subtilisin-Like Protease Gene in the fes/fps Region of Chromosome 15,"DNA and Cell Biology, 10(10)757-769 (1991).

Kuchner et al., "Directed evolution of enzyme catalysts," Trends Biotechnol., 15:523-530 (1997).

Lin et al., "Functional Expression of Horseradish Peroxidase in E. coli by Directed Evolution," Biotechnol. Prog., 15:467-471 (1999).

Research Disclosure No. 216034, (Research Disclosure Journal No. 21634), "Enzymatic silk degumming," (1982).

Moore et al., "Strategies for the in vitro Evolution of Protein Function: Enzyme Evolution by Random Recombination of Improved Sequences," J. Mol. Biol., 272:336-347 (1997).

Needleman et al., "A General Method Applicable to the Search for Similarities in the Amino Acid Sequence of Two Proteins," J. Mol. Biol., 48:443-453 (1970).

Patten et al., "Applications of DNA shuffling to pharmaceuticals and vaccines," Current Opinion in Biotechnol., 8:724-733 (1997).

Pearson et al., "Improved tools for biological sequence comparison," Proc. Natl. Acad. Sci. USA, 85:2444-2448 (1988).

Roebroek et al., "Evolutionary conserved close linkage of the c-fes/fps proto-oncogene and genetic sequences encoding a receptor-like protein," The EMBO Journal, 5(9):2197-2202 (1986).

Sagarin, E., Cosmetics, Science & Technology, 2nd ed., vol. 1, pp. 32-43 (1972).

Sayre, Robert M., "Physical Sunscreens," J. Soc. Cosmet. Chem., 41(2):103-109 (1990).

Sediah et al., "Proteolytic Enzymes: Serine and Cystein Peptidases," Meth. Enzymol., 244:174-189 Academic Press (1994).

Smith et al., "Comparison of Biosequences," Adv. Appl. Math., 2:482-489 (1981).

Sønderstrup et al., "HLA class II transgenic mice: models of the human $CD4^+$ T-cell immune response," Immunol. Rev., 172:335-343 (1999).

Stemmer, Willem P.C., "DNA shuffling by random fragmentation and reassembly: In vitro recombination for molecular evolution," Proc. Natl. Acad. Sci., USA, 91:10747-10751 (1994).

Stickler et al., "$CD4^+$T-cell Epitope Determination Using Unexposed Human Donor Peripheral Blood Mononuclear Cells," J. of Immunotherapy, 23(6):654-660 (2000).

Sun, Fengzhu, "Modeling DNA Shuffling," J. of Computational Biol., 6(1):77-90 (1999).

Taneja et al., "HLA class II transgenic mice as models of human diseases," Immunol Rev., 169:67-79 (1999).

Taurog et al., "Inflammatory disease in HLA-B27 transgenic rats," Immunol. Rev., 169:209-223 (1999).

Tomkinson et al., "Characterization of cDNA for Human Tripeptidyl Peptidase II: The N-Terminal Part of the Enzyme is Similar to Subtilisin," Biochem., 30(1):168-174 (1991).

Zhao et al., "Molecular evolution by staggered extension process (StEP) in vitro recombination," Nature Biotechnology, 16:258-261 (1998).

* cited by examiner

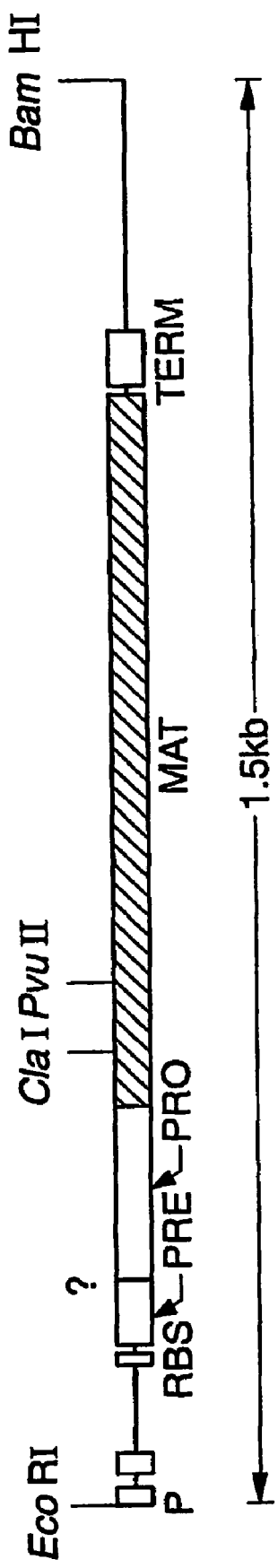
FIG._1A

| Pos | Sequence (aa / codon) |
|---|---|
| 549 | Ala GCA · Gly GGC · Gly GGA · Ala GCC · Ser AGC · 50 Met ATG · Val GTT · Pro CCT · Ser TCT · Glu GAA · Thr ACA · Asn AAT · Pro CCT · Phe TTC · Gln CAA · 60 Asp GAC · Asn AAC · Ser TCT · His CAC · Gly GGA · Thr ACT · His CAC · Val GTT · Ala GCC |
| 624 | 70 Gly GGC · Thr ACA · Val GTT · Ala GCT · Ala GCT · Leu CTT · Asn AAT · Asn AAC · 80 Asn AAC · Ala GCT · Pro CCA · Ser AGC · Ala GCA · Ser TCA · 90 Ala GCA · Leu CTT · Tyr TAC · Ala GCT · Val GTA · Lys AAA |
| 699 | Val GTT · Leu CTC · Gly GGT · Asp GAC · Ala GCT · Ser TCC · Gly GGT · Gln CAA · Tyr TAC · Ser AGC · 100 Gly GGT · Val GTT · Leu TTA · Gly GGC · Ile ATT · Ile ATC · Ala GCG · Asn AAC · 110 Met ATG · Ser AGC · Leu CTC · Gly GGC · Gly GGA · Pro CCA · Ser AGC · Ala GCA · Asn AAT · Met ATG |
| 774 | Asp GAC · Val GTT · Ile ATT · Asn AAC · Met ATG · Ser AGC · Leu CTC · Gly GGA · 120 Pro CCT · Ser TCT · Gly GGC · Gly GGA · Ala GCC · Ala GCA · Leu TTA · Lys AAA · 130 Ala GCG · Val GTT · Ala GCA |
| 849 | Ser TCC · Gly GGC · Val GTC · Val GTA · Val GTT · Val GTG · Ala GCA · Ala GCG · 140 Ala GCG · Val GTT · Ala GCA · Ala GCG · Leu GCT · Lys AAA · Ala GCC · Val GTT |
| 924 | 150 Ile ATT · Ser TCT · Gly GGT · Ala GCG · Ala GCA · Ser AGC · Thr ACT · Ser AGC · 160 Gly GGC · Thr ACA · Val GTG |
| 999 | 170 Lys AAA · Tyr TAC · Pro CCT · Asp GAT · Val GTC · Met ATG · Ala GCA · Pro CCT · 180 Val GTT · Ala GCT · Gly GGT · Asn AAC · Glu GAA · Gln CAA · Ser AGC · Asn AAC · Asp GAC · Ser AGC · Ser AGC · Thr ACA · 190 Ser AGC · Ser AGC · Ser AGC · Ser AGC · Thr ACA · Val GTG · Gly GGC · Tyr TAC · Pro CCT · Gly GGT |
| 1074 | 200 Ala GCA · Pro CCT · Gly GGC · Val GTA · Ile ATC · Gln CAA · Ser TCT · Thr ACG · Leu CTT · 210 Pro CCT · Gly GGA · Asn AAC · Arg AGA · Ala GCA · Gln CAA · Ser AGC · Val GTA · Tyr TAC · Ser AGC · Thr ACA · Ala GCG · Tyr TAC · Pro CCG · Gly GGT · 220 Thr ACG · Ser TCA · Met ATG · Ala GCA · Ser TCT · Pro CCG · His CAC · Val GTT · 230 Ala GCT · Gly GGA · Ala GCG · Ala GCT · Ala GCA · Leu TTG · Ile ATT · Leu CTT · Ser TCT · Lys AAG · His CAC · 240 Pro CCG · Asn AAC · Trp TGG · Thr ACA · Asn AAC · Thr ACT |

```
        Gln Val Arg Ser Ser Leu Glu Asn Thr Thr Lys Leu Gly Asp Ser Phe Tyr Tyr Gly Lys Gly Leu Ile Asn
                          250         Gln                              260                                
1149    CAA GTC CGC AGC AGT TTA GAA AAC ACC ACT ACA AAA CTT GGT GAT TCT TTC TAC TAT GGA AAA GGG CTG ATC AAC

Val Gln Ala Ala Ala Gln   oc                                TERM
           270                275
1224    GTA CAG GCG GCA GCT CAG TAA AACATAAAAAAACGGGCCTTGGCCCCGCCGGTTTTTATTTTCTTCCTCCGCATGTTCAATCCGCTCC

1316    ATAATCGACGGATGCTCCCTCTGAAAATTTTAACGAGAAACGGGGTTGACCCGGCTCAGTCCGGTAACGGCCAAGTCCTGAAACGTCTCAATCGCCG

1416    CTTCCCGGTTTCCGGTCAGCTCAATGCCGTAACGGTCGGCGGGCGTTTCCTGATACCGGGAGACGGCATTCGTAATCGGATC
```

*FIG._1B - 3*

| FIG._1B-1 |
|---|
| FIG._1B-2 |
| FIG._1B-3 |

*FIG._1B*

| | | | | | | | | | | | | | | |
|---|---|---|---|---|---|---|---|---|---|---|---|---|---|---|
|Ala|Gln|Ser|Val|Pro|Tyr|Gly|Val|Ser|Gln|Ile|Lys|Ala|Pro|Ala|15|
|Leu|His|Ser|Gln|Gly|Tyr|Thr|Gly|Ser|Asn|Val|Lys|Val|Ala|Val|30|
|Ile|Asp|Ser|Gly|Ile|Asp|Ser|Ser|His|Pro|Asp|Leu|Lys|Val|Ala|45|
|Gly|Gly|Ala|Ser|Met|Val|Pro|Ser|Glu|Thr|Asn|Pro|Phe|Gln|Asp|60|
|Asn|Asn|Ser|His|Gly|Thr|His|Val|Ala|Gly|Thr|Val|Ala|Ala|Leu|75|
|Asn|Asn|Ser|Ile|Gly|Val|Leu|Gly|Val|Ala|Pro|Ser|Ala|Ser|Leu|90|
|Try|Ala|Val|Lys|Val|Leu|Gly|Ala|Asp|Gly|Ser|Gly|Gln|Tyr|Ser|105|
|Trp|Ile|Ile|Asn|Gly|Ile|Glu|Trp|Ala|Ile|Ala|Asn|Asn|Met|Asp|120|
|Val|Ile|Asn|Met|Ser|Leu|Gly|Gly|Pro|Ser|Gly|Ser|Ala|Ala|Leu|135|
|Lys|Ala|Ala|Val|Asp|Lys|Ala|Val|Ala|Ser|Gly|Val|Val|Val|Val|150|
|Ala|Ala|Ala|Gly|Asn|Glu|Gly|Thr|Ser|Gly|Ser|Ser|Ser|Thr|Val|165|
|Gly|Tyr|Pro|Gly|Lys|Tyr|Pro|Ser|Val|Ile|Ala|Val|Gly|Ala|Val|180|
|Asp|Ser|Ser|Asn|Gln|Arg|Ala|Ser|Phe|Ser|Ser|Val|Gly|Pro|Glu|195|
|Leu|Asp|Val|Met|Ala|Pro|Gly|Val|Ser|Ile|Gln|Ser|Thr|Leu|Pro|210|
|Gly|Asn|Lys|Tyr|Gly|Ala|Leu|Asn|Gly|Thr|Ser|Met|Ala|Ser|Pro|225|
|His|Val|Ala|Gly|Ala|Ala|Ala|Leu|Ile|Leu|Ser|Lys|His|Pro|Asn|240|
|Trp|Thr|Asn|Thr|Gln|Val|Arg|Ser|Ser|Leu|Glu|Asn|Thr|Thr|Thr|255|
|Lys|Leu|Gly|Asp|Ser|Phe|Tyr|Tyr|Gly|Lys|Gly|Leu|Ile|Asn|Val|270|
|Gln|Ala|Ala|Ala|Gln| | | | | | | | | | |275|

FIG._2

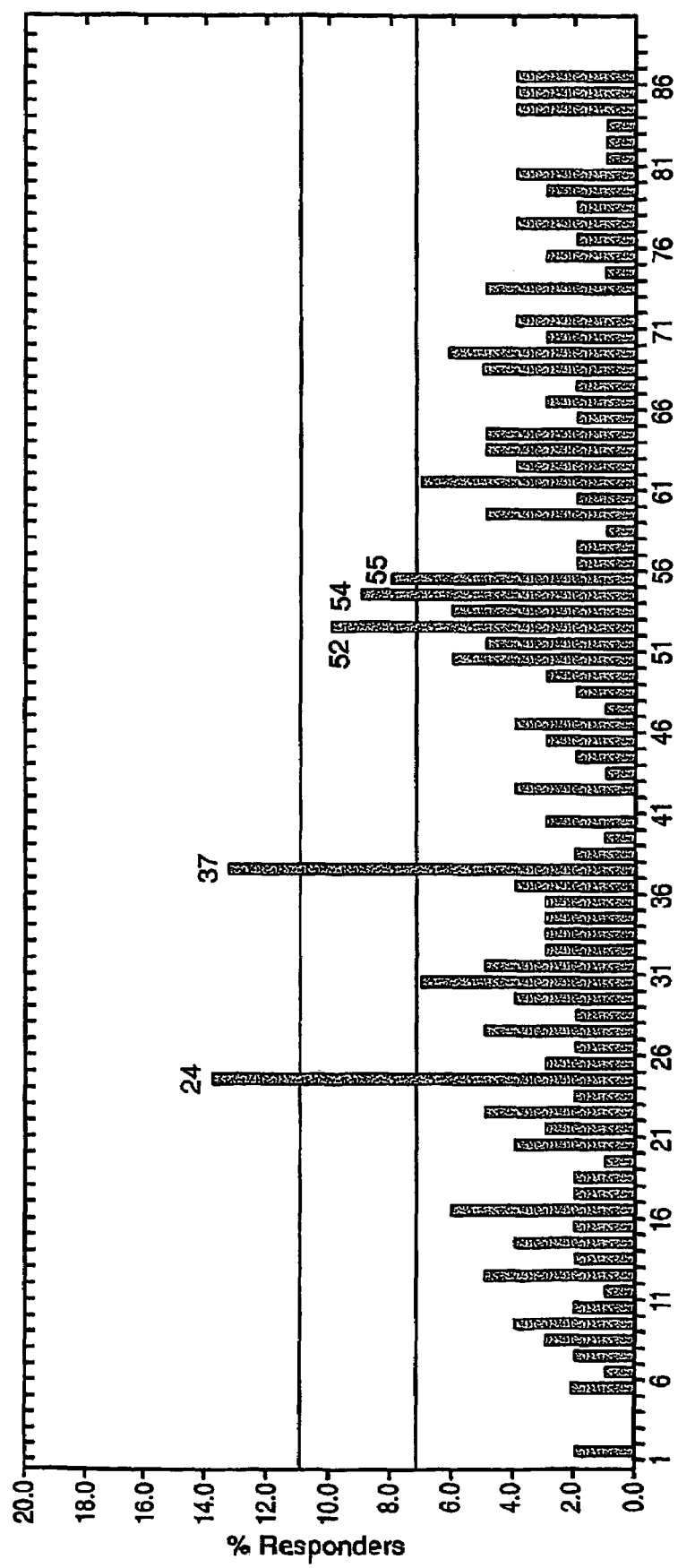
FIG._3

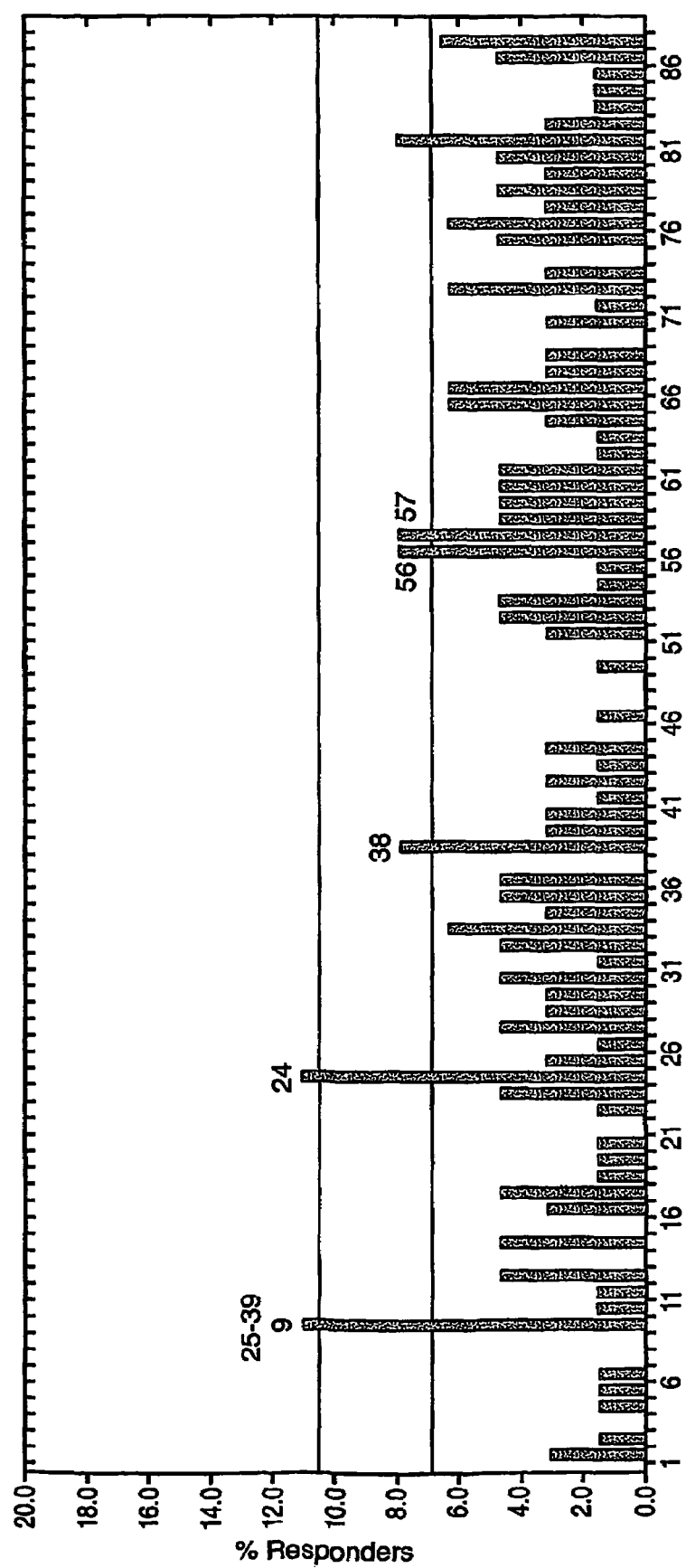
FIG._4

US 7,332,320 B2

PROTEASE PRODUCING AN ALTERED IMMUNOGENIC RESPONSE AND METHODS OF MAKING AND USING THE SAME

The present application claims priority to now abandoned U.S. Provisional Patent Application Ser. No. 60/344,702, filed Dec. 31, 2001. The present application is also a national stage filing under 35 U.S.C. § 371 of the PCT International application PCT/US02/41235, filed Dec. 20, 2002.

FIELD OF THE INVENTION

The present invention provides novel protein variants that exhibit reduced immunogenic responses, as compared to the parental proteins. The present invention further provides DNA molecules that encode novel variants, host cells comprising DNA encoding novel variants, as well as methods for making proteins less allergenic. In addition, the present invention provides various compositions that comprise these proteins that are less immunogenic than the wild-type proteins.

BACKGROUND OF THE INVENTION

Proteins used in industrial, pharmaceutical and commercial applications are of increasing prevalence and importance. However, this has resulted in the sensitization of numerous individuals to these proteins, resulting in the widespread occurrence of allergic reactions to these proteins. For example, some proteases are associated with hypersensitivity reactions in certain individuals. As a result, despite the usefulness of proteases in industry (e.g., in laundry detergents, cosmetics, textile treatment etc.), as well as the extensive research performed in the field to provide improved proteases (e.g., with more effective stain removal under typical laundry conditions), the use of proteases in industry has been problematic.

Much work has been done to alleviate these problems. Strategies explored to reduce immunogenic potential of protease use include improved production processes which reduce potential contact by controlling and minimizing workplace concentrations of dust particles and/or aerosol carrying airborne protease, improved granulation processes which reduce the amount of dust or aerosol actually produced from the protease product, and improved recovery processes to reduce the level of potentially allergenic contaminants in the final product. However, efforts to reduce the allergenicity of proteases themselves have been relatively unsuccessful. Alternatively, efforts have been made to mask epitopes in protease which are recognized by immunoglobulin E (IgE) in hypersensitive individuals (See, PCT Publication No. WO 92/10755), or to enlarge the nature of the antigenic determinants by attaching polymers or peptides/proteins to the problematic protease.

When an adaptive immune response occurs in an exaggerated or inappropriate form, the individual experiencing the reaction is said to be hypersensitive. Hypersensitivity reactions are the result of normally beneficial immune responses acting inappropriately and sometimes cause inflammatory reactions and tissue damage. Hypersensitivity can be provoked by any number of antigens and the reactions of individuals to these antigens also varies greatly. Hypersensitivity reactions do not normally occur upon the first contact of an individual with the antigen. Rather, these reactions occur upon subsequent exposure to the antigen. For example, one form of hypersensitivity occurs when an IgE response is directed against innocuous (i.e., non pathogenic) environmental antigens (e.g., pollen, dust mites, or animal dander). The resulting release of pharmacological mediators by IgE-sensitized mast cells produces an acute inflammatory reaction with symptoms such as asthma, rhinitis, or hayfever.

Unfortunately, strategies intended to modify IgE sites are generally not successful in preventing the cause of the initial sensitization reaction. Accordingly, such strategies, while sometimes neutralizing or reducing the severity of the subsequent hypersensitivity reaction, do not reduce the number of persons actually sensitized. For example, when a person is known to be hypersensitive to a certain antigen, the general manner of dealing with such a situation is to prevent any subsequent contact of the hypersensitive person to the antigen. Indeed, any other course of action could be dangerous to the health and/or life of the hypersensitive individual. Thus, while reducing the danger of a specific protein for a hypersensitive individual is important, for industrial purposes it is far more valuable to reduce or eliminate the capability of the protein to initiate the hypersensitivity reaction in the first place.

While some studies have provided methods of reducing the allergenicity of certain proteins and identification of epitopes which cause allergic reactions in some individuals, the assays used to identify these epitopes generally involve measurement of IgE and IgG in the sera of those who have been previously exposed to the antigen. However, once an Ig reaction has been initiated, sensitization has already occurred. Accordingly, there is a need to identify proteins which produce an enhanced immunologic response, as well as a need to produce proteins which produce a reduced immunologic response.

SUMMARY OF THE INVENTION

The present invention provides novel protein variants that exhibit reduced immunogenic responses, as compared to the parental proteins. The present invention further provides DNA molecules that encode novel variants, host cells comprising DNA encoding novel variants, as well as methods for making proteins less allergenic. In addition, the present invention provides various compositions that comprise these proteins that are less immunogenic than the wild-type proteins.

The present invention provides protease variants with useful activity in common protease applications (e.g., detergents, compositions to treat textiles in order to prevent felting, in bar or liquid soap applications, dish-care formulations, contact lens cleaning solutions and/or other optical products, peptide hydrolysis, waste treatment, cosmetic formulations, skin care). In addition, the present invention provides protease variants that find use as fusion-cleavage enzymes for protein production. In particularly preferred embodiments, these protease variants are more safe to use than the natural proteases, due to their decreased allergenic potential.

The present invention also provides proteases in which at least one T-cell epitope is modified so as to reduce or preferably neutralize (i.e., eliminate) the ability of the T-cell to identify that epitope. In some embodiments, the present invention provides proteases having reduced allergenicity, wherein the protease comprises a modification comprising the substitution or deletion of amino acid residues that are identified as being positioned within a T-cell epitope. In some preferred embodiments, the present invention provides means to identify epitopes of proteases that upon recognition by a T-cell, result in an increase in T-cell proliferation that is greater than the baseline level. In some particularly preferred embodiments, these identified T-cell epitopes are then modified such that when the peptide comprising the modified epitope is analyzed using the means provided by the present invention, there is a lower level of T-cell proliferation, as compared to the unmodified epitope. In some embodiments, the modified epitope results in T-cell proliferation that is greater than three times the baseline T-cell proliferation, while in some alternative embodiments, the modified epitopes produce a level of T-cell proliferation that is three times less than baseline T-cell proliferation. In other embodiments, the modified epitopes produce a level of T-cell proliferation that is less than twice that of the baseline T-cell proliferation. In still further embodiments, the modified epitopes produce a T-cell proliferation level that is less than or substantially equal to the baseline T-cell proliferation.

In some embodiments, the present invention provides means to modify epitopes. In some embodiments, the epitope is modified such that: (a) the amino acid sequence of the epitope is substituted with an analogous sequence from a human homolog to the protein of interest (i.e., human subtilisin or another human protease derived subtilisin like molecule such as furin or the kexins) (See e.g., Meth. Enzymol., 244:175 [1994]; Roebroek et al.; EMBO J., 5:2197-2202 [1986]; Tomkinson et al., Biochem., 30:168-174 [1991]; Keifer et al., DNA Cell. Biol., 10:757-769 (1991)); (b) the amino acid sequence of the epitope is substituted with an analogous sequence from a non-human homolog to the protein of interest, wherein the analogous sequence produces a lesser allergenic response due to T-cell recognition than that of the protein of interest; (c) the amino acid sequence of the epitope is substituted with a sequence which substantially mimics the major tertiary structure attributes of the epitope, but which produces a lesser allergenic response due to T-cell recognition than that of the protein of interest; (d) with any sequence which produces lesser allergenic response due to T-cell recognition than that of the protein of interest; or (e) the protein of interest is substituted with a homologous protein that already has analogous sequences for each epitope that produce lesser allergenic response due to T-cell recognition than that of the protein of interest.

In one embodiment of the present invention, protease variants are provided comprising at least one amino acid substitution at a position corresponding to identified epitopes regions comprising at one or more residues 25, 26, 27, 28, 29, 30, 31, 32, 33, 34, 35, 36, 37, 38, 39, 88, 89, 90, 91, 92, 93, 94, 95, 96, 97, 98, 99, 100, 101, 102, 154, 155, 156, 157, 158, 159, 160, 161, 162, 163, 164, 165, 166, 167, 168, 169, 170, 171, 172, 173, 174, 175, 176, 177, 181, 182, 183, 184, 185, 186, 187, 188, 189, 190, 191, 192, 193, 194, and 195 of *Bacillus amyloliquefaciens* subtilisin in BPN', as set forth in SEQ ID NO:2, wherein such substitutions comprise modifying the residue with a non-wild type amino acid (e.g., alanine, arginine, aspartic acid, asparagine, cysteine, glutamic acid, glutamine, glycine, histidine, isoleucine, leucine, lysine, methionene, phenylalanine, proline, serine, threonine, tryptophan, tyrosine and/or valine).

In other embodiments of the present invention, methods for producing proteins having reduced allergenicity are provided. In some preferred embodiments, a mutant protein is prepared by modifying DNA encoding a precursor protein, such that the modified DNA encodes the mutant protein of the present invention.

In yet other embodiments of the present invention, DNA sequences encoding the mutant protein, as well as expression vectors containing such DNA sequences and host cells transformed with such vectors are provided. In some particularly preferred embodiments, the host cells are capable of expressing such DNA to produce the mutant protein of the invention either intracellularly or extracellularly.

The present invention also provides mutant proteins that are useful in any composition or process in which the precursor protein is generally known to be useful. For example, in embodiments in which the protein is a protease, the reduced allergenicity protease is suitable for use as a component in cleaning products (e.g., laundry detergents and hard surface cleansers), as an aid in the preparation of leather, in the treatment of textiles such as wool and/or silk to reduce felting, as a component in a personal care, cosmetic and/or face cream product, and as a component in animal (e.g., livestock and companion animals) feed to improve the nutritional value of the feed. Similarly, in embodiments in which the protein is an amylase, the reduced allergenicity amylase finds use in the liquefaction of starch, as a component in a dishwashing and/or laundry detergent, and desizing of textiles, as well as any other suitable use for amylases.

In some preferred embodiments, the present invention provides methods that facilitate the identification of peptides which contain epitopes responsible for the initial sensitization of an individual. In further preferred embodiments, neutralization of such "sensitizing" T-cell epitopes results in a greater degree of safety for those who handle or are otherwise exposed to the antigen containing the epitope because they will not be initially sensitized, thus preventing the production of Ig antibodies typical of an allergic reaction upon subsequent exposure to the antigen.

In some particularly preferred embodiments, the present invention provides proteins (e.g., enzymes) that can be used with significantly less danger of sensitization for the individuals exposed. Thus, in some preferred embodiments, the proteins of the invention are more safely used in cosmetics (e.g., lotions, face creams, etc.), detergents (e.g., laundry and dishwashing detergents), hard surface cleaning compositions, and pre-wash compositions or any other use of protein, including enzymes, wherein human exposure is a necessary by-product.

The present invention provides variants of a protease of interest comprising at least one T-cell epitope, wherein the variant differs from the protease of interest by having an altered T-cell epitope such that the variant exhibits an altered immunogenic response from the protease of interest in a human; wherein the altered T-cell epitope of the protease of interest includes one or more amino acid substitutions at residues corresponding to 25, 26, 27, 28, 29, 30, 31, 32, 33, 34, 35, 36, 37, 38, 39, 88, 89, 90, 91, 92, 93, 94, 95, 96, 97, 98, 99, 100, 101, 102, 154, 155, 156, 157, 158, 159, 160, 161, 162, 163, 164, 165, 166, 167, 168, 169, 170, 171, 172, 173, 174, 175, 176, 177, 181, 182, 183, 184, 185, 186, 187, 188, 189, 190, 191, 192, 193, 194, and 195 of *Bacillus amyloliquefaciens* subtilisin, as set forth in SEQ ID NO:2. In some preferred embodiments, the immunogenic response produced by the variant is less than the immunogenic response produced by the protease of interest, while in alternative embodiments, the immunogenic response produced by the variant is greater than the immunogenic response produced by the protease of interest. In some embodiments, the immunogenic response produced by the variant is characterized by an in vivo reduction in allergenicity. In some preferred embodiments, immunogenic response produced by the variant is characterized by an in vitro reduction in allergenicity. In some embodiments, the present invention provides the nucleic acids encoding the variants. In further embodiments, the present invention provides host cells that comprise the nucleic acid encoding the variants of the present invention.

The present invention further provides cleaning compositions, personal care products (e.g., shampoos and body lotions), and other compositions comprising at least one of the variants. In some embodiments, the present invention provides skin care compositions comprising at least one variant of a protease of interest comprising a T-cell epitope, wherein the variant differs from the protease of interest by having an altered T-cell epitope such that the variant and the protease of interest produce different immunogenic responses in a human; wherein the T-cell epitope of the protease of interest includes one or more amino acid substitution selected from the group consisting of residues corresponding to 25, 26, 27, 28, 29, 30, 31, 32, 33, 34, 35, 36, 37, 38, 39, 88, 89, 90, 91, 92, 93, 94, 95, 96, 97, 98, 99, 100, 101, 102, 154, 155, 156, 157, 158, 159, 160, 161, 162, 163, 164, 165, 166, 167, 168, 169, 170, 171, 172, 173, 174, 175, 176, 177, 181, 182, 183, 184, 185, 186, 187, 188, 189, 190, 191, 192, 193, 194, and 195 of *Bacillus amyloliquefaciens* subtilisin, as set forth in SEQ ID NO:2. In some embodiments, the skin care composition further comprises a cosmetically acceptable carrier. In further embodiments, the carrier comprises a hydrophilic diluent selected from the group consisting of water, propylene glycol, ethanol, propanol, glycerol, butylene glycol, polyethylene glycol having a molecular weight from about 200 to about 600, polypropylene glycol having a molecular weight from about 425 to about 2025, and mixtures thereof. In additional embodiments, the skin care composition further comprises a skin care active. In some preferred embodiments, the skin care active is selected from the group consisting of Vitamin B3 component, panthenol, Vitamin E, Vitamin E acetate, retinol, retinyl propionate, retinyl palmitate, retinoic acid, Vitamin C, theobromine, alpha-hydroxyacid, farnesol, phytrantriol, salicylic acid, palmityl peptapeptide-3 and mixtures thereof. In some embodiments, the Vitamin B3 component is niacinamide. In some alternative embodiments, the skin care composition further comprises glycerine.

The present invention further provides skin care compositions comprising: from about 0.00001% to about 1%, by weight, of a variant of a protease of interest comprising a T-cell epitope, wherein the variant differs from the protease of interest by having an altered T-cell epitope such that the variant and the protease of interest produce different immunogenic responses in a human; wherein the T-cell epitope of the protease of interest includes an amino acid substitution at a residue corresponding to 25, 26, 27, 28, 29, 30, 31, 32, 33, 34, 35, 36, 37, 38, 39, 88, 89, 90, 91, 92, 93, 94, 95, 96, 97, 98, 99, 100, 101, 102, 154, 155, 156, 157, 158, 159, 160, 161, 162, 163, 164, 165, 166, 167, 168, 169, 170, 171, 172, 173, 174, 175, 176, 177, 181, 182, 183, 184, 185, 186, 187, 188, 189, 190, 191, 192, 193, 194, and 195 of *Bacillus amyloliquefaciens* subtilisin, as set forth in SEQ ID NO:2; from about 0.01% to about 20%, by weight, of a humectant; from about 0.1% to about 20%, by weight, of a skin care active; from about 0.05% to about 15%, by weight, of a surfactant; and from about 0.1% to about 20%, by weight, of silicone.

The present invention further provides cleaning compositions comprising at least one variant of a protease of interest comprising a T-cell epitope, wherein the variant differs from the protease of interest by having an altered T-cell epitope such that the variant and the protease of interest produce different immunogenic responses in a human; wherein the T-cell epitope of the protease of interest includes one or more amino acid substitution at a residue corresponding to 25, 26, 27, 28, 29, 30, 31, 32, 33, 34, 35, 36, 37, 38, 39, 88, 89, 90, 91, 92, 93, 94, 95, 96, 97, 98, 99, 100, 101, 102, 154, 155, 156, 157, 158, 159, 160, 161, 162, 163, 164, 165, 166, 167, 168, 169, 170, 171, 172, 173, 174, 175, 176, 177, 181, 182, 183, 184, 185, 186, 187, 188, 189, 190, 191, 192, 193, 194, and 195 of *Bacillus amyloliquefaciens* subtilisin, as set forth in SEQ ID NO:2.

BRIEF DESCRIPTION OF THE DRAWINGS

FIG. 1 (Panels A-C) provide the DNA (SEQ ID:NO 1) and amino acid (SEQ ID:NO 2) sequences of *B. amyloliquefaciens* subtilisin (BPN') and a partial restriction map of this gene.

FIG. 2 provides the amino acid sequence of the precursor protease P1 (BPN'-Y217L) (SEQ ID NO:3).

FIG. 3 provides a graph showing the percent responders to a protease of interest (P1) extract (n=100).

FIG. 4 provides a graph showing the percent responders to a protease of interest (P1).

DESCRIPTION OF THE INVENTION

The present invention provides novel protein variants that exhibit reduced immunogenic responses, as compared to the parental proteins. The present invention further provides DNA molecules that encode novel variants, host cells comprising DNA encoding novel variants, as well as methods for making proteins less allergenic. In addition, the present invention provides various compositions that comprise these proteins that are less immunogenic than the wild-type proteins.

Immune Response and Allergenicity

There are two major branches that comprise the acquired immune response. The first involves the production of antibodies by B-cells and plasma cells (i.e., humoral or antibody-mediated immunity), while the second involves the response of T-cells and the activation of various cytokines and other immune mediators (i.e., cell-mediated immunity). These two systems are inter-related and work in concert with the innate immune system.

The development of an antibody to a protein requires as series of events that begin with a peptide segment derived from that protein being presented on the surface of a professional (activated) antigen presenting cell (APC). The peptide is associated with a specific protein on the surface of the APC, namely a protein in the major histocompatibility complex (MHC) (in humans, the MHC is referred to as the "human leukocyte antigen" (HLA) system). The bound peptide is capable of interacting with T-cells. Specifically, the T-cell is of the subtype recognized by the expression of the CD4 protein on its surface (i.e., it is a CD4$^+$ T-cell). If the interaction is successful, the specific CD4$^+$ T-cell grows and divides (i.e., proliferates) and becomes capable of interacting with B-cells. If that interaction is successful, the B-cell proliferates and develops into a plasma cell, which is a center for the production of antibodies that are specifically directed against the original antigen. Thus the ultimate production of an antibody is dependent on the initial activation of a CD4$^+$ T-cell that is specific for a single peptide sequence (i.e., an epitope). Using the compositions and methods described herein, it is possible to predict which peptides within a target protein will be capable of the initial activation of specific CD4+ T-cells.

While T-cells and B-cells are both activated by immunogenic epitopes which exist on a given protein or peptide, the actual epitopes recognized by these cells are generally not identical. In fact, the epitope that activates a T-cell is often not the same epitope that is later recognized by B-cells that recognize the same protein or peptide (i.e., proteins and peptides generally have multiple epitopes). Thus, with respect to hypersensitivity, while the specific antigenic interaction between the T-cell and the antigen is a critical element in the initiation of the immune response, the specifics of that interaction (i.e., the epitope recognized), is often not relevant to subsequent development of a full blown allergic reaction mediated by IgE antibody.

Various means to reduce allergenicity of proteins have been reported. For example, PCT Publication No. WO 96/40791 describes a process for producing polyalkylene oxide-protease conjugates with reduced allergenicity using polyalkylene oxide as a starting material. PCT Publication No. WO 97/30148 describes a polypeptide conjugate with reduced allergenicity which comprises one polymeric carrier molecule to which two or more polypeptide molecules are covalently coupled. PCT Publication No. WO 96/17929 describes a process for producing polypeptides with reduced allergenicity comprising the step of conjugating from 1 to 30 polymolecules to a parent polypeptide.

PCT Publication No. WO 92/10755 describes a method of producing protein variants evoking a reduced immunogenic response in animals. In this publication, the proteins of interest, a series of proteases and variants thereof, were used to immunize rats. The sera from the rats were then used to measure the reactivity of the polyclonal antibodies present in these sera to the protein of interest and variants thereof. From these results, it was possible to determine whether the antibodies in the preparation were comparatively more or less reactive with the protein and its variants, thus permitting an analysis of which changes in the protein were likely to neutralize or reduce the ability of the Ig to bind. From these tests on rats, the conclusion was arrived at that changing any of subtilisin 309 residues corresponding to 127, 128, 129, 130, 131, 151, 136, 151, 152, 153, 154, 161, 162, 163, 167, 168, 169, 170, 171, 172, 173, 174, 175, 176, 186, 193, 194, 195, 196, 197, 247, 251, 261 would result in a change in the immunogenic potential of the enzyme.

PCT Publication No. WO 94/10191 describes low allergenic proteins comprising oligomeric forms of the parent monomeric protein, wherein the oligomer has substantially retained its activity. PCT Publication Nos. WO 99/49056 and WO 01/07578 describe a plurality of subtilisin variants having amino acid substitutions in a defined epitope region. However, due to the large number of variants disclosed, one of skill in the art is presented with a problem with respect to identifying an optimal protease product with reduced immunogenic potential suitable for use in personal care and/or other applications.

Definitions

To facilitate understanding the present invention, the following definitions are provided.

"Antigen presenting cell" ("APC"), as used herein, refers to a cell of the immune system that presents antigen on its surface, such that the antigen is recognizable by receptors on the surface of T-cells. Antigen presenting cells include, but are not limited to dendritic cells, interdigitating cells, activated B-cells and macrophages.

The terms "T lymphocyte" and "T-cell," as used herein encompass any cell within the T lymphocyte lineage from T-cell precursors (including Thy1 positive cells which have not rearranged the T cell receptor genes) to mature T cells (i.e., single positive for either CD4 or CD8, surface TCR positive cells).

The terms "B lymphocyte" and "B-cell" encompasses any cell within the B-cell lineage from B-cell precursors, such as pre-B-cells ($B220^+$ cells which have begun to rearrange Ig heavy chain genes), to mature B-cells and plasma cells.

As used herein, "$CD4^+$ T-cell" and "CD4 T-cell" refer to helper T-cells, while "$CD8^+$ T-cell" and CD8 T-cell" refer to cytotoxic T-cells.

"T-cell proliferation," as used herein, refers to the number of T-cells produced during the incubation of T-cells with the antigen presenting cells, with or without antigen.

"Baseline T-cell proliferation," as used herein, refers to the degree of T-cell proliferation that is normally seen in an individual in response to exposure to antigen presenting cells in the absence of peptide or protein antigen. For the purposes herein, the baseline T-cell proliferation level is determined on a per sample basis for each individual as the proliferation of T-cells in response to antigen presenting cells in the absence of antigen.

"T-cell epitope," as used herein, refers to a feature of a peptide or protein which is recognized by a T-cell receptor in the initiation of an immunogenic response to the peptide comprising that antigen (i.e., the immunogen). Although it is not intended that the present invention be limited to any particular mechanism, it is generally believed that recognition of a T-cell epitope by a T-cell is via a mechanism wherein T-cells recognize peptide fragments of antigens which are bound to Class I or Class II MHC (i.e., HLA) molecules expressed on antigen-presenting cells (See e.g., Moeller, Immunol. Rev., 98:187 [1987]).

"Altered T-cell epitope," as used herein, refers to an epitope amino acid sequence which differs from the precursor peptide or peptide of interest, such that the variant peptide of interest produces different immunogenic responses in a human or another animal. It is contemplated that an altered immunogenic response includes altered allergenicity, including either increased or decreased overall immunogenic response. In some embodiments, the altered T-cell epitope comprises substitution and/or deletion of an amino acid selected from those residues within the identified epitope. In alternative embodiments, the altered T-cell epitope comprises an addition of one or more residues within the epitope.

An "altered immunogenic response," as used herein, refers to an increased or reduced immunogenic response. Proteins (e.g., proteases) and peptides exhibit an "increased immunogenic response" when the T-cell response they evoke is greater than that evoked by a parental (e.g., precursor) protein or peptide (e.g., the protease of interest). The net result of this higher response is an increased antibody response directed against the variant protein or peptide. Proteins and peptides exhibit a "reduced immunogenic response" when the T-cell response they evoke is less than that evoked by a parental (e.g., precursor) protein or peptide. The net result of this lower response is a reduced antibody response directed against the variant protein or peptide. In some embodiments, the parental protein is a wild-type protein or peptide.

The term "sample" as used herein is used in its broadest sense. However, in preferred embodiments, the term is used in reference to a sample (e.g., an aliquot) that comprises a peptide protein" (e.g., protease) that is being analyzed, identified, and/or modified. Thus, in most cases, this term is used in reference to material that includes a protein or peptide that is of interest.

"Protease of interest," as used herein, refers to a protease which is being analyzed, identified and/or modified. In some preferred embodiments, the term is used in reference to proteases that exhibit the same immunogenic responses in assays as does the protease "BPN'" obtained from *B. amyloliquefaciens*. In other embodiments, the term is used in reference to proteases in which it is desirous to alter the immunogenic response thereto. As used herein, the phrase the "same immunogenic response in assays as does the protease from *B. amyloliquefaciens*" means that the protease of interest responds to one or more of the same epitopic regions as *B. amyloliquefaciens* BPN' protease, as described herein and tested using various in vivo and/or in vitro assays.

As used herein, "protease" refers to naturally-occurring proteases, as well as recombinant proteases. Proteases are carbonyl hydrolases which generally act to cleave peptide bonds of proteins or peptides. Naturally-occurring proteases include, but are not limited to such examples as α-aminoacylpeptide hydrolase, peptidylamino acid hydrolase, acylamino hydrolase, serine carboxypeptidase, metallocarboxypeptidase, thiolproteinase, carboxylproteinase and metalloproteinase. Serine, metallo, thiol and acid proteases are included, as well as endo and exo-proteases.

As used herein, "subtilisin" refers to a naturally-occurring subtilisin or a recombinant subtilisin. Subtilisins are bacterial or fungal proteases which generally act to cleave peptide bonds of proteins or peptides.

"Recombinant," "recombinant subtilisin" and "recombinant protease" refer to a subtilisin or protease in which the DNA sequence encoding the subtilisin or protease is modified to produce a variant (or mutant) DNA sequence which encodes the substitution, deletion or insertion of one or more amino acids in the naturally-occurring amino acid sequence. Suitable methods to produce such modification, and which may be combined with those disclosed herein, include those disclosed in U.S. Pat. No. 4,760,025 (U.S. RE 34,606), U.S. Pat. No. 5,204,015 and U.S. Pat. No. 5,185,258, all of which are incorporated herein by reference.

"Non-human subtilisins" and the DNA sequences encoding them are obtained from many prokaryotic and eukaryotic organisms. Suitable examples of prokaryotic organisms include Gram-negative organisms (e.g., *E. coli* and *Pseudomonas* sp.), as well as Gram-positive bacteria (e.g., *Micrococcus* sp. and *Bacillus* sp.). Examples of eukaryotic organisms from which subtilisins and their genes may be obtained include fungi such as *Saccharomyces cerevisiae* and *Aspergillus* sp.

"Human subtilisin," as used herein, refers to proteins of human origin which have subtilisin type catalytic activity (e.g., the kexin family of human-derived proteases). Additionally, derivatives or homologs of proteins provided herein, including those from non-human sources (e.g., mice and rabbits), which retain the essential activity of the peptide, such as the ability to hydrolyze peptide bonds and exhibits the altered immunogenic response as described elsewhere in this application, etc., have at least 50%, at least 65% and preferably at least 80%, more preferably at least 90%, and sometimes as much as 95%, 97%, or even 99% homology to the protease of interest. The essential activity of the homolog includes the ability to produce different immunogenic responses in a human. In one embodiment, the protease of interest is shown in the FIG. 4*a*.

Figure 1B-1:
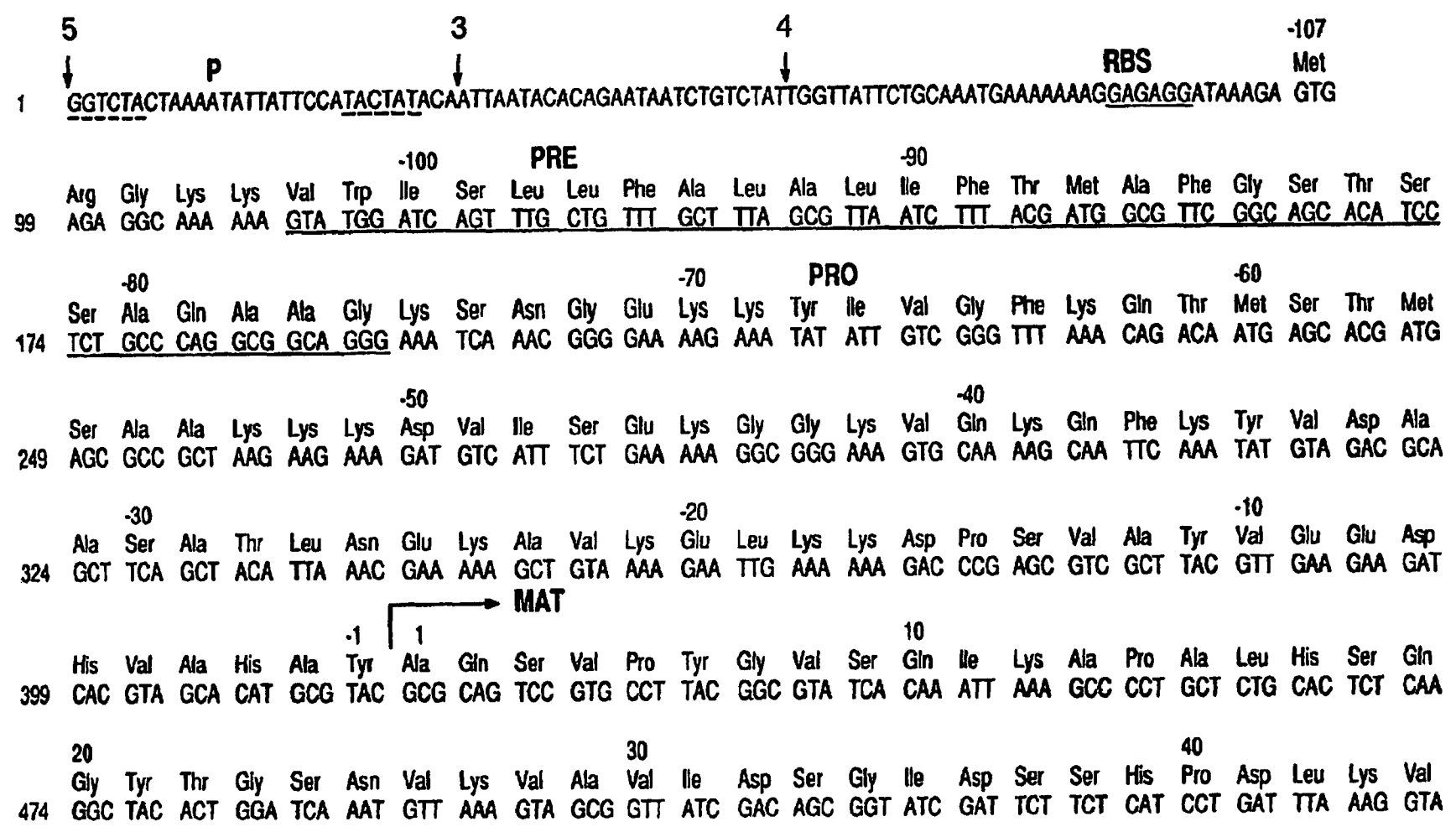

The amino acid position numbers used herein refer to those assigned to the mature *Bacillus amyloliquefaciens* subtilisin sequence presented in FIG. 1. However, it is not intended that the present invention be limited to the mutation of this particular subtilisin. Thus, the present invention encompasses precursor proteases containing amino acid residues at positions which are "equivalent" to the particular identified residues in *Bacillus amyloliquefaciens* subtilisin and which exhibit the same immunogenic response as peptides corresponding to identified residues of *Bacillus amyloliquefaciens*.

"Corresponding to," as used herein, refers to a residue at the enumerated position in a protein or peptide, or a residue that is analogous, homologous, or equivalent to an enumerated residue in a protein or peptide. In some embodiments, the term is used in reference to enumerated residues within the BPN' protease of *B. amyloliquefaciens*.

As used herein, the term "derivative" refers to a protein (e.g., a protease) which is derived from a precursor protein (e.g., the native protease) by addition of one or more amino acids to either or both the C- and N-terminal end(s), substitution of one or more amino acids at one or a number of different sites in the amino acid sequence, deletion of one or more amino acids at either or both ends of the protein or at one or more sites in the amino acid sequence, or insertion of one or more amino acids at one or more sites in the amino acid sequence. The preparation of a protease derivative is preferably achieved by modifying a DNA sequence which encodes for the native protein, transformation of that DNA sequence into a suitable host, and expression of the modified DNA sequence to form the derivative protease.

As used herein, the term "analogous sequence" refers to a sequence within a protein that provides similar function, tertiary structure, and/or conserved residues as the protein of interest. In particularly preferred embodiments, the analogous sequence involves sequence(s) at or near an epitope. For example, in epitope regions that contain an alpha helix or a beta sheet structure, the replacement amino acids in the analogous sequence preferably maintain the same specific structure.

"Homolog" as used herein, means a protein (e.g., protease) which has similar catalytic action, structure, antigenic, and/or immunogenic response as the protein (i.e., protease) of interest. It is not intended that a homolog and a protein (e.g., protease) of interest are not necessarily related evolutionarily. Thus, it is contemplated that the term encompasses the same functional protein (e.g., protease) obtained from different species. In preferred embodiments, it is desirable to identify a homolog that has a tertiary and/or primary structure similar to the protein (e.g., protease) of interest, as replacement of the epitope in the protein (i.e., protease) of interest with an analogous segment from the homolog will reduce the disruptiveness of the change. Thus, in most cases, closely homologous proteins (e.g., proteases) provide the most desirable sources of epitope substitutions (e.g., in other proteases). Alternatively, it is advantageous to look to human analogs for a given protein. For example, it is contemplated that substituting a specific epitope in a bacterial subtilisin with a sequence from a human analog to subtilisin (i.e., human subtilisin) results in a reduced human immunogenic response against the bacterial protein.

The phrase "substantially identical" as used herein (e.g., in the context of two nucleic acids or polypeptides) refers to a polynucleotide or polypeptide which exhibits an altered immunogenic response as described herein and comprises a sequence that has at least 60% sequence identity, preferably at least 80%, more preferably at least 90%, still more preferably 95%, and even more preferably 97% sequence identity, as compared to a reference sequence using a program suitable to make this determination (e.g., BLAST, ALIGN, CLUSTAL) using standard parameters. One indication that two polypeptides are substantially identical is that the first polypeptide is immunologically cross-reactive with the second polypeptide.

Typically, polypeptides that differ by conservative amino acid substitutions are immunologically cross-reactive. Thus, for example, a polypeptide is substantially identical to a second polypeptide, when the two peptides differ only by a conservative substitution. Another indication that two nucleic acid sequences are substantially identical is that the two molecules hybridize to each other under stringent conditions (e.g., within a range of medium to high stringency). Another indication that the two polypeptides are substantially identical is that the two molecules exhibit the same altered immunogenic response in a defined assay.

As used herein, "hybridization" refers to any process by which a strand of a nucleic acid joins with a complementary nucleic acid strand through base-pairing. Thus, strictly speaking, the term refers to the ability of the complement of the target sequence to bind to a test sequence, or vice-versa. "Hybridization conditions" are typically classified by degree of "stringency" of the conditions under which hybridization is measured. The degree of stringency can be based, for example, on the melting temperature (Tm) of the nucleic acid binding complex or probe. For example, "maximum stringency" is typically conducted at about Tm–5° C. (i.e., 5° below the Tm of the probe); "high stringency" is typically conducted at about 5-10° below the Tm; "intermediate stringency" typically is conducted at about 10-20° below the Tm of the probe; and "low stringency" is typically conducted at about 20-25° below the Tm. Alternatively, or in addition, in some embodiments, hybridization conditions are based upon the salt or ionic strength conditions of hybridization and/or one or more stringency washes. For example, 6×SSC=very low stringency 3×SSC=low to medium stringency, 1×SSC=medium stringency, and 0.5×SSC=high stringency. Functionally, maximum stringency conditions find use in identifying nucleic acid sequences having strict identity or near-strict identity with the hybridization probe; while high stringency conditions are used to identify nucleic acid sequences having about 80% or more sequence identity with the probe. For applications requiring high selectivity, relatively stringent conditions are typically used to form the hybrids (e.g., relatively low salt and/or high temperature conditions are used).

The present invention encompasses proteases having altered immunogenicity that are equivalent to those that are derived from the particular microbial strain mentioned. Being "equivalent," means that the proteases are encoded by a polynucleotide capable of hybridizing to the polynucleotide having the sequence as shown in any one of those shown in FIG. 1, under conditions of medium to high stringency and still retaining the altered immunogenic response to human T-cells. Being "equivalent" means that the protease comprises at least 55%, at least 65%, at least 70%, at least 75%, at least 80%, at least 85%, at least 90%, at least 95%, at least 97% or at least 99% identity to the epitope sequences and the variant proteases having such epitopes (e.g. having the amino acid sequence modified).

As used herein, the terms "hybrid proteases" and "fusion proteases" refer to proteins that are engineered from at least two different or "parental" proteins. In preferred embodiments, these parental proteins are homologs of one another. For example, in some embodiments, a preferred hybrid protease or fusion protein contains the N-terminus of a protein and the C-terminus of a homolog of the protein. In some preferred embodiment, the two terminal ends are combined to correspond to the full-length active protein. In alternative preferred embodiments, the homologs share substantial similarity but do not have identical T-cell epitopes. Therefore, in one embodiment, the present invention provides a protease of interest having one or more T-cell epitopes in the C-terminus, but in which the C-terminus is replaced with the C-terminus of a homolog having a less potent T-cell epitope, or fewer or no T-cell epitopes in the C-terminus. Thus, the skilled artisan understands that by being able to identify T-cell epitopes among homologs, a variety of variants producing different immunogenic responses can be formed. Moreover, it is understood that internal portions, and more than one homolog can be used to produce the variants of the present invention.

In some embodiments, the present invention provides protease hybrids constructed using established protein engineering techniques. As described herein, in one embodiment, the hybrid was constructed so that a highly allergenic amino acid sequence of the protein was replaced with a corresponding sequence from a less allergenic homolog. In this instance, the first 122 amino acids of the protease were derived from the subtilisin referred to as "GG36," and the remaining amino acid sequence was derived from the subtilisin referred to as "BPN'".

The variants of the present invention include the mature forms of protein variants, as well as the pro- and prepro-forms of such protein variants. The prepro-forms are the preferred construction since this facilitates the expression, secretion and maturation of the protein variants.

As used herein, "prosequence" refers to a sequence of amino acids bound to the N-terminal portion of the mature form of a protein which when removed results in the appearance of the "mature" form of the protein. Many proteolytic enzymes are found in nature as translational proenzyme products and, in the absence of post-translational processing, are expressed in this fashion. A preferred prosequence for producing protein variants such as protease variants is the putative prosequence of *Bacillus amyloliquefaciens* subtilisin, although other prosequences find use in the present invention.

As used herein, "signal sequence" and "presequence" refer to any sequence of amino acids bound to the N-terminal portion of a protein or to the N-terminal portion of a pro-protein which may participate in the secretion of the mature or pro forms of the protein. This definition of signal sequence is a functional one and is intended to include all those amino acid sequences encoded by the N-terminal portion of the protein gene which participate in the effectuation of the secretion of protein under native conditions. The present invention utilizes such sequences to effect the secretion of the protein variants described herein. In one embodiment, a signal sequence comprises the first seven amino acid residues of the signal sequence from *Bacillus subtilis* subtilisin fused to the remainder of the signal sequence of the subtilisin from *Bacillus lentus* (ATCC 21536).

As used herein, a "prepro" form of a protein variant consists of the mature form of the protein having a prosequence operably linked to the amino terminus of the protein and a "pre" or "signal" sequence operably linked to the amino terminus of the prosequence.

As used herein, "expression vector" refers to a DNA construct containing a DNA sequence that is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid" and "vector" are sometimes used interchangeably as the plasmid is the most commonly used form of vector at present. However, the invention is intended to include such other forms of expression vectors that is serve equivalent functions and which are, or become, known in the art.

As used herein, "host cells" are generally prokaryotic or eukaryotic hosts which preferably have been manipulated by the methods known in the art (See e.g., U.S. Pat. No. 4,760,025 (RE 34,606)) to render them incapable of secreting enzymatically active endoprotease. A preferred host cell for expressing protein is the *Bacillus* strain BG2036 which is deficient in enzymatically active neutral protein and alkaline protease (subtilisin). The construction of strain BG2036 is described in detail in U.S. Pat. No. 5,264,366, hereby incorporated by reference. Other host cells for expressing protein include *Bacillus subtilis* I168 (also described in U.S. Pat. No. 4,760,025 (U.S. RE 34,606) and U.S. Pat. No. 5,264,366, the disclosures of which are incorporated herein by reference), as well as any suitable *Bacillus* strain, including those within the species of *B. licheniformis*, *B. lentus*, and other *Bacillus* species, etc.

Host cells are transformed or transfected with vectors constructed using recombinant DNA techniques known in the art. Transformed host cells are capable of either replicating vectors encoding the protein variants or expressing the desired protein variant. In the case of vectors which encode the pre- or prepro-form of the protein variant, such variants, when expressed, are typically secreted from the host cell into the host cell medium.

"Operably linked" when used in reference to the relationship between two DNA regions, simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The genes encoding the naturally-occurring precursor protein may be obtained in accord with the general methods known to those skilled in the art. The methods generally comprise synthesizing labeled probes having putative sequences encoding regions of the protein of interest, preparing genomic libraries from organisms expressing the protein, and screening the libraries for the gene of interest by hybridization to the probes. Positively hybridizing clones are then mapped and sequenced.

As used herein, an "in vivo reduction in allergenicity" refers to an exhibited decrease in the immunogenic response as determined by an assay that occurs at least in part, within a living organism, (e.g., requires the use of an living animal). Exemplary "in vivo" assays include determination of altered immunogenic responses in mouse models.

As used herein, an "in vitro reduction in allergenicity" means an exhibited decrease in the immunogenic response as determined by an assay that occurs in an artificial environment outside of a living organism (i.e., does not require use of a living animal). Exemplary in vitro assays include testing the proliferative responses by human peripheral blood mononuclear cells to a peptide of interest.

As used herein, "personal care products" means products used in the cleaning of hair, skin, scalp, teeth, including, but not limited to shampoos, body lotions, shower gels, topical moisturizers, toothpaste, and/or other topical cleansers. In some particularly preferred embodiments, these products are utilized by humans, while in other embodiments, these products find use with non-human animals (e.g., in veterinary applications).

As used herein, "skin care compositions" means products used in topical application for cleaning and/or moisturizing skin. Such compositions include, but are not limited to moisturizing body washes, shower gels, body lotions, moisturizing facial creams, make-up removers, and lotions.

As used herein, "cleaning compositions" are compositions that can be used to remove undesired compounds from substrates, such as fabric, dishes, contact lenses, other solid substrates, hair (shampoos), skin (soaps and creams), teeth (mouthwashes, toothpastes) etc.

The term "cleaning composition materials," as used herein, refers to any liquid, solid or gaseous material selected for the particular type of cleaning composition desired and the form of the product (e.g., liquid; granule; spray composition), which materials are also compatible with the protease enzyme used in the composition. The specific selection of cleaning composition materials are readily made by considering the surface, item or fabric to be cleaned, and the desired form of the composition for the cleaning conditions during use (e.g., through the wash detergent use).

As used herein the term "hard surface cleaning composition," refers to detergent compositions for cleaning hard surfaces such as floors, walls, bathroom tile, and the like. Such compositions are provided in any form, including but not limited to solids, liquids, emulsions, etc.

As used herein, "dishwashing composition" refers to all forms for compositions for cleaning dishes, including but not limited to, granular and liquid forms.

As used herein, "fabric cleaning composition" refers to all forms of detergent compositions for cleaning fabrics, including but not limited to, granular, liquid and bar forms. As used herein, "fabric" refers to any textile material.

As used herein, the term "compatible," means that the cleaning composition materials do not reduce the proteolytic activity of the protease enzyme to such an extent that the protease is not effective as desired during normal use situations. Specific cleaning composition materials are exemplified in detail hereinafter.

As used herein, "effective amount of protease enzyme" refers to the quantity of protease enzyme described hereinbefore necessary to achieve the enzymatic activity necessary in the specific application (e.g., personal care product, cleaning composition, etc.). Such effective amounts are readily ascertained by one of ordinary skill in the art and is based on many factors, such as the particular enzyme variant used, the cleaning application, the specific composition of the cleaning composition, and whether a liquid or dry (e.g., granular, bar) composition is required, and the like.

As used herein, "non-fabric cleaning compositions" encompass hard surface cleaning compositions, dishwashing compositions, oral cleaning compositions, denture cleaning compositions, and personal cleansing compositions.

As used herein, "oral cleaning compositions" refers to dentifrices, toothpastes, toothgels, toothpowders, mouthwashes, mouth sprays, mouth gels, chewing gums, lozenges, sachets, tablets, biogels, prophylaxis pastes, dental treatment solutions, and the like.

As used herein, "pharmaceutically-acceptable" means that drugs, medicaments and/or inert ingredients which the term describes are suitable for use in contact with the tissues of humans and other animals without undue toxicity, incompatibility, instability, irritation, allergic response, and the like, commensurate with a reasonable benefit/risk ratio.

DETAILED DESCRIPTION OF THE INVENTION

The present invention provides novel protein variants that exhibit reduced immunogenic responses, as compared to the parental proteins. The present invention further provides DNA molecules that encode novel variants, host cells comprising DNA encoding novel variants, as well as methods for making proteins less allergenic. In addition, the present invention provides various compositions that comprise these proteins that are less immunogenic than the wild-type proteins.

In some particularly preferred embodiments, the present invention provides means to produce variant proteins having altered immunogenic response and allergenic potential as compared to the precursor protease or protease of interest. Thus, the present invention provides variant proteins that are more safe to use than native or precursor proteins. In particularly preferred embodiments, the variant proteins are proteases. In addition to the mutations specifically described herein, the present invention finds use in combination with mutations known in the art to effect altered thermal stability, altered substrate specificity, modified activity (e.g., modified affinity and/or avidity), modified function, increased specific activity, and/or altered pH (e.g., alkaline) stability of proteins. In some embodiments, the present invention provides variant proteins that exhibit one or more altered B-cell and/or T-cell epitope(s).

In preferred embodiments, exposure of an animal to the protease variants of the present invention results in an altered immunogenic response, as compared to exposure of the animal to the precursor protease. In some particularly preferred embodiments, the variant comprises an altered T-cell epitope, such that the variant protease of interest produces different immunogenic response(s) in a human. It is contemplated an "altered immunogenic response" encompasses altered allergenicity, including either increased or decreased immunogenic response. In some embodiments, the altered T-cell epitope comprises at least one substitution and/or deletion of an amino acid selected from those residues within the epitope (i.e., the "epitope of interest" that is altered). In preferred embodiments, the variant proteases of the present invention include variants that produce reduced immunogenic responses, but have other activities comparable to those of the precursor proteases, as well as site mutation variants that do not produce an immunogenic response, and hybrid protease variants.

The present invention further provides methods for altering (e.g. increasing or reducing) the immunogenic response of a protease comprising the steps of: obtaining a precursor protease; and modifying the precursor protease to obtain a variant or derivative of the precursor protease, the variant having at least one T-cell epitope of the precursor protease. In addition, in some embodiments, the variant is characterized as exhibiting an altered immunogenic response, as compared to the immunogenic response stimulated by the precursor protease.

In particularly preferred embodiments of the present invention, T-cell epitopes in subtilisin proteases are modified. These subtilisin T-cell epitopes include: one epitope corresponding to residues 25-39 of the B. amyloliquefaciens subtilisin; one epitope corresponding to residues 88-102 of the B. amyloliquefaciens subtilisin, as set forth in SEQ ID NO:2; one epitope corresponding to residues 154-168 of the B. amyloliquefaciens subtilisin, as set forth in SEQ ID NO:2; one epitope corresponding to residues 160-174 of the B. amyloliquefaciens subtilisin, as set forth in SEQ ID NO:2; one epitope corresponding to residues 163-177 of the B. amyloliquefaciens subtilisin, as set forth in SEQ ID NO:2, and still another corresponding to residues 181-195 of the B. amyloliquefaciens subtilisin, as set forth in SEQ ID NO:2. The method may further include determining the residues which increase or decrease such immunological response. These residues can be determined by peptide screening techniques described herein. In one embodiment, the variant protease exhibiting an altered immunogenic response comprises one or more amino acid substitution(s) corresponding to residue 25, 26, 27, 28, 29, 30, 31, 32, 33, 34, 35, 36, 37, 38, 39, 88, 89, 90, 91, 92, 93, 94, 95, 96, 97, 98, 99, 100, 101, 102, 154, 155, 156, 157, 158, 159, 160, 161, 162, 163, 164, 165, 166, 167, 168, 169, 170, 171, 172, 173, 174, 175, 176, 177, 181, 182, 183, 184, 185, 186, 187, 188, 189, 190, 191, 192, 193, 194 and/or 195 of B. amyloliquefaciens protease subtilisin, as set forth in SEQ ID NO:2, including modified subtilisins such as BPN'. In one embodiment, the variant protease comprises one or more amino acid substitution corresponding to residues consisting of N25A, N25R, N25D, N25C, N25E, N25Q, N25G, N25H, N25I, N25L, N25K, N25M, N25F, N25P, N25S, N25T, N25W, N25Y, N25V, V26A, V26R, V26N, V26D, V26C, V26E, V26Q, V26G, V26H, V26I, V26L, V26K, V26M, V26F, V26P, V26S, V26T, V26W, V26Y, K27A, K27R, K27N, K27D, K27C, K27E, K27Q, K27G, K27H, K27I, K27L, K27M, K27F, K27P, K27S, K27T, K27W, K27Y, K27V, V28A, V28R, V28N, V28D, V28C, V28E, V28Q, V28G, V28H, V28I, V28L, V28K, V28M, V28F, V28P, V28S, V28T, V28W, V28Y, A29R, A29N, A29D, A29C, A29E, A29Q, A29G, A29H, A29I, A29L, A29K, A29M, A29F, A29P, A29S, A29T, A29W, A29Y, A29V, V30A, V30R, V30N, V30D, V30C, V30E, V30Q, V30G, V30H, V30I, V30L, V30K, V30M, V30F, V30P, V30S, V30T, V30W, V30Y, I31A, I31R, I31N, I31D, I31C, I31E, I31Q, I31G, I31H, I31L, I31K, I31M, I31F, I31P, I31S, I31T, I31W, I31Y, I31V; D32A, D32R, D32N; D32C, D32E, D32Q, D32G, D32H, D32I, D32L, D32K, D32M, D32F, D32P, D32S, D32T, D32W, D32Y, D32V, S33A, S33R, S33N, S33D, S33C, S33E, S33Q, S33G, S33H, S33I, S33L, S33K, S33M, S33F, S33P, S33T, S33W, S33Y, S33V, G34A, G34R, G34N, G34D, G34C, G34E, G34Q, G34H, G34I, G34L, G34K, G34M, G34F, G34P, G34S, G34T, G34W, G34Y, G34V, I35A, I35R, I35N, I35D, I35C, I35E, I35Q, I35G, I35H, I35L, I35K, I35M, I35F, I35P, I35S, I35T, I35W, I35Y, I35V, D36A, D36R, D36N, D36C, D36E, D36Q, D36G, D36H, D36I, D36L, D36K, D36M, D36F, D36P, D36S, D36T, D36W, D36Y, D36V, S37A, S37R, S37N, S37D, S37C, S37E, S37Q, S37G, S37H, S37I, S37L, S37K, S37M, S37F, S37P, S37T, S37W, S37Y, S37V, S38A, S38R, S38N, S38D, S38C, S38E, S38Q, S38G, S38H, S38I, S38L, S38K, S38M, S38F, S38P, S38T, S38W, S38Y, S38V, H39A, H39R, H39N, H39D, H39C, H39E, H39Q, H39G, H39I, H39L, H39K, H39M, H39F, H39P, H39S, H39T, H39W, H39Y, H39V, A88R, A88N, A88D, A88C, A88E, A88Q, A88G, A88H, A88I, A88L, A88K, A88M, A88F, A88P, A88S, A88T, A88W, A88Y, A88V, S89A, S89R, S89N, S89D, S89C, S89E, S89Q, S89G, S89H, S89I, S89L, S89K, S89M, S89F, S89P, S89T, S89W, S89Y, S89V, L90A, L90R, L90N, L90D, L90C, L90E, L90Q, L90G, L90H, L90I, L90K, L90M, L90F, L90P, L90S, L90T, L90W, L90Y, L90V, Y91A, Y91R, Y91N, Y91D, Y91C, Y91E, Y91Q, Y91G, Y91H, Y91I, Y91L, Y91K, Y91M, Y91F, Y91P, Y91S, Y91T, Y91W, Y91V, A92R, A92N, A92D, A92C, A92E, A92Q, A92G, A92H, A92I, A92L, A92K, A92M, A92F, A92P, A92S, A92T, A92W, A92Y, A92V, V93A, V93R, V93N, V93D, V93C, V93E, V93Q, V93G, V93H, V93I, V93L, V93K, V93M, V93F, V93P, V93S, V93T, V93W, V93Y, K94A, K94R, K94N, K94D, K94C, K94E, K94Q, K94G, K94H, K94I, K94L, K94M, K94F, K94P, K94S, K94T, K94W, K94Y, K94V, V95A, V95R, V95N, V95D, V95C, V95E, V95Q, V95G, V95H, V95I, V95L, V95K, V95M, V95F, V95P, V95S, V95T, V95W, V95Y, L96A, L96R, L96N, L96D, L96C, L96E, L96Q, L96G, L96H, L96I, L96K, L96M, L96F, L96P, L96S, L96T, L96W, L96Y, L96V, G97A, G97R, G97N, G97D, G97C, G97E, G97Q, G97H, G97I, G97L, G97K, G97M, G97F, G97P, G97S, G97T, G97W, G97Y, G97V, A98R, A98N, A98D, A98C, A98E, A98Q, A98G, A98H, A98I, A98L, A98K, A98M, A98F, A98P, A98S, A98T, A98W, A98Y, A98V, D99A, D99R, D99N, D99C, D99E, D99Q, D99G, D99H, D99I, D99L, D99K, D99M, D99F, D99P, D99S, D99T, D99W, D99Y, D99V, G100A, G100R, G100N, G100D, G100C, G100E, G100Q, G100H, G100I, G100L, G100K, G100M, G100F, G100P, G100S, G100T, G100W, G100Y, G100V, S101A, S101R, S101N, S101D, S101C, S101E, S101Q, S101G, S101H, S101I, S101L, S101K, S101M, S101F, S101P, S101T, S101W, S101Y, S101V, G102A, G102R, G102N, G102D, G102C, G102E, G102Q, G102H, G102I, G102L, G102K, G102M, G102F, G102P, G102S, G102T, G102W, G102Y, G102V, G154A, G154R, G154N, G154D, G154C, G154E, G154Q, G154H, G154I, G154L, G154K, G154M, G154F, G154P, G154S, G154T, G154W, G154Y, G154V, N155A, N155R, N155D, N155C, N155E, N155Q, N155G, N155H, N155I, N155L, N155K, N155M, N155F, N155P, N155S, N155T, N155W, N155Y, N155V, E156A, E156R, E156N, E156D, E156C, E156Q, E156G, E156H, E156I, E156L, E156K, E156M, E156F, E156P, E156S, E156T, E156W, E156Y, E156V, G157A, G157R, G157N, G157D, G157C, G157E, G157Q, G157H, G157I, G157L, G157K, G157M, G157F, G157P, G157S, G157T, G157W, G157Y, G157V, T158A, T158R, T158N, T158D, T158C, T158E, T158Q, T158G, T158H, T158I, T158L, T158K, T158M, T158F, T158P, T158S, T158W, T158Y, T158V, S159A, S159R, S159N, S159D, S159C, S159E, S159Q, S159G, S159H, S159I, S159L, S159K, S159M, S159F, S159P, S159T, S159W, S159Y, S159V, G160A, G160R, G160N, G160D, G160C, G160E, G160Q, G160H, G160I, G160L, G160K, G160M, G160F, G160P, G160S, G160T, G160W, G160Y, G160V, S161A, S161R, S161N, S161D, S161C, S161E, S161Q, S161G, S161H, S161I, S161L, S161K, S161M, S161F, S161P, S161T, S161W, S161Y, S161V, S162A, S162R, S162N, S162D, S162C, S162E, S162Q, S162G, S162H, S162I, S162L, S162K, S162M, S162F, S162P, S162T, S162W, S162Y, S162V, S163A, S163R, S163N, S163D, S163C, S163E, S163Q, S163G, S163H, S163I, S163L, S163K, S163M, S163F, S163P, S163T, S163W, S163Y, S163V, T164A, T164R, T164N, T164D, T164C, T164E, T164Q, T164G, T164H, T164I, T164L, T164K, T164M, T164F, T164P, T164S, T164W, T164Y, T164V, V165A, V165R, V165N, V165D, V165C, V165E, V165Q, V165G, V165H, V165I, V165L, V165K, V165M, V165F, V165P, V165S, V165T, V165W, V165Y, G166A, G166R, G166N, G166D, G166C, G166E, G166Q, G166H, G166I, G166L, G166K, G166M, G166F, G166P, G166S, G166T, G166W, G166Y, G166V, Y167A, Y167R, Y167N, Y167D, Y167C, Y167E, Y167Q, Y167G, Y167H, Y167I, Y167L, Y167K, Y167M, Y167F, Y167P, Y167S, Y167T, Y167W, Y167V, P168A, P168R, P168N, P168D, P168C, P168E, P168Q, P168G, P168H, P168I, P168L, P168K, P168M, P168F, P168S, P168T, P168W, P168Y, P168V, G169A, G169R, G169N, G169D, G169C, G169E, G169Q, G169H, G169I, G169L, G169K, G169M, G169F, G169P, G169S, G169T, G169W, G169Y, G169V, K170A, K170R, K170N, K170D, K170C, K170E, K170Q, K170G, K170H, K170I, K170L, K170M, K170F, K170P, K170S, K170T, K170W, K170Y, K170V, Y171A, Y171R, Y171N, Y171D, Y171C, Y171E, Y171Q, Y171G, Y171H, Y171I, Y171L, Y171K, Y171M, Y171F, Y171P, Y171S, Y171T, Y171W, Y171V, P172A, P172R, P172N, P172D, P172C, P172E, P172Q, P172G, P172H, P172I, P172L, P172K, P172M, P172F, P172S, P172T, P172W, P172Y, P172V, S173A, S173R, S173N, S173D, S173C, S173E, S173Q, S173G, S173H, S173I, S173L, S173K, S173M, S173F, S173P, S173T, S173W, S173Y, S173V, V174A, V174R, V174N, V174D, V174C, V174E, V174Q, V174G, V174H, V174I, V174L, V174K, V174M, V174F, V174P, V174S, V174T, V174W, V174Y, I175A, I175R, I175N, I175D, I175C, I175E, I175Q, I175G, I175H, I175L, I175K, I175M, I175F, I175P, I175S, I175T, I175W, I175Y, I175V, A176R, A176N, A176D, A176C, A176E, A176Q, A176G, A176H, A176I, A176L, A176K, A176M, A176F, A176P, A176S, A176T, A176W, A176Y, A176V, V177A, V177R, V177N, V177D, V177C, V177E, V177Q, V177G, V177H, V177I, V177L, V177K, V177M, V177F, V177P, V177S, V177T, V177W, V177Y, D181A, D181R, D181N, D181C, D181E, D181Q, D181G, D181H, D181I, D181L, D181K, D181M, D181F, D181P, D181S, D181T, D181W, D181Y, D181V, S182A, S182R, S182N, S182D, S182C, S182E, S182Q, S182G, S182H, S182I, S182L, S182K, S182M, S182F, S182P, S182T, S182W, S182Y, S182V, S183A, S183R, S183N, S183D, S183C, S183E, S183Q, S183G, S183H, S183I, S183L, S183K, S183M, S183F, S183P, S183T, S183W, S183Y, S183V, N184A, N184R, N184D, N184C, N184E, N184Q, N184G, N184H, N184I, N184L, N184K, N184M, N184F, N184P, N184S, N184T, N184W, N184Y, N184V, Q185A, Q185R, Q185N, Q185D, Q185C, Q185E, Q185G, Q185I, Q185L, Q185K, Q185M, Q185F, Q185P, Q185S, Q185T, Q185W, Q185Y, Q185V, R186A, R186N, R186D, R186C, R186E, R186Q, R186G, R186H, R186I, R186L, R186K, R186M, R186F, R186P, R186S, R186T, R186W, R186Y, R186V, A187R, A187N, A187D, A187C, A187E, A187Q, A187G, A187H, A187I, A187L, A187K, A187M, A187F, A187P, A187S, A187T, A187W, A187Y, A187V, S188A, S188R, S188N, S188D, S188C, S188E, S188Q, S188G, S188H, S188I, S188L, S188K, S188M, S188F, S188P, S188T, S188W, S188Y, S188V, F189A, F189R, F189N, F189D, F189C, F189E, F189Q, F189G, F189H, F189I, F189L, F189K, F189M, F189P, F189S, F189T, F189W, F189Y, F189V, S190A, S190R, S190N, S190D, S190C, S190E, S190Q, S190G, S190H, S190I, S190L, S190K, S190M, S190F, S190P, S190T, S190W, S190Y, S190V, Q191A, Q191R, Q191N, Q191D, Q191C, Q191E, Q191G, Q191H, Q191I, Q191L, Q191K, Q191M, Q191F, Q191P, Q191S, Q191T, Q191W, Q191Y, Q191V, Y192A, Y192R, Y192N, Y192D, Y192C, Y192E, Y192Q, Y192G, Y192H, Y192I, Y192L, Y192K, Y192M, Y192F, Y192P, Y192S, Y192T, Y192W, Y192V, G193A, G193R, G193N, G193D, G193C, G193E, G193H, G193I, G193L, G193K, G193M, G193F, G193P, G193S, G193T, G193W, G193Y, G193V, P194A, P194R, P194N, P194D, P194C, P194E, P194Q, P194G, P194H, P194I, P194L, P194K, P194M, P194F, P194S, P194T, P194W, P194Y, P194V, E195A, E195R, E195N, E195D, E195C, E195Q, E195G, E195H, E195I, E195L, E195K, E195M, E195F, E195P, E195S, E195T, E195W, E195Y, and/or E195V of *B. amyloliquefaciens* subtilisin, as set forth in SEQ ID NO:2, wherein the substitutions are located within the at least one epitope. In another embodiment, the at least two amino acid substitutions are selected from the above residues, the substitutions being within different epitopes. The resulting variant(s) exhibit an altered immunogenic response as compared to that of the precursor protease.

In one embodiment, the protease having an altered immunogenic response (e.g. an increased immunogenic or decreased immunogenic response), is derived from a protease of interest. In some embodiments, the protease of interest is a wild-type protease, while in other embodiments, it is a mutated variant, conjugated variant, or a hybrid variant having amino acid substitutions in the epitope of interest. In some embodiments, the variant is capable of causing sensitization in an individual or a population. In alternative embodiments, the epitope is identified using an assay designed to identify epitopes and/or non-epitopes. In some preferred embodiments, the methods comprise combining differentiated dendritic cells with naïve human CD4+ and/or CD8+ T-cells and with a peptide of interest. More specifically, a reduced immunogenic response peptide of interest is provided wherein a T-cell epitope is recognized comprising the steps of: (a) obtaining from a single blood source a solution of dendritic cells and a solution of naïve CD4+ and/or CD8+ T-cells; (b) promoting differentiation of the dendritic cells; (c) combining the solution of differentiated dendritic cells and naïve CD4+ and/or CD8+ T-cells with a peptide of interest; and (d) measuring the proliferation of T-cells in step (c).

In some preferred embodiments of the present invention, a series of peptide oligomers that correspond to all or part of the protease of interest are prepared. For example, in some particularly preferred embodiments, a peptide library is produced covering the relevant portion or all of the protein. In one embodiment, the manner of producing the peptides is to introduce overlap into the peptide library. In some embodiments, this involves producing a first peptide corresponds to amino acid sequence 1-15 of the subject protein, a second peptide corresponds to amino acid sequence 4-18 of the subject protein, a third peptide corresponds to amino acid sequence 7-21 of the subject protein, a fourth peptide corresponds to amino acid sequence 10-24 of the subject protein etc. until representative peptides corresponding to the entire molecule are created. However, it is not intended that the present invention be limited to any particular peptide size or overlap. Thus, it is contemplated that peptides of other lengths and overlap (e.g., twelve amino acids) will find use in the present invention.

By analyzing each of the peptides individually in the assay provided herein, means are provided to precisely identify the location of epitopes recognized by T-cells. In the example above, the greater reaction of one specific peptide than its neighbors' facilitates identification of the epitope anchor region to within three amino acids. After determining the location of these epitopes, means are provided to alter the amino acids within each epitope until the peptide produces a different T-cell response from that of the original protein. Moreover, the present invention provides means to identify proteins which have desired low T-cell epitope potency and which are suitable for use in their naturally occurring forms.

In some embodiments, the epitopes determined or identified are then modified so as to alter (e.g., increase or decrease) the immunogenic potential of the protein of interest. In one embodiment, the epitope to be modified produces a level of T-cell proliferation that is greater than approximately three times the baseline T-cell proliferation in a sample. When modified, the epitope produces less than approximately three times the baseline proliferation, preferably less than approximately two times the baseline proliferation and most preferably less than or substantially equal to the baseline proliferation in a sample. In another embodiment, the epitope to be modified produces a level of T-cell proliferation of less than approximately three times the baseline T-cell proliferation in a sample. When modified, the epitope produces greater than approximately three times the baseline proliferation, preferably greater than approximately two times the baseline proliferation and most preferably greater than or substantially equal to the baseline proliferation in a sample.

Various means find use in the modification of epitopes. For example, the amino acid sequence of the epitope can be substituted with an analogous sequence from a human homolog to the protein of interest; the amino acid sequence of the epitope can be substituted with an analogous sequence from a non-human homolog to the protein of interest, which analogous sequence produces a lesser immunogenic (e.g., allergenic) response due to T-cell epitope recognition than that of the protein of interest; the amino acid sequence of the epitope can be substituted with a sequence which substantially mimics the major tertiary structure attributes of the epitope, but which produces a lesser immunogenic (e.g., allergenic) response due to T-cell epitope recognition than that of the protein of interest; and/or with any sequence which produces lesser immunogenic (e.g., allergenic) response due to T-cell epitope recognition than that of the protein of interest.

It should be appreciated that one of skill will readily recognize that epitopes can be modified in other ways depending on the desired outcome. For example, if altering an autoimmune response against self-antigens is desired, it is contemplated the amino acid sequence of an epitope will be substituted with amino acids that decrease or cause a shift in an inflammatory or other immune response.

The present invention extends to all proteins in which it is desired to modulate the immunogenic response. In particularly preferred embodiments, the present invention provides means to modulate the immunogenic response to proteases. In addition, those of skill in the art will readily recognize the proteases of this invention are not necessarily native proteins and peptides. Indeed, in one embodiment of this invention, shuffled genes having an altered immunogenic response are contemplated (See, Stemmer, Proc. Nat'l Acad. Sci. USA 91:10747 [1994]; Patten et al., Curr. Op. Biotechnol., 8:724 [1997]; Kuchner and Arnold, Trends Biotechnol., 15:523 [1997]; Moore et al., J. Mol, Biol., 272:336 [1997]; Zhao et al., Nature Biotechnol., 16:258 [1998]; Giver et al., Proc. Nat'l Acad. Sci. USA 95:12809 (1998); Harayama, Trends Biotechnol., 16:76 [1998]; Lin et al., Biotechnol. Prog., 15:467 [1999]; and Sun, J. Comput. Biol., 6:77 [1999]). Thus, the present invention provides means to alter proteins (e.g., proteases) in order to modulate the immunogenic response to that protein.

Preferably, proteases according to the present invention are isolated or purified. By purification or isolation is meant that the protease is altered from its natural state by virtue of separating the protease from some or all of the naturally occurring constituents with which it is associated in nature.

Such isolation or purification is accomplished using any suitable means known in the art (e.g., ion exchange chromatography, affinity chromatography, hydrophobic separation, dialysis, protease treatment, ammonium sulphate precipitation or other protein salt precipitation, centrifugation, size exclusion chromatography, filtration, microfiltration, gel electrophoresis or separation on a gradient). These methods remove whole cells, cell debris, impurities, extraneous proteins, or enzymes that are undesired in the final composition. It is further possible to then add components to the protease containing composition which provide additional benefits (e.g., activating agents, anti-inhibition agents, desirable ions, compounds to control pH or other enzymes such as cellulase).

In addition to the above proteases, the present invention includes variant proteases that exhibit an altered immunogenic response, e.g., an increased or reduced immunogenic response. Proteins (e.g. proteases), exhibit increased immunogenic response when the T-cell response they evoke is greater than that evoked by a parental (precursor) protein. The net result of this higher response is an increase in the antibodies directed against the variant protein. Proteins exhibit a reduced immunogenic response when the T-cell response they evoke is less than that evoked by a parental protein. The net result of this lower response is lack of antibodies directed against the variant protein.

Exemplary assays useful in ascertaining the reduced immunogenic response of the variant proteins include, but are not limited to in vivo assays, such as transgenic mouse models (e.g., HLA-DR3/DQ2 mouse T cell responses), and in vitro assays (e.g. methods utilizing human peripheral blood mononuclear cells (PBMC) and protease 1 (P1 is a BPN'-Y217L protease) and its variants). In vivo assays useful in ascertaining the reduced immunogenic response include, but are not limited to the use of transgenic mice, rats (Taurog et al., Immunol. Rev., 169:209-223 [1999]), rabbits, pigs, or any other suitable animal species. A transgenic mouse model for testing modified proteins of interest and variants in vivo and determining a reduced immunogenic response, is the HLA-DR3/DQ2 mouse model. These transgenic mice express a haplotype common in the general human population (HLA DR3/DQ2). These animals express HLA-DR3 on B cells and macrophages in the secondary immune organs. In addition, these animals upregulate HLA-DR expression on activated T cells in a manner that is analogous to human T cells. These animals express HLA-DQ2 at lower levels than HLA-DR (i.e., consistent with expression patterns for HLA molecules in humans). In experiments conducted during the development of the present invention, it was determined that protease epitopes of interest were bind to HLA-DQ2 by cell surface binding analyses.

It is noted that there are differences between this mouse model and other HLA transgenic mouse models described in the literature. The HLA mice used by the present inventors express HLA-DR and -DQ in a manner analogous to that observed in humans (i.e., expression of HLA-DQ is quite low, and can not be upregulated by LPS-mediated activation of B cells). This is in stark contrast to other transgenic animals that have been selected to express high levels of a single HLA transgene. In addition, the mice used in the development of the present invention have been crossed onto a murine I-Ab-deficient mouse that eliminates the expression of the endogenous I-Aab heterodimer (See, Grusby et al., Proc. Natl. Acad. Sci. USA 90:3913-3917 [1993]), which corresponds to human DQ. These mice still express mouse MHC class II I-E beta chain, a molecule that is capable of pairing with the HLA-DR alpha chain, to create a mixed dimer that is likely expressed at high levels on antigen-presenting cells. Other HLA transgenic mice have been reported and could be used in a similar manner to evaluate the potential immune responses to those Class II haplotypes (See e.g., Herman et al., J. Immunol., 163:6275-6282 [1999]; Sonderstrup et al., Immunol. Rev., 172:335-343 [1999]; and Taneja and David, Immunol. Rev., 169:67-79 [1999]).

In addition to modifying a wild-type protease so as to alter the immunogenic response stimulated by proteins, including naturally occurring amino acid sequences, the present invention encompasses reducing the immunogenic response of an additionally mutated protein (e.g., a protease that has been altered to change the functional activity of the protease). In many instances, the mutation of protease to produce a desired characteristic (e.g., to increase activity, increase thermal stability, increase alkaline stability and/or oxidative stability), results in the incorporation of one or more new T-cell epitope(s) in the mutated protease. Upon determination of the presence of new T-cell epitopes and determination of substitute amino acids that alter the immunogenic response of the mutated protein, such mutated protease exhibits an altered immunogenic response.

It is not intended that the present invention be limited to any particular proteins nor proteases. However, in order to provide a clear understanding of the present invention, the description herein focuses on the modification of proteases. In particular, the present description focuses on the serine proteases known as subtilisins. A series of naturally-occurring subtilisins is known to be produced and often secreted by various microbial species. Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin-related class of serine proteases. The subtilisins and chymotrypsin-related serine proteases both have a catalytic triad comprising aspartate, histidine and serine. In subtilisins, the relative order of these amino acids, reading from the amino to carboxy terminus, is aspartate-histidine-serine. In the chymotrypsin-related proteases, the relative order, however, is histidine-aspartate-serine. Thus, "subtilisin," as used herein, herein refers to a serine protease having the catalytic triad of subtilisin related proteases. Examples include, but are not limited to the subtilisins included in FIG. 3. Generally and for purposes of the present invention, numbering of the amino acids in proteases corresponds to the numbers assigned to the mature *Bacillus amyloliquefaciens* subtilisin sequence presented in FIG. 1.

A residue (amino acid) of a precursor protease is equivalent to a residue of *Bacillus amyloliquefaciens* subtilisin if it is either homologous (i.e., corresponding in position in either primary or tertiary structure) or analogous to a specific residue or portion of that residue in *Bacillus amyloliquefaciens* subtilisin (i.e., having the same or similar functional capacity to combine, react, or interact chemically).

In order to establish homology to primary structure, the amino acid sequence of a precursor protease is directly compared to the *Bacillus amyloliquefaciens* subtilisin primary sequence and particularly to a set of residues known to be invariant in subtilisins for which the sequence is known. After aligning the conserved residues, allowing for necessary insertions and deletions in order to maintain alignment (i.e., avoiding the elimination of conserved residues through arbitrary deletion and insertion), the residues equivalent to particular amino acids in the primary sequence of *Bacillus amyloliquefaciens* subtilisin are defined. Alignment of conserved residues preferably should conserve 100% of such residues. However, the present invention encompasses embodiments involving alignment of greater than 90%, greater than 75%, and greater than 50% of conserved residues, as these are also adequate to define equivalent residues, provided the precursor protease exhibits the reduced immunogenic response as described herein. In particularly preferred embodiments, conservation of the catalytic triad, Asp32/His64/Ser221 is maintained. The abbreviations and one letter codes for all amino acids in the present invention are standard codes, such as those used by GenBank and PatentIn.

Thus, conserved residues find use in defining the corresponding equivalent amino acid residues of *Bacillus amyloliquefaciens* subtilisin in other subtilisins exhibiting the same or altered immunogenic response. The amino acid sequences of certain of these subtilisins can be aligned with the sequence of *Bacillus amyloliquefaciens* subtilisin to produce the maximum homology of conserved residues.

Homologous sequences can also be determined by using a "sequence comparison algorithm." Optimal alignment of sequences for comparison can be conducted, e.g., by the local homology algorithm of Smith and Waterman (Smith and Waterman, Adv. Appl. Math., 2:482 [1981]), by the homology alignment algorithm of Needleman and Wunsch (Needleman and Wunsch, J. Mol. Biol., 48:443 [1970]), by the search for similarity method of Pearson and Lipman (Pearson and Lipman, Proc. Natl. Acad. Sci. USA 85:2444 [1988]), by computerized implementations of these algorithms (e.g., GAP, BESTFIT, FASTA, and TFASTA in the Wisconsin Genetics Software Package, Genetics Computer Group, Madison, Wis.), or by visual inspection.

An example of an algorithm that is suitable for determining sequence similarity is the BLAST algorithm (See e.g., Altschul et al., J. Mol. Biol., 215:403-410 [1990]). Software for performing BLAST analyses is publicly available through the National Center for Biotechnology Information. This algorithm involves first identifying high scoring sequence pairs (HSPs) by identifying short words of length "W" in the query sequence that either match or satisfy some positive-valued threshold score "T." when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity "X" from a maximum achieved value; the cumulative score goes to zero or below; or the end of either sequence is reached. The BLAST algorithm parameters "W," "T," and "X" determine the sensitivity and speed of the alignment. The BLAST program uses as defaults a wordlength (W) of 11, the BLOSUM62 scoring matrix (See, Henikoff and Henikoff, Proc. Natl. Acad. Sci. USA 89:10915 [1989]) alignments (B) of 50, expectation (E) of 10, M'5, N'-4, and a comparison of both strands.

The BLAST algorithm then performs a statistical analysis of the similarity between two sequences (See e.g., Karlin and Altschul, Proc. Nat'l. Acad. Sci. USA 90:5873-5787 [1993]). One measure of similarity provided by the BLAST algorithm is the smallest sum probability (P(N)), which provides an indication of the probability by which a match between two nucleotide or amino acid sequences would occur by chance. For example, an amino acid sequence is considered similar to a protein such as a protease if the smallest sum probability in a comparison of the test amino acid sequence to a protein such as a protease amino acid sequence is less than about 0.1, more preferably less than about 0.01, and most preferably less than about 0.001.

In some embodiments, "equivalent residues" are defined by determining homology at the level of tertiary structure for a precursor protein whose tertiary structure has been determined by x-ray crystallography. Equivalent residues are defined as those for which the atomic coordinates of two or more of the main chain atoms of a particular amino acid residue of the precursor protein such as the protease and *Bacillus amyloliquefaciens* subtilisin (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the protein such as the protease in question to the *Bacillus amyloliquefaciens* subtilisin. The best model is the crystallographic model giving the lowest R factor for experimental diffraction data at the highest resolution available.

Equivalent residues which are functionally equivalent to a specific residue of *Bacillus amyloliquefaciens* subtilisin are defined as those amino acids of the precursor protease which may adopt a conformation such that they either alter, modify or contribute to protein structure, substrate binding or catalysis in a manner defined and attributed to a specific residue of the *Bacillus amyloliquefaciens* subtilisin. Further, they are those residues of the precursor protein, for example, protease (for which a tertiary structure has been obtained by x-ray crystallography) which occupy a position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *Bacillus amyloliquefaciens* subtilisin. The coordinates of the three dimensional structure of *Bacillus amyloliquefaciens* subtilisin are set forth in EPO Publication No. 0 251 446 (equivalent to U.S. Pat. No. 5,182,204, incorporated herein by reference) and can be used as outlined above to determine equivalent residues on the level of tertiary structure.

The present invention also encompasses derivatives of proteins (eg., proteases) and/or peptide fragments thereof comprising altered amino acid sequences in comparison with a precursor amino acid sequence (e.g., a "wild type" or "native" protein). In preferred embodiments, these derivative proteins retain the characteristic nature of the precursor protein, but have additional altered properties in some specific aspect. For example, in some embodiments, protease derivatives have an increased pH optimum, increased temperature, and/or increased oxidative stability, but retain their characteristic substrate activity. Similarly, additional derivatives according to the present invention include a calcium binding domain which has either been added, removed or modified in such a way so as to significantly impair or enhance its calcium binding ability. Similarly, a catalytic proteolytic domain may either be added, removed or modified to operate in conjunction with the protease. It is contemplated that in some embodiments of the present invention, derivatives are derived from a DNA fragment encoding a protease derivative wherein the functional activity of the expressed protease derivative is retained. Suitable methods for such modification of the precursor DNA sequence include methods disclosed herein, as well as methods known to those skilled in the art (See e.g., EP 0 328299, and WO89/06279). In some embodiments, some of the residues identified for substitution, insertion or deletion are conserved residues, while in other embodiments, they are not.

In preferred embodiments, modification is preferably made to the "precursor DNA sequence" which encodes the amino acid sequence of the precursor enzyme, but can be by the manipulation of the precursor protein. Examples of a precursor DNA sequence include, but are not limited to BPN', BPN'-Y217L, BPN'-Y217L, N76D, I122A, BPN'-I122A. In the case of residues which are not conserved, the replacement of one or more amino acids is limited to substitutions which produce a variant which has an amino acid sequence that does not correspond to one found in nature. In the case of conserved residues, such replacements should not result in a naturally-occurring sequence. Derivatives provided by the present invention further include chemical modification that change the characteristics of the protease.

In some preferred embodiments, the protein gene is ligated into an appropriate expression plasmid. The cloned protein gene is then used to transform or transfect a host cell in order to express the protein gene. This plasmid may replicate in hosts in the sense that it contains the well-known elements necessary for plasmid replication or the plasmid may be designed to integrate into the host chromosome. The necessary elements are provided for efficient gene expression (e.g., a promoter operably linked to the gene of interest). In some embodiments, these necessary elements are supplied as the gene's own homologous promoter if it is recognized, (i.e., transcribed, by the host), a transcription terminator (a polyadenylation region for eukaryotic host cells) which is exogenous or is supplied by the endogenous terminator region of the protein gene. In some embodiments, a selection gene such as an antibiotic resistance gene that enables continuous cultural maintenance of plasmid-infected host cells by growth in antibiotic-containing media is also included.

In some embodiments, the gene is a natural (i.e., native) gene from *B. amyloliquefaciens*. Alternatively, a synthetic gene encoding a naturally-occurring or mutant precursor protein may be produced. In such an approach, the DNA and/or amino acid sequence of the precursor protein is/are determined. Multiple, overlapping synthetic single-stranded DNA fragments are then synthesized, which upon hybridization and ligation produce a synthetic DNA encoding the precursor protein. An example of synthetic gene construction is set forth in Example 3 of U.S. Pat. No. 5,204,015, the disclosure of which is incorporated herein by reference.

Once the naturally-occurring or synthetic precursor protein gene has been cloned, a number of modifications are undertaken to enhance the use of the gene beyond synthesis of the naturally-occurring precursor protein. Such modifications include the production of recombinant proteins as disclosed in U.S. Pat. No. 4,760,025 (RE 34,606) and EPO Publication No. 0 251 446 and the production of protein variants described herein.

It is intended that protein variants be made using any suitable method. For example, there is a wide variety of different mutagenesis techniques well known to those skilled in the art. Mutagenesis kits are also available from many commercial molecular biology suppliers. Methods are available to make specific substitutions at defined amino acids (site-directed), specific or random mutations in a localized region of the gene (region-specific) or random mutagenesis over the entire gene (saturation mutagenesis). Site-directed mutagenesis of single-stranded DNA or double-stranded DNA using PCR, cassette mutagenesis, gene synthesis, error-prone PCR, and chemical saturation mutagenesis are all techniques that one can use to generate the desired protein variants. After the variants are produced, they can be screened for the desired property (e.g., altered or low or reduced immunogenic response, increased thermal or alkaline stability, etc.).

In one aspect of the invention, the objective is to secure a variant protein having altered immunogenic response potential as compared to the precursor protein. While the instant invention is useful to reduce the immunogenic response produced by a protein, the mutations specified herein find use in combination with mutations known in the art to result altered thermal stability and/or altered substrate specificity, modified activity, improved specific activity or altered alkaline stability as compared to the precursor.

Accordingly, the present invention is directed to altering the capability of the T-cell epitope, which includes residue positions 25-39 in *B. amyloliquefaciens* to induce T-cell proliferation. Embodiments of the invention comprise making at least one modification (e.g., substitution and/or deletion), at one of positions 25, 26, 27, 28, 29, 30, 31, 32, 33, 34, 35, 36, 37, 38, 39, 88, 89, 90, 91, 92, 93, 94, 95, 96, 97, 98, 99, 100, 101, 102, 154, 155, 156, 157, 158, 159, 160, 161, 162, 163, 164, 165, 166, 167, 168, 169, 170, 171, 172, 173, 174, 175, 176, 177, 181, 182, 183, 184, 185, 186, 187, 188, 189, 190, 191, 192, 193, 194, and 195 of *Bacillus amyloliquefaciens* subtilisin, as set forth in SEQ ID NO:2. In alternative embodiments, the present invention provides modifications at more than one of positions 25, 26, 27, 28, 29, 30, 31, 32, 33, 34, 35, 36, 37, 38 and 39 of *Bacillus amyloliquefaciens* subtilisin, as set forth in SEQ ID NO:2. In yet other embodiments, modifications are made at 2 to 10 positions selected from position 25, 26, 27, 28, 29, 30, 31, 32, 33, 34, 35, 36, 37, 38 and 39 of *Bacillus amyloliquefaciens* subtilisin, as set forth in SEQ ID NO:2. Still another embodiment comprises modifications at 2 to 5 positions selected from positions 25, 26, 27, 28, 29, 30, 31, 32, 33, 34, 35, 36, 37, 38 and 39 of *Bacillus amyloliquefaciens* subtilisin, as set forth in SEQ ID NO:2. In combination with the presently disclosed mutation(s) in the region corresponding to amino acid residues 25-39, 88-102, 154-177, and 181 to 195 of *Bacillus amyloliquefaciens* subtilisin, as set forth in SEQ ID NO:2, the present invention further optionally contemplates a mutation (e.g., a substitution) at position 76, and/or optionally in combination with one or more substitutions selected from the group consisting of positions corresponding to 3, 31, 40, 41, 50, 103, 104, 159, 232, 236, 245, 248, 252, 107, 111, 122, 147, 218, 206, and/or 217 of *B. amyloliquefaciens* subtilisin, as set forth in SEQ ID NO:2.

The present invention further provides combinations of substituted residues, for example a combination of at least 2 residues, at least 3 residues, at least 4 residues, at least 5 residues, at least 2-5 residues, and at least 2-10 residue combinations corresponding to positions: 25, 26, 27, 28, 29, 30, 31, 32, 33, 34, 35, 36, 37, 38, 39, 88, 89, 90, 91, 92, 93, 94, 95, 96, 97, 98, 99, 100, 101, 102, 154, 155, 156, 157, 158, 159, 160, 161, 162, 163, 164, 165, 166, 167, 168, 169, 170, 171, 172, 173, 174, 175, 176, 177, 181, 182, 183, 184, 185, 186, 187, 188, 189, 190, 191, 192, 193, 194, and 195 of *Bacillus amyloliquefaciens* subtilisin, as set forth in SEQ ID NO:2, optionally in combination with one or more substitutions selected from the group consisting of positions corresponding to: 3, 31, 40, 41, 50, 103, 104, 159, 232, 236, 245, 248, 252, 107, 111, 122, 147, 218, 206, and/or 217 of *Bacillus amyloliquefaciens* subtilisin, as set forth in SEQ ID NO:2. Such mutations find use in decreasing the allergenic potential of the variant protein of the invention, as well as modulating the overall stability and/or proteolytic activity of the enzyme.

More particularly, the specific substitutions include at least one modification (e.g., substitution) of all twenty two amino acids, including but not limited to the amino acid residues of alanine, arginine, asparagine, aspartic acid, cysteine, glutamic acid, glutamine, glycine, histidine, hydroxylysine, hydroxyproline, isoleucine, leucine, lysine, methionine, phenylalanine, proline, serine, threonine, tryptophan, tyrosine, and/or valine (e.g., N25A, N25R, N25D, N25C, N25E, N25Q, N25G, N25H, N25I, N25L, N25K, N25M, N25F, N25P, N25S, N25T, N25W, N25Y, N25V, V26A, V26R, V26N, V26D, V26C, V26E, V26Q, V26G, V26H, V26I, V26L, V26K, V26M, V26F, V26P, V26S, V26T, V26W, V26Y, K27A, K27R, K27N, K27D, K27C, K27E, K27Q, K27G, K27H, K27I, K27L, K27M, K27F, K27P, K27S, K27T, K27W, K27Y, K27V, V28A, V28R, V28N, V28D, V28C, V28E, V28Q, V28G, V28H, V28I, V28L, V28K, V28M, V28F, V28P, V28S, V28T, V28W, V28Y, A29R, A29N, A29D, A29C, A29E, A29Q, A29G, A29H, A29I, A29L, A29K, A29M, A29F, A29P, A29S, A29T, A29W, A29Y, A29V, V30A, V30R, V30N, V30D, V30C, V30E, V30Q, V30G, V30H, V30I, V30L, V30K, V30M, V30F, V30P, V30S, V30T, V30W, V30Y, I31A, I31R, I31N, I31D, I31C, I31E, I31Q, I31G, I31H, I31L, I31K, I31M, I31F, I31P, I31S, I31T, I31W, I31Y, I31V, D32A, D32R, D32N, D32C, D32E, D32Q, D32G, D32H, D32I, D32L, D32K, D32M, D32F, D32P, D32S, D32T, D32W, D32Y, D32V, S33A, S33R, S33N, S33D, S33C, S33E, S33Q, S33G, S33H, S33I, S33L, S33K, S33M, S33F, S33P, S33T, S33W, S33Y, S33V, G34A, G34R, G34N, G34D, G34C, G34E, G34Q, G34H, G34I, G34L, G34K, G34M, G34F, G34P, G34S, G34T, G34W, G34Y, G34V, I35A, I35R, I35N, I35D, I35C, I35E, I35Q, I35G, I35H, I35L, I35K, I35M, I35F, I35P, I35S, I35T, I35W, I35Y, I35V, D36A, D36R, D36N, D36C, D36E, D36Q, D36G, D36H, D36I, D36L, D36K, D36M, D36F, D36P, D36S, D36T, D36W, D36Y, D36V, S37A, S37R, S37N, S37D, S37C, S37E, S37Q, S37G, S37H, S37I, S37L, S37K, S37M, S37F, S37P, S37T, S37W, S37Y, S37V, S38A, S38R, S38N, S38D, S38C, S38E, S38Q, S38G, S38H, S38I, S38L, S38K, S38M, S38F, S38P, S38T, S38W, S38Y, S38V, H39A, H39R, H$_{39}$N, H39D, H$_{39}$C, H39E, H39Q, H39G, H39I, H39L, H39K, H39M, H39N, H$_{39}$F, H39P, H39S, H39T, H39W, H39Y, H39V, A88R, A88N, A88D, A88C, A88E, A88Q, A88G, A88H, A88I, A88L, A88K, A88M, A88F, A88P, A88S, A88T, A88W, A88Y, A88V, S89A, S89R, S89N, S89D, S89C, S89E, S89Q, S89G, S89H, S89I, S89L, S89K, S89M, S89F, S89P, S89T, S89W, S89Y, S89V, L90A, L90R, L90N, L90D, L90C, L90E, L90Q, L90G, L90H, L90I, L90K, L90M, L90F, L90P, L90S, L90T, L90W, L90Y, L90V, Y91A, Y91R, Y91N, Y91D, Y91C, Y91E, Y91Q, Y91G, Y91H, Y91I, Y91L, Y91K, Y91M, Y91F, Y91P, Y91S, Y91T, Y91W, Y91V, A92R, A92N, A92D, A92C, A92E, A92Q, A92G, A92H, A92I, A92L, A92K, A92M, A92F, A92P, A92S, A92T, A92W, A92Y, A92V, V93A, V93R, V93N, V93D, V93C, V93E, V93Q, V93G, V93H, V93I, V93L, V93K, V93M, V93F, V93P, V93S, V93T, V93W, V93Y, K94A, K94R, K94N, K94D, K94C, K94E, K94Q, K94G, K94H, K94I, K94L, K94M, K94F, K94P, K94S, K94T, K94W, K94Y, K94V, V95A, V95R, V95N, V95D, V95C, V95E, V95Q, V95G, V95H, V95I, V95L, V95K, V95M, V95F, V95P, V95S, V95T, V95W, V95Y, L96A, L96R, L96N, L96D, L96C, L96E, L96Q, L96G, L96H, L96I, L96K, L96M, L96F, L96P, L96S, L96T, L96W, L96Y, L96V, G97A, G97R, G97N, G97D, G97C, G97E, G97Q, G97H, G97I, G97L, G97K, G97M, G97F, G97P, G97S, G97T, G97W, G97Y, G97V, A98R, A98N, A98D, A98C, A98E, A98Q, A98G, A98H, A98I, A98L, A98K, A98M, A98F, A98P, A98S, A98T, A98W, A98Y, A98V, D99A, D99R, D99N, D99C, D99E, D99Q, D99G, D99H, D99I, D99L, D99K, D99M, D99F, D99P, D99S, D99T, D99W, D99Y, D99V, G100A, G100R, G100N, G100D, G100C, G100E, G100Q, G100H, G100I, G100L, G100K, G100M, G100F, G100P, G100S, G100T, G100W, G100Y, G100V, S101A, S101R, S101N, S101D, S101C, S101E, S101Q, S101G, S101H, S101I, S101L, S101K, S101M, S101F, S101P, S101T, S101W, S101Y, S101V, G102A, G102R, G102N, G102D, G102C, G102E, G102Q, G102H, G102I, G102L, G102K, G102M, G102F, G102P, G102S, G102T, G102W, G102Y, G102V, G154A, G154R, G154N, G154D, G154C, G154E, G154Q, G154H, G154I, G154L, G154K, G154M, G154F, G154P, G154S, G154T, G154W, G154Y, G154V, N155A, N155R, N155D, N155C, N155E, N155Q, N155G, N155H, N155I, N155L, N155K, N155M, N155F, N155P, N155S, N155T, N155W, N155Y, N155V, E156A, E156R, E156N, E156D, E156C, E156Q, E156G, E156H, E156I, E156L, E156K, E156M, E156F, E156P, E156S, E156T, E156W, E156Y, E156V, G157A, G157R, G157N, G157D, G157C, G157E, G157Q, G157H, G157I, G157L, G157K, G157M, G157F, G157P, G157S, G157T, G157W, G157Y, G157V, T158A, T158R, T158N, T158D, T158C, T158E, T158Q, T158G, T158H, T158I, T158L, T158K, T158M, T158F, T158P, T158S, T158W, T158Y, T158V, S159A, S159R, S159N, S159D, S159C, S159E, S159Q, S159G, S159H, S159I, S159L, S159K, S159M, S159F, S159P, S159T, S159W, S159Y, S159V, G160A, G160R, G160N, G160D, G160C, G160E, G160Q, G160H, G160I, G160L, G160K, G160M, G160F, G160P, G160S, G160T, G160W, G160Y, G160V, S161A, S161R, S161N, S161D, S161C, S161E, S161Q, S161G, S161H, S161I, S161L, S161K, S161M, S161F, S161P, S161T, S161W, S161Y, S161V, S162A, S162R, S162N, S162D, S162C, S162E, S162Q, S162G, S162H, S162I, S162L, S162K, S162M, S162F, S162P, S162T, S162W, S162Y, S162V, S163A, S163R, S163N, S163D, S163C, S163E, S163Q, S163G, S163H, S163I, S163L, S163K, S163M, S163F, S163P, S163T, S163W, S163Y, S163V, T164A, T164R, T164N, T164D, T164C, T164E, T164Q, T164G, T164H, T164I, T164L, T164K, T164M, T164F, T164P, T164S, T164W, T164Y, T164V, V165A, V165R, V165N, V165D, V165C, V165E, V165Q, V165G, V165H, V165I, V165L, V165K, V165M, V165F, V165P, V165S, V165T, V165W, V165Y, G166A, G166R, G166N, G166D, G166C, G166E, G166Q, G166H, G166I, G166L, G166K, G166M, G166F, G166P, G166S, G166T, G166W, G166Y, G166V, Y167A, Y167R, Y167N, Y167D, Y167C, Y167E, Y167Q, Y167G, Y167H, Y167I, Y167L, Y167K, Y167M, Y167F, Y167P, Y167S, Y167T, Y167W, Y167V, P168A, P168R, P168N, P168D, P168C, P168E, P168Q, P168G, P168H, P168I, P168L, P168K, P168M, P168F, P168S, P168T, P168W, P168Y, P168V, G169A, G169R, G169N, G169D, G169C, G169E, G169Q, G169H, G169I, G169L, G169K, G169M, G169F, G169P, G169S, G169T, G169W, G169Y, G169V, K170A, K170R, K170N, K170D, K170C, K170E, K170Q, K170G, K170H, K170I, K170L, K170M, K170F, K170P, K170S, K170T, K170W, K170Y, K170V, Y171A, Y171R, Y171N, Y171D, Y171C, Y171E, Y171Q, Y171G, Y171H, Y171I, Y171L, Y171K, Y171M, Y171F, Y171P, Y171S, Y171T, Y171W, Y171V, P172A, P172R, P172N, P172D, P172C, P172E, P172Q, P172G, P172H, P172I, P172L, P172K, P172M, P172F, P172S, P172T, P172W, P172Y, P172V, S173A, S173R, S173N, S173D, S173C, S173E, S173Q, S173G, S173H, S173I, S173L, S173K, S173M, S173F, S173P, S173T, S173W, S173Y, S173V, V174A, V174R, V174N, V174D, V174C, V174E, V174Q, V174G, V174H, V174I, V174L, V174K, V174M, V174F, V174P, V174S, V174T, V174W, V174Y, I175A, I175R, I175N, I175D, I175C, I175E, I175Q, I175G, I175H, I175L, I175K, I175M, I175F, I175P, I175S, I175T, I175W, I175Y, I175V, A176R, A176N, A176D, A176C, A176E, A176Q, A176G, A176H, A176I, A176L, A176K, A176M, A176F, A176P, A176S, A176T, A176W, A176Y, A176V, V177A, V177R, V177N, V177D, V177C, V177E, V177Q, V177G, V177H, V177I, V177L, V177K, V177M, V177F, V177P, V177S, V177T, V177W, V177Y, D181A, D181R, D181N, D181C, D181E, D181Q, D181G, D181H, D181I, D181L, D181K, D181M, D181F, D181P, D181S, D181T, D181W, D181Y, D181V, S182A, S182R, S182N, S182D, S182C, S182E, S182Q, S182G, S182H, S182I, S182L, S182K, S182M, S182F, S182P, S182T, S182W, S182Y, S182V, S183A, S183R, S183N, S183D, S183C, S183E, S183Q, S183G, S183H, S183I, S183L, S183K, S183M, S183F, S183P, S183T, S183W, S183Y, S183V, N184A, N184R, N184D, N184C, N184E, N184Q, N184G, N184H, N184I, N184L, N184K, N184M, N184F, N184P, N184S, N184T, N184W, N184Y, N184V, Q185A, Q185R, Q185N, Q185D, Q185C, Q185E, Q185G, Q185H, Q185I, Q185L, Q185K, Q185M, Q185F, Q185P, Q185S, Q185T, Q185W, Q185Y, Q185V, R186A, R186N, R186D, R186C, R186E, R186Q, R186G, R186H, R186I, R186L, R186K, R186M, R186F, R186P, R186S, R186T, R186W, R186Y, R186V, A187R, A187N, A187D, A187C, A187E, A187Q, A187G, A187H, A187I, A187L, A187K, A187M, A187F, A187P, A187S, A187T, A187W, A187Y, A187V, S188A, S188R, S188N, S188D, S188C, S188E, S188Q, S188G, S188H, S188I, S188L, S188K, S188M, S188F, S188P, S188T, S188W, S188Y, S188V, F189A, F189R, F189N, F189D, F189C, F189E, F189Q, F189G, F189H, F189I, F189L, F189K, F189M, F189P, F189S, F189T, F189W, F189Y, P189V, S190A, S190R, S190N, S190D, S190C, S190E, S190Q, S190G, S190H, S190I, S190L, S190K, S190M, S190F, S190P, S190T, S190W, S190Y, S190V, Q191A, Q191R, Q191N, Q191D, Q191C, Q191E, Q191G, Q191H, Q191I, Q191L, Q191K, Q191M, Q191F, Q191P, Q191S, Q191T, Q191W, Q191Y, Q191V, Y192A, Y192R, Y192N, Y192D, Y192C, Y192E, Y192Q, Y192G, Y192H, Y192I, Y192L, Y192K, Y192M, Y192F, Y192P, Y192S, Y192T, Y192W, Y192V, G193A, G193R, G193N, G193D, G193C, G193E, G193Q, G193H, G193I, G193L, G193K, G193M, G193F, G193P, G193S, G193T, G193W, G193Y, G193V, P194A, P194R, P194N, P194D, P194C, P194E, P194Q, P194G, P194H, P194I, P194L, P194K, P194M, P194F, P194S, P194T, P194W, P194Y, P194V, E195A, E195R, E195N, E195D, E195C, E195Q, E195G, E195H, E195I, E195L, E195K, E195M, E195F, E195P, E195S, E195T, E195W, E195Y, and/or E195V) of *Bacillus amyloliquefaciens* subtilisin, as set forth in SEQ ID NO:2.

Based on the screening results obtained with the variant proteins, it is contemplated that at least some of the mutations listed above in *Bacillus amyloliquefaciens* subtilisin are important to the proteolytic activity, performance and/or stability of these enzymes and the cleaning or wash performance as well as other applications of such variant enzymes.

In addition to the point mutations described above, fusing two homologous proteins can also eliminate T-cell epitopes. As is exemplified below, a region of a protein in which a T-cell epitope resides may be replaced with the same region in a homologous protein that doesn't have the T-cell epitope. In one embodiment, a fusion protein is created with protease from *B. lentus* and its *B. amyloliquefaciens* homolog, so that the resulting protein does not have the T-cell epitope present in the parental *B. lentus* protease. Sequence of any length can be fused into the parental protein, from only the epitope to the majority of the protein, as long as the desired activity is maintained. However, it is not necessary that the original level of activity be maintained. Because of the lowered allergenicity of the protein, it may be possible to use more of the hybrid protein than of the parental protein to achieve the same activity levels.

The variant protease activity can be determined and compared with the protease of interest by examining the interaction of the protease with various commercial substrates, including, but not limited to casein, keratin, elastin, and collagen. Indeed, protease activity can be determined by any suitable method known in the art. Exemplary assays to determine protease activity include, but are not limited to, succinyl-Ala-Ala-Pro-Phe-para nitroanilide (SAAPFpNA) (citation) assay, and 2,4,6-trinitrobenzene sulfonate sodium salt (TNBS) assay. In the SAAPFpNA assay, proteases cleave the bond between the peptide and p-nitroaniline to give a visible yellow colour absorbing at 405 nm. In the TNBS color reaction method, the assay measures the enzymatic hydrolysis of the substrate into polypeptides containing free amino groups. These amino groups react with TNBS to form a yellow colored complex. Thus, the more deeply colored the reaction, the more activity is measured. The yellow color can be determined by various analyzers or spectrophotometers known in the art.

Other characteristics of the variant proteases can be determined by methods known to those skilled in the art. Exemplary characteristics include, but are not limited to thermal stability, alkaline stability, and stability of the particular protease in various substrate or is buffer solutions or product formulations.

When combined with the enzyme stability assay procedures disclosed herein, mutants obtained by random mutagenesis can be identified which demonstrated either increased or decreased alkaline or thermal stability while maintaining enzymatic activity.

Alkaline stability can be measured either by known procedures or by the methods described herein. A substantial change in alkaline stability is evidenced by at least about a 5% or greater increase or decrease (in most embodiments, it is preferably an increase) in the half-life of the enzymatic activity of a mutant when compared to the precursor carbonyl hydrolase. In the case of subtilisins, alkaline stability can be measured as a function of enzymatic activity of subtilisin at varying pH.

Thermal stability can be measured either by known procedures or by the methods described herein. A substantial change in thermal stability is evidenced by at least about a 5% or greater increase or decrease (in most embodiments, it is preferably an increase) in the half-life of the catalytic activity of a mutant when exposed to a relatively high temperature and neutral pH as compared to the precursor carbonyl hydrolase. In the case of subtilisins, thermal stability is measured by the autoproteolytic degradation of subtilisin at elevated temperatures and various pHs.

Many of the protein variants of the present invention are useful in formulating various detergent compositions. A number of known compounds are suitable surfactants useful in compositions comprising the protein mutants of the invention. These include nonionic, anionic, cationic, anionic or zwitterionic detergents (See e.g., U.S. Pat. No. 4,404,128 and U.S. Pat. No. 4,261,868). A suitable detergent formulation is that described in Example 7 of U.S. Pat. No.

5,204,015 (previously incorporated by reference). Those in the art are familiar with the different formulations which find use as cleaning compositions. In addition to typical cleaning compositions, it is readily understood that the protein variants of the present invention find use in any purpose that native or wild-type proteins are used. Thus, these variants can be used, for example, in bar or liquid soap applications, dishcare formulations, surface cleaning applications, contact lens cleaning solutions or products, peptide hydrolysis, waste treatment, textile applications, as fusion-cleavage enzymes in protein production, etc. Indeed, it is not intended that the variants of the present invention be limited to any particular use. For example, the variants of the present invention may comprise, in addition to decreased allergenicity, enhanced performance in a detergent composition (as compared to the precursor). As used herein, enhanced performance in a detergent is defined as increasing cleaning of certain enzyme sensitive stains (e.g., grass or blood), as determined by usual evaluation after a standard wash cycle.

Proteins, particularly proteases of the invention can be formulated into known powdered and liquid detergents having pH between 6.5 and 12.0 at levels of about 0.01 to about 5% (preferably 0.1% to 0.5%) by weight. In some embodiments, these detergent cleaning compositions further include other enzymes such as proteases, amylases, cellulases, lipases or endoglycosidases, as well as builders and stabilizers.

The addition of proteins, particularly the proteases of the present invention, to conventional cleaning compositions does not create any special use limitation. In other words, any temperature and pH suitable for the detergent are also suitable for the present compositions, as long as the pH is within the above range, and the temperature is below the described protein's denaturing temperature. In addition, proteins of the invention can be used in a cleaning composition without detergents, again either alone or in combination with builders and stabilizers.

In one embodiment, the present invention provides compositions for the treatment of textiles that includes variant proteins of the present invention. The composition can be used to treat for example silk or wool (See e.g., RD 216,034; EP 134,267; U.S. Pat. No. 4,533,359; and EP 344,259). These variants can be screened for proteolytic activity according to methods well known in the art. Preferred protease variants include multiple substitutions at positions corresponding to 76, 79, and/or 122 of *Bacillus amyloliquefaciens* subtilisin.

The proteins of the present invention exhibit modified immunogenic responses when compared to the native proteins encoded by their precursor DNAs. In some preferred embodiments, the proteins (e.g., proteases) exhibit reduced allergenicity. Those of skill in the art readily recognize that the uses of the proteases of this invention will be determined, in large part, on the immunological properties of the proteins. For example, proteases that exhibit reduced immunogenic responses can be used in cleaning compositions. An effective amount of one or more protease variants described herein find use in compositions useful for cleaning a variety of surfaces in need of proteinaceous stain removal. Such cleaning compositions include detergent compositions for cleaning hard surfaces, detergent compositions for cleaning fabrics, dishwashing compositions, oral cleaning compositions, and denture cleaning compositions.

An effective amount of one or more protease variants described herein may also be included in compositions to be applied to keratinous materials such as nails and hair, including but not limited to those useful as hair spray compositions, hair shampoo and/or conditioning compositions, compositions applied for the purpose of hair growth regulation, and compositions applied to the hair and scalp for the purpose of treating seborrhea, dermatitis, and/or dandruff.

An effective amount of one or more protease variant(s) described herein find use in included in compositions suitable for topical application to the skin or hair. These compositions can be in the form of creams, lotions, gels, and the like, and may be formulated as aqueous compositions or may be formulated as emulsions of one or more oil phases in an aqueous continuous phase.

Skin Care Active

In some embodiments, the compositions provided by the present invention comprise a skin care active at a level from about 0.1% to about 20%, preferably from about 1% to about 10%, more preferably from about 2% to about 8%, by weight. Non-limiting examples of suitable skin care actives for use herein include a vitamin $B_3$ component, panthenol, vitamin E, vitamin E acetate, retinol, retinyl propionate, retinyl palmitate, retinoic acid, vitamin C, theobromine, α-hydroxyacid, farnesol, phytantriol, salicylic acid, palmityl peptapeptide-3 and mixtures thereof.

B3 Compound

As used herein, "vitamin $B_3$ compound" means a compound having the formula:

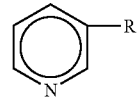

wherein R is —$CONH_2$ (i.e., niacinamide), —COOH (i.e., nicotinic acid) or —$CH_2OH$ (i.e., nicotinyl alcohol); derivatives thereof; and salts of any of the foregoing. Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide.

Suitable esters of nicotinic acid include nicotinic acid esters of $C_1$-$C_{22}$, preferably $C_1$-$C_{16}$, more preferably $C_1$-$C_6$ alcohols. The alcohols are suitably straight-chain or branched chain, cyclic or acyclic, saturated or unsaturated (including aromatic), and substituted or unsubstituted. The esters are preferably non-vasodilating. As used herein, "non-vasodilating" means that the ester does not commonly yield a visible flushing response after application to the skin in the subject compositions (i.e., the majority of the general population would not experience a visible flushing response, although such compounds may cause vasodilation not visible to the naked eye). Non-vasodilating esters of nicotinic acid include tocopherol nicotinate and inositol hexanicotinate; tocopherol nicotinate is preferred. A more complete description of vitamin $B_3$ compounds is given in WO 98/22085. Preferred vitamin $B_3$ compounds are niacinamide and tocopherol nicotinate.

Retinoids

Another suitable skin care active is a retinoid. As used herein, "retinoid" includes all natural and/or synthetic analogs of Vitamin A or retinol-like compounds which possess the biological activity of Vitamin A in the skin as well as the geometric isomers and stereoisomers of these compounds.

When a retinoid is included in the compositions herein, it typically comprises from or about 0.005% to or about 2%, more preferably 0.01% to about 2% retinoid. Retinol is preferably used in an amount of from or about 0.01% to or about 0.15%; retinol esters are preferably used in an amount of from about 0.01% to about 2% (e.g., about 1%).

The retinoid is preferably retinol, retinol esters (e.g., $C_2$-$C_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources (e.g., Sigma Chemical Company (St. Louis, Mo.), and Boehringer Mannheim (Indianapolis, Ind.)). Preferred retinoids include retinol, retinyl palmitate, retinyl acetate, retinyl propionate, retinal, retinoic acid and combinations thereof. More preferred retinoids include retinol, retinoic propionate, retinoic acid and retinyl palmitate. The retinoid may be included as the substantially pure material, or as an extract obtained by suitable physical and/or chemical isolation from natural (e.g. plant) sources.

Carriers

It is further contemplated that the compositions of the present invention will find use in safe and effective amounts of a dermatologically acceptable carrier, suitable for topical application to the skin and/or hair within which the essential materials and optional other materials are incorporated to enable the essential materials and optional components to be delivered to the skin or hair at an appropriate concentration. Thus, the carrier acts as a diluent, dispersant, solvent, or the like for the essential components which ensures that they can be applied to and distributed evenly over the selected target at an appropriate concentration.

The type of carrier utilized in the present invention depends on the type of product form desired for the composition. It is not intended that the present invention be limited to a carrier of any particular form, although it is most commonly a solid, semi-solid or liquid. Suitable carriers are liquid or semi-solid, such as creams, lotions, gels, sticks, ointments, pastes and mousses. Preferably the carrier is in the form of a lotion, cream or a gel, more preferably one which has a sufficient thickness or yield point to prevent the particles from sedimenting. The carrier can itself be inert or it can possess dermatological benefits of its own. The carrier may be applied directly to the skin and/or hair, or it may be applied via a woven or non-woven wipe or cloth. It may also be in the form of a patch, mask, or wrap. It may also be aerosolized or otherwise sprayed onto the skin and/or hair. The carrier should also be physically and chemically compatible with the essential components described herein, and should not unduly impair stability, efficacy or other use benefits associated with the compositions of the present invention.

Preferred carriers contain a dermatologically acceptable, hydrophilic diluent. Suitable hydrophilic diluents include water, organic hydrophilic diluents such as $C_1$-$C_4$ monohydric alcohols and low molecular weight glycols and polyols, including propylene glycol, polyethylene glycol (e.g. of MW 200-600), polypropylene glycol (e.g. of MW 425-2025), glycerol, butylene glycol, 1,2,4-butanetriol, sorbitol esters, 1,2,6-hexametriol, ethanol, iso-propanol, sorbitol esters, ethoxylated ethers, propoxylated ethers and combinations thereof. The diluent is preferably liquid. Water is a preferred diluent. The composition preferably comprises at least about 20% of the hydrophilic diluent.

Suitable carriers may also comprise an emulsion comprising a hydrophilic phase, especially an aqueous phase, and a hydrophobic phase (e.g., a lipid, oil or oily material). As well known to those skilled in the art, the hydrophilic phase is dispersed in the hydrophobic phase, or vice versa, to form respectively hydrophilic or hydrophobic dispersed and continuous phases, depending on the composition ingredients. In emulsion technology, the well-known term "dispersed phase" means that the phase exists as small particles or droplets that are suspended in and surrounded by a continuous phase. The dispersed phase is also known as the internal or discontinuous phase. The emulsion may be or comprise (e.g. in a triple or other multi-phase emulsion) an oil-in-water emulsion or a water-in-oil emulsion such as a water-in-silicone emulsion. Oil-in-water emulsions typically comprise from about 1% to about 60% (preferably about 1% to about 30%) of the dispersed hydrophobic phase and from about 1% to about 99% (preferably from about 40% to about 90%) of the continuous hydrophilic phase; water-in-oil emulsions typically comprise from about 1% to about 98% (preferably from about 40% to about 90%) of the dispersed hydrophilic phase and from about 1% to about 50% (preferably about 1% to about 30%) of the continuous hydrophobic phase.

Humectants

In some embodiments, the compositions of the present invention comprise humectants which are preferably present at a level of from about 0.01% to about 20%, more preferably from about 0.1% to about 15% and especially from about 0.5% to about 10%. Preferred humectants include, but are not limited to, compounds selected from polyhydric alcohols, urea, D or DL panthenol, calcium pantothenate, royal jelly, panthetine, pantotheine, panthenyl ethyl ether, pangamic acid, pyridoxin, pantoyl lactose Vitamin B complex, hexane-1,2,6,-triol, guanidine or its derivatives, and mixtures thereof.

Suitable polyhydric alcohols for use herein include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, erythritol, threitol, pentaerythritol, xylitol, glucitol, mannitol, hexylene glycol, butylene glycol (e.g., 1,3-butylene glycol), hexane triol (e.g., 1,2,6-hexanetriol), trimethylol propane, neopentyl glycol, glycerine, ethoxylated glycerine, propane-1,3 diol, propoxylated glycerine and mixtures thereof. The alkoxylated derivatives of any of the above polyhydric alcohols are also suitable for use herein. Preferred polyhydric alcohols of the present invention are selected from glycerine, butylene glycol, propylene glycol, dipropylene glycol, polyethylene glycol, hexane triol, ethoxylated glycerine and propoxylated glycerine, and mixtures thereof.

Suitable humectants useful herein are sodium 2-pyrrolidone-5-carboxylate (NaPCA), guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); hyaluronic acid and derivatives thereof (e.g., salt derivatives such as sodium hyaluronate); lactamide monoethanolamine; acetamide monoethanolamine; urea; panthenol and derivatives thereof; and mixtures thereof.

At least part (up to about 5% by weight of composition) of a humectant can be incorporated in the form of an admixture with a particulate cross-linked hydrophobic acrylate or methacrylate copolymer, itself preferably present in an amount of from about 0.1% to about 10%, which can be added either to the aqueous or disperse phase. This copolymer is particularly valuable for reducing shine and controlling oil while helping to provide effective moisturization benefits and is described in further detail by WO96/03964, incorporated herein by reference.

Emollients

In some embodiments, the oil in water emulsion embodiments of the present invention comprise from about 1% to about 20%, preferably from about 1.5% to about 15%, more preferably from about 0.1% to about 8%, and even more preferably from about 0.5% to about 5% of a dermatologically acceptable emollient. Emollients tend to lubricate the skin, increase the smoothness and suppleness, prevent or relieve dryness, and/or protect the skin. Emollients are typically water-immiscible, oily or waxy materials and emollients with high molecular weights can confer tacky properties to a topical composition. A wide variety of suitable emollients are known and may be used herein. For example, Sagarin, *Cosmetics Science and Technology*, 2nd Edition, Vol. 1, pp. 32-43 (1972), contains numerous examples of materials suitable for use as emollients. In addition, all emollients discussed in application WO 00/24372 should be considered as suitable for use in the present invention although preferred examples are outlined in further detail below:

i) Straight and branched chain hydrocarbons having from about 7 to about 40 carbon atoms, such as dodecane, squalane, cholesterol, hydrogenated polyisobutylene, isohexadecane, isoeicosane, isooctahexacontane, isohexapentacontahectane, and the $C_7$-$C_{40}$ isoparaffins, which are $C_7$-$C_{40}$ branched hydrocarbons. Suitable branched chain hydrocarbons for use herein are selected from isopentacontaoctactane, petrolatum, and mixtures thereof. Suitable for use herein are branched chain aliphatic hydrocarbons sold under the trade name Permethyl (RTM) and commercially available from Presperse Inc., South Plainfield, N.J.

ii) $C_1$-$C_{30}$ alcohol esters of $C_1$-$C_{30}$ carboxylic acids, C12-15 alkyl benzoates, and of $C_2$-$C_{30}$ dicarboxylic acids, for example, isononyl isononanoate, isostearyl neopentanoate, isodecyl octanoate, isodecyl isononanoate, tridecyl isononanoate, myristyl octanoate, octyl pelargonate, octyl isononanoate, myristyl myristate, myristyl neopentanoate, myristyl octanoate, isopropyl myristate, myristyl propionate, isopropyl stearate, isopropyl isostearate, methyl isostearate, behenyl behenate, dioctyl maleate, diisopropyl adipate, and diisopropyl dilinoleate and mixtures thereof.

iii) $C_1$-$C_{30}$ mono- and poly-esters of sugars and related materials. These esters are derived from a sugar or polyol moiety and one or more carboxylic acid moieties. Depending on the constituent acid and sugar, these esters can be in either liquid or solid form at room temperature. Examples include glucose tetraoleate, the galactose tetraesters of oleic acid, the sorbitol tetraoleate, sucrose tetraoleate, sucrose pentaoleate, sucrose hexaoleate, sucrose heptaoleate, sucrose octaoleate, sorbitol hexaester in which the carboxylic acid ester moieties are palmitoleate and arachidate in a 1:2 molar ratio, and the octaester of sucrose wherein the esterifying carboxylic acid moieties are laurate, linoleate and behenate in a 1:3:4 molar ratio. Other materials include cottonseed oil or soybean oil fatty acid esters of sucrose. Other examples of such materials are described in WO 96/16636, incorporated by reference herein. A particularly preferred material is known by the INCI name sucrose polycottonseedate.

iv) Vegetable oils and hydrogenated vegetable oils. Examples of vegetable oils and hydrogenated vegetable oils include safflower oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, partially and fully hydrogenated oils from the foregoing sources, and mixtures thereof.

v) Soluble or colloidally-soluble moisturising agents. Examples include hylaronic acid and starch-grafted sodium polyacrylates such as Sanwet (RTM) IM-1000, IM-1500 and IM-2500 available from Celanese Superabsorbent Materials, Portsmith, Va., and described in U.S. Pat. No. 4,076,663.

Preferred emollients for use herein are isohexadecane, isooctacontane, petrolatum, is isononyl isononanoate, isodecyl octanoate, isodecyl isononanoate, tridecyl isononanoate, myristyl octanoate, octyl isononanoate, myristyl myristate, methyl isostearate, isopropyl isostearate, C12-15 alkyl benzoates and mixtures thereof. Particularly preferred emollients for use herein are isohexadecane, isononyl isononanoate, methyl isostearate, isopropyl isostearate, petrolatum, or mixtures thereof.

Emulsifiers/Surfactants

In some embodiments, the compositions of the present invention contain an emulsifier and/or surfactant, generally to help disperse and suspend the disperse phase within the continuous aqueous phase. A surfactant may also be useful if the product is intended for skin cleansing. For convenience hereinafter, emulsifiers are encompassed within the term "surfactants." thus "surfactant(s)" refers to surface active agents whether used as emulsifiers or for other surfactant purposes such as skin cleansing. Known or conventional surfactants find use used in the compositions of the present invention, provided that the selected agent is chemically and physically compatible with essential components of the composition, and provides the desired characteristics. Suitable surfactants include non-silicone derived materials, and mixtures thereof. All surfactants discussed in application WO 00/24372 are considered as suitable for use in the present invention.

In some embodiments, the compositions of the present invention comprise from about 0.05% to about 15% of a surfactant or mixture of surfactants. The exact surfactant or surfactant mixture chosen will depend upon the pH of the composition and the other components present.

Among the nonionic surfactants that are useful herein are those that can be broadly defined as condensation products of long chain alcohols (e.g. $C_{8-30}$ alcohols), with sugar or starch polymers (i.e., glycosides). Other useful nonionic surfactants include the condensation products of alkylene oxides with fatty acids (i.e., alkylene oxide esters of fatty acids). These materials have the general formula $RCO(X)_n$OH wherein R is a $C_{10-30}$ alkyl group, X is —$OCH_2CH_2$— (i.e. derived from ethylene glycol or oxide) or —$OCH_2CHCH_3$— (i.e. derived from propylene glycol or oxide), and n is an integer from about 6 to about 200. Other nonionic surfactants are the condensation products of alkylene oxides with 2 moles of fatty acids (i.e., alkylene oxide diesters of fatty acids). These materials have the general formula $RCO(X)_n$OOCR wherein R is a $C_{10-30}$ alkyl group, X is —$OCH_2CH_2$— (i.e. derived from ethylene glycol or oxide) or —$OCH_2CHCH_3$— (i.e., derived from propylene glycol or oxide), and n is an integer from about 6 to about 100. An emulsifier for use herein is most preferably a fatty acid ester blend based on a mixture of sorbitan fatty acid ester and sucrose fatty acid ester, especially a blend of sorbiton stearate and sucrose cocoate. This is commercially available from ICI under the trade name Arlatone 2121. Even further suitable examples include a mixture of cetearyl alcohols, cetearyl glucosides such as those available under the trade name Montanov 68 from Seppic and Emulgade PL68/50 available from Henkel.

In some embodiments, the hydrophilic surfactants useful herein alternatively or additionally include any of a wide variety of cationic, anionic, zwitterionic, and amphoteric surfactants such as are known in the art (See e.g., U.S. Pat. No. 5,011,681, U.S. Pat. No. 4,421,769, and U.S. Pat. No. 3,755,560). A wide variety of anionic surfactants also find use in the compositions of the present invention (See e.g., U.S. Pat. No. 3,929,678). Exemplary anionic surfactants include the alkoyl isethionates (e.g., $C_{12}$-$C_{30}$), alkyl and alkyl ether sulfates and salts thereof, alkyl and alkyl ether phosphates and salts thereof, alkyl methyl taurates (e.g., $C_{12}$-$C_{30}$), and soaps (e.g., alkali metal salts, such as sodium or potassium salts) of fatty acids.

Amphoteric and zwitterionic surfactants also find use in the compositions of the present invention. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$-$C_{18}$) and one contains an anionic water solubilising group (e.g., carboxy, sulfonate, sulfate, phosphate, or phosphonate). Examples include alkyl imino acetates, iminodialkanoates and aminoalkanoates, imidazolinium and ammonium derivatives. Other suitable amphoteric and zwitterionic surfactants include those selected from the group consisting of betaines, sultaines, hydroxysultaines, and branched and unbranched alkanoyl sarcosinates, and mixtures thereof.

In some embodiments, emulsions of the present invention further include a silicone containing emulsifier or surfactant. A wide variety of silicone emulsifiers find use in the present invention. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols (i.e., compounds which contain $C_2$-$C_{30}$ pendant side chains). Still other useful dimethicone copolyols include materials having various cationic, anionic, amphoteric, and zwitterionic pendant moieties.

Polymeric Thickening Agents

In some embodiments, the compositions of the present invention comprise at least one polymeric thickening agent. The polymeric thickening agents useful herein preferably have a number average molecular weight of greater than 20,000, more preferably greater than 50,000 and especially greater than 100,000. In some embodiments, the compositions of the present invention comprise from about 0.01% to about 10%, preferably from about 0.1% to about 8% and most preferably from about 0.5% to about 5% by weight of the composition of the polymeric thickening agent, or mixtures thereof.

Preferred polymer thickening agents for use herein include non-ionic thickening agents and anionic thickening agents, or mixtures thereof. Suitable non-ionic thickening agents include polyacrylamide polymers, crosslinked poly (N-vinylpyrrolidones), polysaccharides, natural or synthetic gums, polyvinylpyrrolidone, and polyvinylalcohol. Suitable anionic thickening agents include acrylic acid/ethyl acrylate copolymers, carboxyvinyl polymers and crosslinked copolymers of alkyl vinyl ethers and maleic anhydride. Particularly preferred thickening agents for use herein are the non-ionic polyacrylamide polymers such as polyacrylamide and isoparaffin and laureth-7, available under the trade name Sepigel 305 from Seppic Corporation, and acrylic acid/ethyl acrylate copolymers and the carboxyvinyl polymers sold by the B.F. Goodrich Company under the trade mark of CARBOPOL™ resins, or mixtures thereof. In some embodiments, suitable CARBOPOL™ resins are hydrophobically modified. Additional suitable resins are described in WO98/22085. It is also contemplated that mixtures of these resins will find use in the present invention.

Silicone Oil

In some embodiments, the present compositions comprise, at least one silicone oil phase. Silicone oil phase(s) generally comprises from about 0.1% to about 20%, preferably from about 0.5% to about 10%, more preferably from about 0.5% to about 5%, of the composition. The, or each, silicone oil phase preferably comprises one or more silicone components.

In some embodiments, silicone components are fluids, including straight chain, branched and cyclic silicones. Suitable silicone fluids useful herein include silicones inclusive of polyalkyl siloxane fluids, polyaryl siloxane fluids, cyclic and linear polyalkylsiloxanes, polyalkoxylated silicones, amino and quaternary ammonium modified silicones, polyalkylaryl siloxanes or a polyether siloxane copolymer and mixtures thereof. The silicone fluids can be volatile or non-volatile. Silicone fluids generally have a weight average molecular weight of less than about 200,000. Suitable silicone fluids have a molecular weight of about 100,000 or less, preferably about 50,000 or less, most preferably about 10,000 or less. Preferably the silicone fluid is selected from silicone fluids having a weight average molecular weight in the range from about 100 to about 50,000 and preferably from about 200 to about 40,000. Typically, silicone fluids have a viscosity ranging from about 0.65 to about 600,000 $mm^2.s^{-1}$, preferably from about 0.65 to about 10,000 $mm^2.s^{-1}$ at 25° C. The viscosity can be measured by means of a glass capillary viscometer as set forth in Dow Corning Corporate Test Method CTM0004. Suitable polydimethyl siloxanes that find use in the present invention include those available, for example, from the General Electric Company as the SF and Viscasil (RTM) series and from Dow Corning as the Dow Corning 200 series. Also useful are essentially non-volatile polyalkylarylsiloxanes (e.g., polymethylphenylsiloxanes), having viscosities of about 0.65 to 30,000 $mm^2.s^{-1}$ at 25° C. These siloxanes are available, for example, from the General Electric Company as SF 1075 methyl phenyl fluid or from Dow Corning as 556 Cosmetic Grade Fluid. Cyclic polydimethylsiloxanes suitable for use herein are those having a ring structure incorporating from about 3 to about 7 $(CH_3)_2SiO$ moieties.

Silicone gums also find use with the present invention. The term "silicone gum" herein means high molecular weight silicones having a weight average molecular weight in excess of about 200,000 and preferably from about 200,000 to about 4,000,000. The present invention includes non-volatile polyalkyl as well as polyaryl siloxane gums. In preferred embodiments, a silicone oil phase comprises a silicone gum or a mixture of silicones including the silicone gum. Typically, silicone gums have a viscosity at 25° C. in excess of is about 1,000,000 $mm^2s^{-1}$. The silicone gums include dimethicones as known in the art (See e.g., U.S. Pat. No. 4,152,416), as well as the silicone gums described in General Electric Silicone Rubber Product Data Sheets SE 30, SE 33, SE 54 and SE 76. Specific examples of silicone gums include polydimethylsiloxane, (polydimethylsiloxane) (methylvinylsiloxane) copolymer, poly(dimethylsiloxane) (diphenyl)(methylvinylsiloxane) copolymer and mixtures thereof. Preferred silicone gums for use herein are silicone gums having a molecular weight of from about 200,000 to about 4,000,000 selected from dimethiconol, dimethicone copolyol, dimethicone, and mixtures thereof.

A silicone phase herein preferably comprises a silicone gum incorporated into the composition as part of a silicone gum-fluid blend. When the silicone gum is incorporated as part of a silicone gum-fluid blend, the silicone gum preferably constitutes from about 5% to about 40%, especially from about 10% to 20% by weight of the silicone gum-fluid blend. Suitable silicone gum-fluid blends herein are mixtures consisting essentially of:

(i) a silicone having a molecular weight of from about 200,000 to about 4,000,000 selected from dimethiconol, fluorosilicone and dimethicone and mixtures thereof, and (ii) a carrier which is a silicone fluid, the carrier having a viscosity from about 0.65 $mm^2.s^{-1}$ to about 100 $mm^2.s^{-1}$, wherein the ratio of i) to ii) is from about 10:90 to about 20:80 and wherein the silicone gum-based component has a final viscosity of from about 100 $mm^2.s^{-1}$ to about 100,000 $mm^{-2}.s^{-1}$, preferably from 500 $mm^2.s^{-1}$ to about 10,000 $mm^2.s^{-1}$.

Further silicone components suitable for use in a silicone oil phase herein are crosslinked polyorganosiloxane polymers, optionally dispersed in a fluid carrier. In general, crosslinked polyorganosiloxane polymers, together with its carrier (if present) comprise 0.1% to about 20%, preferably from about 0.5% to about 10%, more preferably from about 0.5% to about 5% of the composition. Such polymers comprise polyorganosiloxane polymers crosslinked by a crosslinklng agent. Suitable crosslinking agents include those described in WO98/22085. Examples of suitable polyorganosiloxane polymers for use herein include methyl vinyl dimethicone, methyl vinyl diphenyl dimethicone, and methyl vinyl phenyl methyl diphenyl dimethicone.

Another class of silicone components suitable for use in a silicone oil phase herein includes polydiorganosiloxane-polyoxyalkylene copolymers containing at least one polydiorganosiloxane segment and at least one polyoxyalkylene segment. Suitable polydiorganosiloxane segments and copolymers thereof include those described in WO98/22085. Suitable polydiorganosiloxane-polyalkylene copolymers are available commercially under the trade names Belsil (RTM) from Wacker-Chemie GmbH, Munich, and Abil (RTM) from Th. Goldschmidt Ltd., England, for example Belsil (RTM) 6031 and Abil (RTM) B88183. A particularly preferred copolymer fluid blend for use herein includes Dow Corning DC3225C which has the CTFA designation Dimethicone/Dimethicone copolyol.

Sunscreens

In still further embodiments, the present invention provides compositions comprising an organic sunscreen. In some embodiments, suitable sunscreens include UVA absorbing properties and/or UVB absorbing properties. The exact amount of the sunscreen active will vary depending upon the desired Sun Protection Factor (i.e., the "SPF") of the composition, as well as the desired level of UV protection. The compositions of the present invention preferably comprise an SPF of at least 10, preferably at least 15. SPF is a commonly used measure of photoprotection of a sunscreen against erythema. The SPF is defined as a ratio of the ultraviolet energy required to produce minimal erythema on protected skin to that required to products the same minimal erythema on unprotected skin in the same individual (See, Fed. Reg., 43, No 166, pp. 38206-38269, Aug. 25, 1978). Amounts of the sunscreen used are typically from about 2% to about 20%, more typically from about 4% to about 14%. Suitable sunscreens include, but are not limited to, those found in the Wenninger and McEwen (eds.), *CTFA International Cosmetic Ingredient Dictionary and Handbook*, $7^{th}$ edition, volume 2 pp. 1672 (The Cosmetic, Toiletry, and Fragrance Association, Inc., Washington, D.C., 1997).

In some embodiments, compositions of the present invention comprise an UVA absorbing sunscreen actives which absorb UV radiation having a wavelength of from about 320 nm to about 400 nm. Suitable UVA absorbing sunscreen actives are selected from dibenzoylmethane derivatives, anthranilate derivatives such as methylanthranilate and homomethyl, 1-N-acetylanthranilate, and mixtures thereof. Examples of dibenzoylmethane sunscreen actives are described in U.S. Pat. No. 4,387,089, as well as in Lowe and Shaath (eds), *Sunscreens: Development, Evaluation, and Regulatory Aspects*, Marcel Dekker, Inc (1990). The UVA absorbing sunscreen active is preferably present in an amount to provide broad-spectrum UVA protection either independently, or in combination with, other UV protective actives which may be present in the composition.

Suitable UVA sunscreen actives are dibenzoylmethane sunscreen actives and their derivatives. They include, but are not limited to, those selected from 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoyl-methane, 4,4'-diisopropylbenzoylmethane, 4-(1,1-dimethylethyl)-4'-methoxydiben-zoylmethane, 2-methyl-5-isopropyl-4'-methoxydibenzoylmethane, 2-methyl-5-tert-butyl-4'-methoxy-dibenzoylmethane, 2,4-dimethyl-4'-methoxydibenzoyl-methane, 2,6-dimethyl-4'-tert-butyl-4'methoxydibenzoylmethane, and mixtures thereof. Preferred dibenzoyl sunscreen actives include those selected from 4-(1,1-dimethylethyl)-4'-methoxydibenzoymethane, 4-isopropyldibenzoylmethane, and mixtures thereof. A preferred sunscreen active is 4-(1,1-dimethylethyl)-4'-methoxydibenzoylmethane.

The sunscreen active 4-(1,1-dimethylethyl)-4'-methoxydibenzoylmethane, which is also known as butyl methoxydibenzoylmethane or Avobenzone, is commercially available under the names of PARSOL® 1789 from Givaudan Roure (International) S. A. (Basel, Switzerland) and EUSOLEX® 9020 from Merck & Co., Inc (Whitehouse Station, N.J.). The sunscreen 4-isoproplydibenzoylmethane, which is also known as isopropyldibenzoylmethane, is commercially available from Merck under the name of EUSOLEX® 8020.

In further embodiments, the compositions of the present invention comprise a UVB sunscreen active which absorbs UV radiation having a wavelength of from about 290 nm to about 320 nm. The compositions comprise an amount of the UVB sunscreen active compound which is safe and effective to provide UVB protection either independently, or in combination with, other UV protective actives which may be present in the compositions. In some embodiments, the compositions comprise from about 0.1% to abut 16%, more preferably from about 0.1% to about 12%, and most preferably from about 0.5% to about 8% by weight, of UVB absorbing organic sunscreen.

A variety of UVB sunscreen actives are suitable for use herein. Nonlimiting examples of such organic sunscreen actives include those described in U.S. Pat. No. 5,087,372, U.S. Pat. No. 5,073,371, U.S. Pat. No. 5,073,372, and Segarin et al., Cosmetics Science and Technology, at Chapter VIII, pages 189 et seq. Additional useful sunscreens include those described in U.S. Pat. No. 4,937,370, and U.S. Pat. No. 4,999,186. Preferred UVB sunscreen actives are selected from 2-ethylhexyl-2-cyano-3,2-ethylhexyl N,N-dimethyl-p-aminobenzoate, p-aminobenzoic acid, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene)camphor, 3-diphenylacrylate (referred to as octocrylene), 2-phenyl-benzimidazole-5-sulphonic acid (PBSA), cinnamates and their derivatives such as 2-ethylhexyl-p-methoxycinnamate and octyl-p-methoxycinnamate, TEA salicylate, octyldimethyl PABA, camphor derivatives and their derivatives, and mixtures thereof. Preferred organic sunscreen actives are 2-ethylhexyl-2-cyano-3,3-diphenylacrylate (referred to as octocrylene), 2-phenyl-benzimidazole-5-sulphonic acid (PBSA), octyl-p-methoxycinnamate, and mixtures thereof. Salt and acid neutralized forms of the acidic sunscreens are also useful herein.

In some embodiments of the present invention, the compositions further include an agent useful in stabilizing the UVA sunscreen to prevent it from photo-degrading on exposure to UV radiation and thereby maintaining its UVA protection efficacy. A wide range of compounds have been cited as providing these stabilizing properties. It is contemplated that these compounds are chosen to complement both the UVA sunscreen and the composition as a whole. Suitable stabilizing agents include, but are not limited to, those described in U.S. Pat. Nos. 5,972,316; 5,968,485; 5,935,556; 5,827,508 and WO 00/06110. Preferred examples of stabilizing agents for use in the present invention include 2-ethylhexyl-2-cyano-3,3-diphenylacrylate (referred to as octocrylene), ethyl-2-cyano-3,3-diphenylacrylate, 2-ethylhexyl-3,3-diphenylacrylate, ethyl-3,3-bis(4-methoxyphenyl)acrylate, and mixtures thereof. 2-ethylhexyl-2-cyano-3,3-diphenylacrylate is most preferred.

In some embodiments, an agent is added to any of the compositions useful in the present invention to improve the skin, particularly those compositions with enhanced resistance to being washed off by water, or rubbed off. A preferred agent which provides this benefit is a copolymer of ethylene and acrylic acid (See e.g., U.S. Pat. No. 4,663,157).

In addition to the organic sunscreens, in some embodiments, the compositions of the present invention additionally comprise inorganic physical sunblocks. Nonlimiting examples of suitable physical sunblocks are described in CTFA International Cosmetic Ingredient Dictionary, 6$^{th}$ Edition, 1995, pp. 1026-28 and 1103; and Sayre et al., J. Soc. Cosmet. Chem., 41:103-109 (1990). Preferred inorganic physical sunblocks include zinc oxide and titanium dioxide, and mixtures thereof.

When used, the physical sunblocks are present in an amount such that the present compositions are transparent on the skin (i.e., non-whitening), preferably less than or equal to about 5%. When titanium dioxide is used, it can have an anatase, rutile, or amorphous structure. Physical sunblock particles (e.g., titanium dioxide and zinc oxide), can be uncoated or coated with a variety of materials including but not limited to amino acids, aluminum compounds such as alumina, aluminum stearate, aluminum laurate, and the like; carboxylic acids and their salts egg stearic acid and its salts; phospholipids such as lecithin; organic silicone compounds; inorganic silicone compounds such as silica and silicates; and mixtures thereof. A preferred titanium dioxide is commercially available from Tayca (Japan) and is distributed by Tri-K Industries (Emerson, N.J.) under the MT micro-ionized series (e.g., MT 100SAS). In some embodiments, the compositions of the present invention comprise from about 0.1% to about 10%, more preferably from about 0.1% to about 4%, and most preferably from about 0.5% to about 2.5%, by weight, of inorganic sunscreen.

Antimicrobial and Antifungal Actives

In some embodiments, the compositions of the present invention comprise antimicrobial and/or antifungal actives. Non-limiting examples of antimicrobial and antifungal actives useful herein include, but are not limited to β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, clotrimazole, cetylpyridinium chloride (CPC), piroctone olamine, selenium sulfide, ketoconazole, triclocarbon, triclosan, zinc pyrithione, itraconazole, asiatic acid, hinokitiol, mipirocin, clinacycin hydrochloride, benzoyl peroxide, benzyl peroxide, minocyclin, phenoxy isopropanol, and mixtures thereof, as well as those described in EP 0 680 745.

Other Optional Ingredients

In some additional embodiments, a variety of optional ingredients such as neutralizing agents, perfumes, and coloring agents, find use in the compositions of the present invention. It is preferred that any additional ingredients enhance the skin softness/smoothness benefits of the product. In addition it is preferred that any such ingredients do not negatively impact the aesthetic properties of the product. Thus, high levels of proteins such as collagen and elastin are typically not preferred in compositions useful in the present invention.

In some embodiments, the compositions of the present invention also contain from about 0.01% to about 10%, preferably from about 0.1% to about 5% of a panthenol moisturizer. In preferred embodiments, the panthenol moisturizer is selected from D-panthenol ([R]-2,4dihydroxy-N-[3-hydroxypropyl)]-3,3-dimethylbutamide), DL-panthenol, calcium pantothenate, royal jelly, panthetine, pantotheine, panthenyl ethyl ether, pangamic acid, pyridoxin, and pantoyl lactose.

Neutralizing agents suitable for use in neutralizing acidic group containing hydrophilic gelling agents herein include sodium hydroxide, potassium hydroxide, ammonium hydroxide, monoethanolamine, triethanolamine, amino methyl propanol, tris-buffer and triethanolamine.

Other optional materials include keratolytic agents; water-soluble or solubilizable preservatives preferably at a level of from about 0.1% to about 5%, such as Germall 115, methyl, ethyl, propyl and butyl esters of hydroxybenzoic acid, benzyl alcohol, DMDM hydantoin iodopropanyl butylcarbanate available under the trade name Glydant Plus from Lonza, EDTA, Euxyl (RTM) K400, Bromopol (2-bromo-2-nitropropane-1,3-diol) and phenoxypropanol; anti-bacterials such as Irgasan (RTM) and phenoxyethanol (preferably at levels of from 0.1% to about 5%); soluble or colloidally-soluble moisturising agents such as hylaronic acid and starch-grafted sodium polyacrylates such as Sanwet (RTM) IM-1000, IM-1500 and IM-2500 available from Celanese Superabsorbent Materials, Portsmith, Va., and described in U.S. Pat. No. 4,076,663; vitamins such as vitamin A, vitamin C, vitamin E and derivatives thereof and building blocks thereof such as phytantriol and vitamin K and components thereof such as the fatty alcohol dodecatrienol; alpha and beta hydroxyacids; aloe vera; sphingosines and phytosphingosines, cholesterol; skin whitening agents; N-acetyl cysteine; coloring agents; antibacterial agents such as TCC/TCS, also known as triclosan and trichlorocarbon; perfumes and perfume solubilizers. Examples of alpha hydroxy acids include glycolic acid, lactic acid, malic acid, citric acid, glycolic acid in conjunction with ammonium glycolate, alpha-hydroxy ethanoic acid, alpha-hydroxyoctanoic acid, alpha-hydroxycaprylic acid, hydroxycaprylic acid, mixed fruit acid, tri-alpha hydroxy fruit acids, triple fruit acid, sugar cane extract, alpha hydroxy and botanicals, such as those comprising 1-alpha hydroxy acid and glycomer in crosslinked fatty acids alpha nutrium. Preferred examples of alpha hydroxy acids are glycolic acid and lactic acid. It is preferred that alpha hydroxy acids are used in levels of up to 10%.

In some embodiments, a safe and effective amount of an anti-inflammatory agent is added to the compositions of the present invention, preferably from about 0.1% to about 5%, more preferably from about 0.1% to about 2%, of the composition. The anti-inflammatory agent enhances the skin appearance benefits of the present invention (e.g., such agents contribute to a more uniform and acceptable skin tone or colour). The exact amount of anti-inflammatory agent to be used in the compositions will depend on the particular anti-inflammatory agent utilized since such agents vary widely in potency.

In further embodiments, compositions of the present invention further include an anti-oxidant/radical scavenger. The anti-oxidant/radical scavenger is especially useful for providing protection against UV radiation which can cause increased scaling or texture changes in the stratum corneum and against other environmental agents which can cause skin damage. Suitable amounts are from about 0.1% to about 10%, more preferably from about 1% to about 5%, of the composition. Anti-oxidants/radical scavengers include compounds such as ascorbic acid (vitamin C) and its salts.

The inclusion of a chelating agent in some embodiments of the present invention, is especially useful for providing protection against UV radiation which can contribute to excessive scaling or skin texture changes and against other environmental agents which can cause skin damage. A suitable amount is from about 0.01% to about 1%, more preferably from about 0.05% to about 0.5%, of the composition. Exemplary chelators that are useful herein include those described in U.S. Pat. No. 5,487,884. Preferred chelators useful in compositions of the subject invention include ethylenediamine tetraacetic acid (EDTA), furildioxime, and derivatives thereof.

In still further embodiments, the compositions of the present invention also comprise a skin lightening agent. When used, the compositions preferably comprise from about 0.1% to about 10%, more preferably from about 0.2% to about 5%, also preferably from about 0.5% to about 2%, of a skin lightening agent Suitable skin lightening agents include those known in the art, including kojic acid, arbutin, ascorbic acid and derivatives thereof (e.g., magnesium ascorbyl phosphate). Further skin lightening agents suitable for use herein also include those described in WO 95/34280 and WO 95/23780; each incorporated herein by reference.

Other optional materials include water-soluble or solubilizable preservatives preferably at a level of from about 0.1% to about 5%, such as Germall 115, methyl, ethyl, propyl and butyl esters of hydroxybenzoic acid, benzyl alcohol, DMDM hydantoin iodopropanyl butylcarbanate available under the trade name Glydant Plus (Lonza), EDTA, Euxyl (RTM) K400, Bromopol (2-bromo-2-nitropropane-1,3-diol) and phenoxypropanol; anti-bacterials such as Irgasan (RTM) and phenoxyethanol (preferably at levels of from 0.1% to about 5%). Antibacterial agents such as TCC/TCS, also known as triclosan and trichlorocarbon are also useful in compositions of the present invention.

Other optional materials herein include pigments which, when water-insoluble, contribute to and are included in the total level of oil phase ingredients. Pigments suitable for use in the compositions of the present invention can be organic and/or inorganic. Also included within the term "pigment" are materials having a low colour or luster such as matte finishing agents, and also light scattering agents. Preferably, the compositions of the present invention comprise particulate materials having a refractive index of from about 1.3 to about 1.7, the particulate materials being dispersed in the composition and having a median particle size of from about 2 to about 30 µm. Preferably the particulates useful herein have relatively narrow distributions, by which is meant that more than 50% of the particles fall within 3 µm either side of the respective median value. It is also preferred that more than 50%, preferably more than 60%, and even more preferably more than 70% of particles fall within the size ranges prescribed for the respective median values. Suitable particulate materials include organic or organosilicone and preferably organosilicone polymers. Preferred particles are free-flowing, solid, materials. By "solid" is meant that the particles are not hollow. The void at the center of hollow particles can have an adverse effect on refractive index and therefore the visual effects of the particles on either skin or the composition. Suitable organic particulate materials include those made of polymethylsilsesquioxane, referenced above, polyamide, polythene, polyacrylonitrile, polyacrylic acid, polymethacrylic acid, polystyrene, polytetrafluoroethylene (PTFE) and poly(vinylidene chloride). Copolymers derived from monomers of the aforementioned materials can also be used. Inorganic materials include silica and boron nitride. Representative commercially available examples of useful particulate materials herein are Tospearl® 145 which has a median particle size of about 4.5 µm and EA-209® from Kobo which is an ethylene/acrylic acid copolymer having a median particle size of about 10 µm, Nylon-12 available under the trade name Orgasol 2002 from Elf Atochem, France, or mixtures thereof.

Further examples of suitable pigments include titanium dioxide, predispersed titanium dioxide from Kobo (e.g., Kobo GWL75CAP), iron oxides, acyglutamate iron oxides, ultramarine blue, D&C dyes, carmine, and mixtures thereof. Depending upon the type of composition, a mixture of pigments will often find use. The preferred pigments for use herein from the viewpoint of moisturisation, skin feel, skin appearance and emulsion compatibility are treated pigments. The pigments can be treated with compounds such as amino acids, silicones, lecithin and ester oils.

Suitably, the pH of the compositions herein is in the range from about 6.1 to about 10.0, wherein the pH of the final composition is adjusted by addition of acidic, basic or buffer salts as necessary.

Preparation of Compositions

The compositions of the present invention are prepared by standard techniques well known to those skilled in the art. In general, the aqueous phase and/or the oil phase are prepared separately, with materials of similar phase partitioning being added in any order. If the final product is an emulsion, the two phases are then combined with vigorous stirring. Any ingredients in the formulation with high volatility, or which are susceptible to hydrolysis at high temperatures, can be added with gentle stirring towards the end of the process, post emulsification if applicable.

Proteases with reduced allergenicity also find use in the treatment of textiles. "Textile treatment" comprises a process wherein textiles, individual yarns or fibers that can be woven, felted or knitted into textiles or garments are treated to produce a desired characteristic. Examples of such desired characteristics are "stone-washing," depilling, dehairing, desizing, softening, and other textile treatments well known to those of skill in the art.

In one embodiment of the present invention, the epitopes identified herein are used to elicit an immune response (e.g., where it is desired to raise antibodies against a protease including one or both of such epitopes. Such antibodies find use in screening for other proteases that include one or both of these regions, or regions highly homologous thereto. Accordingly, the present invention provides a protease including one or both of the following sequences: (i) residues 70-84 and/or (ii) residues 109-123 of *Bacillus amyloliquefaciens* subtilisin. The present invention can be embodied in immunoassays utilizing isolated natural epitope, recombinant protein, or synthetic peptide representing specific epitopic regions to evaluate persons for sensitization to proteins including these or highly homologous regions.

In another embodiment, the epitopic fragments herein are used in the detection of antigen presenting cells having MHC molecules capable of binding and displaying such fragments. For example, the epitopic fragments can include a detectable label (e.g., radiolabel). The labeled fragments are then be incubated with cells of interest, and then cells which bind (or display) the labeled fragments are detected.

All publications and patents referenced herein are hereby incorporated by reference in their entirety. The following is presented by way of example and is not to be construed as a limitation to the scope of the claims.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); kg (kilograms); µg (micrograms); L (liters); ml (milliliters); µl (microliters); cm (centimeters); mm (millimeters); µm (micrometers); nm (nanometers); ° C. (degrees Centigrade); h (hours); min (minutes); sec (seconds); msec (milliseconds); xg (times gravity); Ci (Curies); OD (optical density); Dulbecco's phosphate buffered solution (DPBS); HEPES (N-[2-Hydroxyethyl]piperazine-N-[2-ethanesulfonic acid]); HBS (HEPES buffered saline); SDS (sodium dodecylsulfate); Tris-HCl (tris[Hydroxymethyl]aminomethane-hydrochloride); Klenow (DNA polymerase I large (Klenow) fragment); rpm (revolutions per minute); EGTA (ethylene glycol-bis(β-aminoethyl ether) N,N,N',N'-tetraacetic acid); EDTA (ethylenediamine tetracetic acid); ATCC (American Type Culture Collection, Rockville, Md.); Cedar Lane (Cedar Lane Laboratories, Ontario, Canada); Gibco/BRL (Gibco/BRL, Grand Island, N.Y.); Sigma (Sigma Chemical Co., St. Louis, Mo.); Pharmacia (Pharmacia Biotech, Piscataway, N.J.); Procter & Gamble (Procter and Gamble, Cincinnati, Ohio); and Stratagene (Stratagene, La Jolla, Calif.).

Example 1

Assay for the Identification of Peptide T-Cell Epitopes Using Naïve Human T-Cells Fresh human peripheral blood cells were collected from "naïve humans" (i.e., persons not known to be exposed to or sensitized to *B. lentus* protease), for determination of antigenic epitopes in protease from *B. lentus* and human subtilisin. "Naïve humans" are intended to mean that the individuals are not known to have been exposed to or developed a reaction to protease in the past. Peripheral mononuclear blood cells (stored at room temperature, no older than 24 hours) were prepared for use as follows: Approximately 30 mls of a solution of buffy coat preparation from one unit of whole blood was brought to 50 ml with Dulbecco's phosphate buffered solution (DPBS) and split into two tubes. The samples were underlaid with 12.5 ml of room temperature lymphoprep density separation media (Nycomed density 1.077 g/ml). The tubes were centrifuged for thirty minutes at 600×g. The interface of the two phases was collected, pooled and washed in DPBS. The cell density of the resultant solution was measured by hemocytometer. Viability was measured by trypan blue exclusion.

From the resulting solution, a differentiated dendritic cell culture was prepared from the peripheral blood mononuclear cell sample having a density of $10^8$ cells per 75 ml culture flask in a solution as follows:

(1) 50 ml of serum free AIM V media (Gibco) was supplemented with a 1:100 dilution beta-mercaptoethanol (Gibco). The flasks were laid flat for two hours at 37° C. in 5% $CO_2$ to allow adherence of monocytes to the flask wall.

(2) Differentiation of the monocyte cells to dendritic cells was as follows: nonadherent cells were removed and the resultant adherent cells (monocytes) combined with 30 ml of AIM V, 800 units/ml of GM-CSF (Endogen) and 500 units/ml of IL-4 (Endogen); the resulting mixture was cultured for 5 days under conditions at 37° C. in 5% $CO_2$. After five days, the cytokine TNFa (Endogen) was added to 0.2 units/ml, and the cytokine IL-1a (Endogen) was added to a final concentration of 50 units/ml and the mixture incubated at 37° C. in 5% $CO_2$ for two more days.

(3) On the seventh day, mitomycin C was added to a concentration of 50 microgram/ml was added to stop growth of the now differentiated dendritic cell culture. The solution was incubated for 60 minutes at 37° C. in 5% $CO_2$. Dendritic cells were collected by gently scraping the adherent cells off the bottom of the flask with a cell scraper. Adherent and non-adherent cells were then centrifuged at 600 G for 5 minutes, washed in DPBS and counted.

(4) The prepared dendritic cells were placed into a 96 well round bottom array at $2 \times 10^4$/well in 100 microliter total volume of AIM V media.

CD4+ T-cells were prepared from frozen aliquots of the peripheral blood cell samples used to prepare the dendritic cells using the human CD4+ Cellect Kit (Cedar Lane) as per the manufacturers instructions with the following modifications: the aliquots were thawed and washed such that approximately 108 cells will be applied per Cellect column; the cells were resuspended in 4 ml DPBS and 1 ml of the Cell reagent from the Cellect Kit, the solution maintained at room temperature for 20 minutes. The resultant solution was centrifuged for five minutes at 600 G at room temperature and the pellet resuspended in 2 ml of DPBS and applied to the Cellect columns. The effluent from the columns was collected in 2% human serum in DPBS. The resultant CD4+ cell solution was centrifuged, resuspended in AIMV media and the density counted.

The CD4+ T-cell suspension was resuspended to a count of $2 \times 10^6$/ml in AIM V media to facilitate efficient manipulation of the 96 well plate.

Peptide antigen is prepared from a 1M stock solution in DMSO by dilution in AIM V media at a 1:10 ratio. 10 microliters of the stock solution is placed in each well of the 96 well plate containing the differentiated dendritic cells. 100 microliter of the diluted CD4+ T-cell solution as prepared above is further added to each well. Useful controls include diluted DMSO blanks, and tetanus toxoid positive controls.

The final concentrations in each well, at 210 microliter total volume are as follows:
$2 \times 10^4$ CD4+
$2 \times 10^5$ dendritic cells (R:S of 10:1)
5 µM peptide Example 2

Testing for Reduced Allergenicity in Protease Variants by Whole Enzyme/Human Cell In Vitro Proliferation Assay This assay is useful to test in vitro proliferative responses by human peripheral blood mononuclear cells (PBMC) to a peptide of interest (P1) and its variants. In some embodiments, P1 and the enzyme variants are inactivated by treatment with phenyl methyl sulfonyl fluoride ("PMSF"). Human PBMC are cultured with increasing doses of inactivated P1. The variants are tested in this manner to determine the PBMC proliferative response to the variants.

Proliferation in response to P1 indicates that the whole molecule has been processed and presented to B-cells by the antigen-presenting cells in the PBMC population. A lack of proliferation to the variants could indicate where amino acid modifications have successfully inhibited the processing, presentation and/or B-cell recognition of the P1 epitopes.

Human buffy coat samples are obtained from community sources (e.g., the Stanford University Blood Center (Palo Alto, Calif.)). PBMC are isolated by density separation, washed in DPBS and counted.

P1 and its variants are inactivated by PMSF by adding 1100 mM PMSF in 100% ethanol to a 2 mg/ml solution of the enzymes in Dulbecco's phosphate buffered saline ("DPBS") at a 1:50 dilution. The mixture is then vortexed and allowed to stand at room temperature for 5 minutes. The PMSF can be added again at a 1:50 dilution, and allowed to stand another 5 minutes. If desired, PMSF can be added a third time, allowed to stand an additional 5 minutes and residual enzyme activity assessed on the colorimetric substrate succinyl-Ala-Ala-Pro-Phe-para-nitroanilide assay as known in the art.

PBMC are resuspended at a concentration of $2 \times 10^6$ cells/ml in 5% human AB-sera in RPMI 1640 (containing penicillin, streptomycin and glutamine). Cells are plated at 2 mls/well in 24 well plates, and enzymes added. Each donor is tested with P1, and as many of the variants as can be tested (cell number limitations). Enzyme concentrations suitable for use throughout most of these studies include 1, 5 10 and 20 ug/ml. The experiments can also be performed with an extended dose range of 5, 10, 20 and 40 ug/ml enzyme. However, for consistency the data compiled here are based on the top dose of 20 ug/ml. Cultures are incubated at 37° C., 5% $CO_2$ for 5 days. On day 5, the cultures are then resuspended by pipetting, and 100 ul replicates from each well are transferred to 96 well plates. The wells are pulsed with tritiated thymidine (0.5 uCi/well) and incubation allowed to proceed for 6 hours at 37° C. The plates are then harvested, and incorporated counts determined.

Between 30 and 40 individuals are typically tested for their responses to P1. A result is determined to be positive ("yes") if there was a stimulation index (S.I.) of greater than or equal to 2.0 at the higher doses. A response is considered "weak," if it displays an S.I. less than 2.0, but above the background. The percentage of all the donors tested which mounted a proliferative response to P1 with an S.I. of 2.0 or better is then ascertained.

All variants demonstrating a reduced immunogenic response would induce a lower percent of responders. It is contemplated that the variants include at least one amino acid change to a specific amino acid selected from the at least one of the epitopic regions, 25-39, 88-102, 154-168, 160-174, 163-177 and/or 181-195 regions would show an altered immunogenic response. If a few donors responded to each of the variants, this suggests that the variants could be processed and presented by antigen-presenting cells in the cultures. However, responses to the variants could be lower than to the parent protease (e.g., the parent molecule P1), when a reduced immunogenic variant is determined.

Example 3

Determination of Specific Altered Allergenicity Residue Within an Epitope

Peptide variants based on the different epitopic sequences of P1, for example at amino acid positions 25-39, a first epitope region, 88-102, a second epitope region, 154-168, a third epitope region, 160-174, a fourth epitope region, 163-177, a fifth epitope region and/or 181-195, a sixth epitope region, corresponding to BPN' are tested as described above, using samples obtained from 20 community donor blood samples. A set of peptides is constructed (e.g., using any suitable commercial vendor). For each of the peptide variants, three amino acid offset 15-mers can be constructed to cover the entire region of the proposed change. This is done to ensure that a new T cell epitopes in another 3-mer "reading frame" when the variant is incorporated into a low allergenic protease. The parent peptides in the set can be analyzed by mass to ascertain the percentage amount of intact 15-mer.

The peptide sequences were as follows:

| Peptide | | |
|---|---|---|
| 25-39 | NVKVAVIDSGIDSSH | (SEQ ID NO:4) |
| 88-102 | ASLYAVKVLGADGSG | (SEQ ID NO:5) |
| 154-168 | GNEGTSGSSSTVGYP | (SEQ ID NO:6) |
| 160-174 | GSSSTVGYPGKYPSV | (SEQ ID NO:7) |
| 163-177 | STVGYPGKYPSVIAV | (SEQ ID NO:8) |
| 181-195 | DSSNQRASFSSVGPE | (SEQ ID NO:9) |

The three-mer offsets across each region are not shown for clarity.

Twenty blood samples are used to test peptide variants. Peptides are tested at 5 uM. Each cohort is examined to determine the percentage of donors responding to the particular epitopic region (e.g. 25-39, 88-102, 154-168, 160-174, 163-177 and/or 181-195). Variants exhibiting an altered immunogenic response are contemplated to induce fewer responses.

Determination of Specific Altered Allergenicity Residue Within an Epitope

A set of a same amino acid (e.g., glycine or alanine) substituted peptides describing the each region are tested in the standard priming assay procedure (See, Stickler et al., J. Immunother., 23:654-660 [2000]). For example, an alanine substituted peptides subset is used, with each member having a single alanine substituted residue in each non-alanine wild-type residue. The non-responders for each peptide can then be determined.

A number of community donors, for example twenty, are tested. The Stimulation Index of each individuals is examined to determine if any Stimulation Indices ["SI"] of 3 or more are obtained, which would be consistent with a low percent of naïve responders to that particular region. In order to make a more robust assessment of anchor residues, the data for all individuals whose SI response to the control peptide is 2 or better can also be compiled. From this data, the change at a particular position is ascertained as being suitable to reduce immunogenicity, as none of the non-responders would mount a response to this change and all responders with an SI of 2 or better to the control peptide would exhibit reduced proliferation to this changed peptide. The amino acid change at that particular peptide can also be correlated with the BPN' sequence residue number to identify a particularly beneficial substitution for reducing allergenicity/immunogenicity. This sequence is then be specified as the wild-type with that particular substitution or deletion, for example, a substitution at peptide #2 of pepset 25-39 would result in a pepset sequence of: NGKVAVIDSGIDSSH (SEQ ID NO:10).

In addition, the response data could indicate that a change at a particular position, e.g., 26, is best for increasing the immunogenic response depending upon the number of responders and their respective SI values which may indicate increased proliferation to this changed peptide. The amino acid change in peptide #2 is designated V26A and would be this sequence: NAKVAVIDSGIDSSH (SEQ ID NO:11).

Example 4

Reduction of Allergenicity In Vivo HLA-DR3/DQ2 Mouse T-Cell Responses to P1

In this Example, experiments utilizing a transgenic mouse model are described. The HLA-DR3/DQ2 transgene was bred onto an MHC class II knockout (C2D) background to create the mice useful in this study (Cosgrove et al., Cell 66:1051-66 [1991]). Both male and female mice are suitable for use. Animals ranging in age from one year to 6-8 weeks are useful in this regard. All animals can be as bred and maintained in the Aviron Animal Facility (Mountain View, Calif.), an AALAC accredited facility. Animals are assessed by flow cytometry and to ascertain if they express high levels of HLA-DR, and low levels of HLA-DQ using two different anti-HLA-DQ antibody reagents. It is contemplated that females express overall higher levels of HLA molecules than males. Animals are immunized by any suitable routes, including footpad immunizations in complete Freund's adjuvant (CFA), intraperitoneal immunization in CFA, and intraperitoneal immunization with P1 precipitated on alum. In some experiments, the animals are immunized by multiple routes.

To verify that the HLA-DR3/DQ2 mice are processing and presenting the particular epitopic regions from intact P1 enzyme, the splenocyte responses are epitope mapped in P1 immunized mice. Female and male mice are typically immunized three times with 10 ug of P1 in alum, on days 1, 3 and 10. The spleens are then removed on day 15. Splenocytes from the female mice are then placed in vitro at $10^6$ cells per well with 50 ug/ml of P1 peptides. Splenocytes from a number of male mice (e.g., 5), are pooled, and duplicate cultures are set up as described for the female mouse splenocytes. The cultures are then pulsed with 0.5 uCi tritiated thymidine at 24 hours, and harvested at 48 hours. The counts for replicate cultures are averaged, and the background subtracted. The background counts for each culture are determined ±cpm for the female HLA-Dr3/DQ2 P1 in alum and for the male HLA-DR3/DQ2 P1 in alum. The female mice response to 20 ug/ml of PMSF inactivated P1 in culture in SI are determined, as well as the male splenocytes. Responses to other levels of PHA (e.g., 10 ug/ml), are determined in terms of SI values to indicate appropriate cell culture condition.

Both groups of mice (male and female described above) mount a noticeable response to the those peptide fragments that display an altered immunogenic response (e.g. 25-39, 88-102, 154-168, 160-174, 163-177 and/or 181-195 peptides).

Example 5

Construction of Low Allergenic Stable Protease Variants

After determining the location of a B-cell epitope, protease variants can be constructed using established protein engineering techniques. The variants are constructed so that a highly allergenic/immunogenic amino acid sequence of a protein is replaced with a corresponding sequence from a less allergenic/immunogenic homolog. In this instance, various residues are substituted in a *B. amyloliquefaciens* mutant subtilisin (P1). The manufacture of protease P1 is described in U.S. Reissue Pat. No. RE 34,606, European patent 130,756 and U.S. Pat. No. 5,441,882. The variant P1 gene and chloramphenicol marker gene are flanked by a repeated sequence corresponding to sequence 5' to the aprE locus for amplifying copy number by using chloramphenicol selection.

Protease variants are introduced into P1 (BPN'-Y217L) by converting an amino acid selected from 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 86, 87, 88, 89, 90, 91, 92, 93, 94, 95, 96, 97, 98, 99, 100, 126, 127, 128, 129, 130, 131, 132, 133, 134, 135, 136, 137, 138, 139, 140, 166, 167, 168, 169, 170, 171, 172, 173, 174, 175, 176, 177, 178, 179, 180, 206, 207, 208, 209, 210, 211, 212, 213, 214, 215, 216, 217, 218, 219, 220, 221, 222, 223, 224, 225, 246, 247, 248, 249, 250, 251, 252, 253, 254, 255, 256, 257, 258, 259 and 260 to an alanine by site-directed mutagenesis in a pBluescript based vector unless alanine was the wild-type residue.

In the resulting plasmid, a sequence 5' to the aprE locus is repeated after the chloramphenicol gene for amplifying gene copy number by using increasing chloramphenicol concentrations. The plasmid is then transformed into a *Bacillus* production stain using a standard transformation procedure known in the art. Transformants are selected on LA plates containing 5 µg/ml chloramphenicol. The transformants are grown and subcultured in LB media with increasing levels of chloramphenicol to amplify the copy number of the particular protease variant on the chromosome. After amplification of the particular protease variant strains to 25 µg/ml chloramphenicol, the particular protease variant transformants are plated on LA+25 µg/ml chloramphenicol containing 1% skim milk and assayed for the presence of halos which are indicative of protease activity.

Example 6

Lower Allergenicity Protease Stabilizing Mutations (N76D, I79A, I122A, N218S, Q206L, P40Q, D41A, H238Y)

As described in this Example, variants can be made so as to increase stability by site-directed mutations. Each protease variant is introduced into P1 by replacing the respective residues as desired (e.g., N76 is replaced with an aspartic acid residue, I79 is replaced with an alanine residue, I122 is replaced with an alanine residue, Q206 is replaced with a lysine residue, N218 is replaced with a serine residue, P40 is replaced with a glutamine residue, D41 is replace with an alanine residue, and H238 is replaced with a tyrosine residue) by site-directed mutagenesis in a pBluescript based vector to create the respective stabilized protease variant. Each stabilized protease variant is transformed into the *Bacillus* production strain and amplified as described above and plated on slim milk plates to observe the production of proteolytic activity.

Example 7

Hydrolysis of Dimethyl Casein ("DMC") by Mutant Variant Subtilisin

Mutant variant subtilisins, isolated and purified by the methods described herein, are analyzed for their ability to hydrolyze a commercial synthetic substrate, di-methyl casein (Sigma C-9801). A 5 mg/ml DMC substrate solution is prepared in the appropriate buffer (5 mg/ml DMC, 0.005% (w/w) Tween 80® (polyoxyethylene sorbitan mono-oleate, Sigma P-1754)). Appropriate DMC substrate buffers are prepared (e.g. 50 mM sodium acetate for pH 5.5; 50 mM N-tris(hydroxymethyl)methyl-2-aminoethane sulfonic acid ("TES") for pH 6.5; 50 mM piperazine-N-N'-bis-2-ethane sulfonic acid ("PIPES") for pH 7.5; and 50 mM Tris for pH 8.5). To begin testing, 200 µl of the desired pH substrate are placed into the wells of a microtiter plate (e.g., a 96 well plate) and pre-incubated at 37° C. for twenty minutes prior to enzyme addition. A 2,4,6-trinitrobenzene sulfonate salt ("TNBS") color reaction method is used to determine activity on a Spectra Max 250 spectrophotometer. This assay measures the enzymatic hydrolysis of DMC into peptides containing free amino groups. These amino groups react with 2,4,6-trinitro-benzene sulfonic acid to form a yellow colored complex.

Thus, the more deeply colored the reaction, the more activity is measured. The TNBS detection assay can be performed on the supernatant after two hours of incubation at 37° C. A 1 mg/ml solution of TNBS is prepared in a solution containing 2.4 g NaOH, 45.4 g $Na_2B_4)_7.10H_2O$ dissolved by heating in 1000 ml. From this solution, 60 µl are aliquoted into a 96-well microtiter plate. Then, 10 µl of the incubated enzyme solution described above is added to each well and mixed for 20 minutes at room temperature. Then, 20 µl of $NaH_2PO_4$ solution (70.4 g $NaH_2PO_4.H_2O$ and 1.2 g $Na_2SO_3$ in 2000 ml) are mixed for 1 minute in the wells to stop the reaction and the absorbance at 405 nm in a SpectraMax 250 spectrophotometer is determined. A blank (same TNBS solution, but without the enzyme) is also be prepared and tested. The hydrolysis is measured by the following formula:

$$Absorbance_{405} \text{ (Enzyme solution)} - Absorbance_{405} \text{ (without enzyme)}$$

at varying enzyme concentrations (0, 2.5, 5, 7.5, and 10 ppm). The comparative ability of the mutant variants to hydrolyze such substrate versus proteases from a known mutant variant (P1) can be determined in this manner.

Example 8

Hydrolysis of Collagen, Elastin, and Keratin by Variant Proteases

Mutant variant subtilisin, isolated and purified by the methods described above, can be analyzed for their ability to hydrolyze commercial substrates, for example bovine collagen (Sigma C-9879), bovine elastin (Sigma E-1625), and/or bovine keratin (ICN Biomedical 902111). A 5 mg/ml substrate solution is prepared (in 0.005% Tween 80®). Each substrate is prepared in the appropriate pH as known in the art (e.g., pH 5.5, 6.5, 7.5, and 8.5). To test, 1.5 ml of the each substrate is transferred into 24-well Costar plate at 37° C. The plates are pre-incubated at 37° C. for twenty minutes prior to enzyme addition. A TNBS detection assay as described above is performed on the supernatant after two hours of incubation at 37° C.

It is contemplated that these assays will find use in demonstrating the comparative ability of the mutant variants to hydrolyze such substrates versus proteases from a known mutant variant (P1). In most case, it is contemplated that the mutated enzymes will typically show significant hydrolysis of collagen, elastin and keratin substrates at different pHs and different enzyme concentrations, as compared to each other and wild-type enzyme.

Example 9

Thermal Stability of Protein Variants in piperazine-N-N'-bis-2-ethane Sulfonic Acid ("PIPES") Buffer In these experiments, the thermal stability of the protein (e.g., protease) variants in PIPES is determined. Typically, these determinations are conducted using a PCR thermocycler of the type Stratagene Robocycler. The stability of 5.0 ppm enzyme 5.0 ppm enzyme (e.g., P1 and the mutants of interest) are tested at five timepoints (e.g., 5, 10, 20, 40, and 60 minutes) at pH 6.5, for each temperature. For example, the samples are tested at two degree intervals ranging from 42-56° C., and at every other degree at temperatures ranging from 42-56° C., in the PCR thermocycler gradient. In these experiments, a 50 mM PIPES buffer is prepared (50 mM PIPES, 0.005% Tween 80®). Typically, the pH is adjusted to 6.5. However, it is not intended that the present invention be limited to this particular method, as various methods are known in the art to determine the thermal stability of enzymes.

Samples are assayed using standard succinyl-ala-ala-pro-phe-para-nitro anilide ("SAAPFpNA") assay (See e.g., Delmar, Anal. Biochem., 94:316-320 [1979]; and Achtstetter, Arch. Biochem. Biophys., 207:445-54 [1981]), at pH 6.5, and at 25° C. The samples are diluted to about 300 milliOD/minute. The thermal stability is typically expressed as enzyme half-life (min) as determined by:

H.L.=ln 2/slope, wherein the slope is the slope of curve of rate v. time for each temperature.

By using these means, the stability of mutant variants can be readily compared relative the control P1 and/or wild-type enzyme.

Example 10

Thermal Stability of Protease Variants in N-tris(Hydroxymethyl)methyl-2-Aminoethanesulfonic Acid ("TES")

In these experiments, the thermal stability of the variants in TES is determined. As described above in Example 9, 5.0 ppm enzyme (e.g., P1 and the mutants of interest) are tested at five timepoints (e.g., 5, 10, 20, 40, and 60 minutes) at pH 6.5, for each temperature. For example, the samples are tested at two degree intervals ranging from 42-56° C., and at every other degree at temperatures ranging from 42-56° C., in the PCR thermocycler gradient. A TES buffer is prepared by mixing 50 mM TES (Sigma T 1375), 0.005% Tween 80®. Typically, the pH is adjusted to 6.5.

Thermal stability of the variants can be determined as activity of the residual variant as measured using a succinyl-ala-ala-pro-phe-para-nitroanilide ("AAPFpNA") as known in the art, using reagents such as Sigma no. S-7388 (mol. wt. 624.6 g/mole) (See e.g., Delmar et al., Anal. Biochem., 94:316-320 [1979]; and Achtstetter, Arch. Biochem. Biophys., 207:445-454 [1981]), tested at pH 6.5, and at a temperature of 25° C. The (yellow) p-nitroanilide (pNA) formed in the reaction is measured spectrophotometrically at 410 nm: $.\epsilon_M$=8,480 $M_{-1}$. $cm_{-1}$, ( ) with a SpectraMax 250 spectrophotometer, the samples being diluted to about 300 mOD/min. The thermal stability is expressed as enzyme half-life (min) as described above. As indicated above, these experiments provide means to compare the stability of the variant enzyme preparations with the control P1 and/or wild-type enzyme.

Example 11

Stability of Protease Variants in Bodywash Solutions and Other Personal Care Products Using the cloned enzymes (as described in Example 4), stability of various protease variants are measured using the following protocol.

Method to Measure Solution Stability

In these experiments, P1 and mutant variants are tested in at least two studies, with the first study involving testing for 30 minutes at 45° C., and the second involving testing for 30 minutes at 50° C. For these tests, 50/50 (w/w) bodywash solution are prepared by mixing a commercially available bodywash (e.g., the bodywash sold under the trademark ZEST®, from Procter & Gamble), with deionized water. The pH of the buffer blend is approximately 6.8.

The enzymes to be tested are diluted such that their final enzyme concentration in a 50 w/w % BodyWash: deionized water solution produces a change in $OD_{405}$ of 0.5 to 1.0 when 10 μl of the enzyme/body wash solution is assayed using SAAPFpNA assay endpoint method. Once the amount of dilution is ascertained, 200 μl of the diluted mixture is placed into 96 well microtiter plate wells. The plate are sealed and placed in a water bath at 40° C., for one study, and at 50° C., for the second study. The plates are removed from the water bath after the desired length of time (e.g., 30 or 45 minutes) and 10 μl samples assayed by the endpoint method. The percent of activity remaining is calculated as 100 times the final activity divided by the initial activity.

In some experiments, the variants including the specific residues determined by the assay of the earlier described example show an increased amount of enzymatic activity remaining and thus have a broader thermal stability than P1. For example, at 50° C., some variant compounds have a greater percentage activity remaining whereas P1 or the wild-type without the stabilizing residue variants have a lower percentage of activity remaining. In some experiments, all enzymes have enhanced stability in the presence of bodywash at 50°, but P1-[epitopic variants] with different stability variants have even better stability.

Indeed, there are numerous applications in which the proteases of the present invention that have reduced immunogenicity find use. In addition to detergents and other cleaning preparations, the proteases having reduced immunogenicity also find use in personal care products. The following tables provide the compositions of various products suitable for use in testing. In these tables, the term "minors" encompasses pH modifiers, preservatives, viscosity modifiers, and perfumes. In these tables, the amounts represent approximate weight percent (as provided by the manufacturer), unless otherwise indicated, and are not intended to indicate significant digits.

MOISTURISING BODYWASH

| RAW MATERIAL | pH = 7 Amount |
|---|---|
| Deionized Water | QS |
| Glycerin | 4.0 |
| PEG-6 Caprylic/Capric Glycerides | 4.0 |
| Palm Kernal Fatty acids | 3.0 |
| Sodium Laureth-3 Sulphate | 45.0 |
| Cocamide MEA | 3.0 |
| Sodium Lauroamphoacetate | 25.0 |
| Soybean Oil | 10.0 |
| Polyquaternium-10 (JR30M) | 0.70 |
| Protease | 1000 ppm |

BODYWASH

| RAW MATERIAL | pH 6.5 Amount | pH 7 Amount | pH 8.5 Amount |
|---|---|---|---|
| Deionized water | QS | QS | QS |
| Sodium Laureth Sulphate | 12 | 15 | 8 |
| Cocamidopropyl Betaine | 8 | 10 | 15 |
| APG Glucoside (Plantacare 2000 [1]) | 0 | 2 | 1 |
| Polyquaternium-10 (JR30M) | 0.25 | 0 | 0 |
| Polyquaternium-7 (Mackam 55) | 0 | 0 | 0.7 |
| Protease | 250 ppm | 500 ppm | 1000 ppm |

[1] Cognis

BODY LOTION

| RAW MATERIAL | pH 7 Amount | pH 7 Amount | pH 7.5 Amount | pH 7 Amount |
|---|---|---|---|---|
| DEIONISED WATER | QS | QS | QS | QS |
| GLYCERINE | 8 | 8 | 10 | 12 |
| ISOHEXADECANE | 3 | 3 | 3 | 6 |
| NIACINAMIDE | 0 | 3 | 5 | 6 |
| ISOPROPYL ISOSTEARATE | 3 | 3 | 3 | 3 |
| Polyacrylamide, Isoparaffin, Laureth-7 (Sepigel 305[2]) | 3 | 3 | 3 | 3 |
| PETROLATUM | 4 | 4 | 4 | 2 |
| NYLON 12 | 2 | 2 | 2.5 | 2.5 |
| DIMETHICONE (DC1403[4]) | 2 | 2 | 2.5 | 2.5 |
| SUCROSE POLYCOTTONSEED OIL | 1.5 | 1.5 | 1.5 | 1.5 |
| Stearyl Alcohol 97% | 1 | 1 | 1 | 1 |
| D PANTHENOL | 1 | 1 | 1 | 1 |
| DL-alphaTOCOPHEROL ACETATE | 1 | 1 | 1 | 1 |
| Cetyl Alcohol 95% | 0.5 | 0.5 | 0.5 | 1 |
| BEHYNYL ALCOHOL | 1 | 1 | 1 | 0.5 |
| EMULGADE PL 68/50 | 0.4 | 0.4 | 0.5 | 0.5 |
| STEARIC ACID | 0.15 | 0.15 | 0.15 | 0.15 |
| Peg-100-stearate (MYRJ 59[1]) | 0.15 | 0.15 | 0.15 | 0.15 |
| Protease | 50 ppm | 50 ppm | 250 ppm | 1000 ppm |

[1] Uniqema
[2] Seppic
[4] Dow Corning

ULTRA-HIGH MOISTURISING FACIAL CREAM/LOTION

| RAW MATERIAL | pH 7 Amount | pH 7 Amount |
|---|---|---|
| Deionized water | QS | QS |
| Glycerin | 12 | 5 |
| PEG 400[6] | 0 | 10 |
| Niacinamide | 5 | 7 |
| Isohexadecane | 5 | 5 |
| Dimethicone (DC1403[3]) | 3 | 2 |
| Polyacrylamide, Isoparaffin, Laureth-7 (Sepigel 305[1]) | 3 | 3 |
| Isopropyl Isostearate | 2 | 2 |
| Polymethylsilsesquioxane | 2 | 2 |
| Cetyl Alcohol 95% | 1 | 1 |
| Sucrose polycottonseed oil | 1 | 1 |
| D-Panthenol | 1 | 1 |
| Vitamin E (Tocopherol Acetate) | 1 | 1 |
| Stearyl Alcohol 95% | 0.5 | 0.5 |
| Cetearyl Glucoside | 0.5 | 0.5 |
| Titanium dioxide | 0.3 | 0.3 |
| Stearic Acid | 0.15 | 0.15 |
| PEG-100-Stearate (Myrj 59[4]) | 0.15 | 0.15 |
| Protease | 500 ppm | 500 ppm |

[1] Seppic
[3] Dow Corning
[4] Uniqema
[5] Scher Chemicals
[6] Dow Chemicals

FACIAL MOISTURISING CREAM

| RAW MATERIAL | pH 7 Amount | pH 7 Amount | pH 7.5 Amount |
|---|---|---|---|
| Deionized water | QS | QS | QS |
| Glycerin | 3 | 5 | 10 |
| Petrolatum | 3 | 3 | 0 |
| Cetyl Alcohol 95% | 1.5 | 1.5 | 1 |
| Dimethicone Copolyol (DC 3225C[4]) | 2 | 2 | 2 |
| Isopropyl Palmitate | 1 | 1 | 0.5 |
| Carbomer 954[2] | 0.7 | 0.7 | 0.7 |
| Dimethicone (DC 200/350 cs[4]) | 1 | 1 | 1 |
| Stearyl Alcohol 97% | 0.5 | 0.5 | 1 |
| Stearic acid | 0.1 | 0.1 | 0.1 |
| Peg-100-stearate (MYRJ 59[1]) | 0.1 | 0.1 | 0.1 |
| Titanium Dioxide | 0.3 | 0.3 | 0.3 |
| Protease | 50 ppm | 250 ppm | 1000 ppm |

[1] Uniqema
[2] B F Goodrich
[4] Dow Corning

EXAMPLE 13

Cleaning Compositions

In addition to the compositions described above, the present invention provides means to develop cleaning compositions having particular characteristics. Indeed, the present invention provides various cleaning compositions that comprise modified proteases. In particularly preferred embodiments, an effective amount of one or more protease enzymes described above are included in compositions useful for cleaning a variety of surfaces in need of proteinaceous stain removal. Such cleaning compositions include detergent compositions for cleaning hard surfaces; detergent compositions for cleaning fabrics; dishwashing compositions; oral cleaning compositions; and denture cleaning compositions. It is intended that these compositions be provided in any form suitable for the particular intended use. Preferably, the cleaning compositions of the present invention comprise from about 0.0001% to about 10% of one or more protease enzymes, more preferably from about 0.001% to about 1%, and more preferably still from about 0.001% to about 0.1%. Several examples of various cleaning compositions wherein the protease enzymes find use are discussed in further detail below. All parts, percentages and ratios used herein are by weight unless otherwise specified.

A. Cleaning Compositions for Hard Surfaces Dishes and Fabrics

The protease enzymes of the present invention find use in any detergent composition where high sudsing and/or good insoluble substrate removal are desired. Thus, the protease enzymes find use with various conventional ingredients to provide fully-formulated hard-surface cleaners, dishwashing compositions, fabric laundering compositions and the like. These compositions are suitable for use in any form (e.g., liquid, granules, bars, etc.) acceptable for the particular application. In addition, these compositions are also suitable for use in commercially available "concentrated" detergents which contain as much as 30%-60% by weight of surfactants.

In some embodiments, the cleaning compositions contain various anionic, nonionic, zwitterionic, etc., surfactants. Such surfactants are typically present at levels of from about 0.1% to about 60%, preferably from about 1% to about 35%, of the compositions. Suitable surfactants include, but are not limited to the conventional $C_{11}$-$C_{18}$ alkyl benzene sulfonates and primary and random alkyl sulfates, the $C_{10}$-$C_{18}$ secondary (2,3) alkyl sulfates of the formulas $CH_3$ $(CH_2)x$ $(CHOSO_3)^{-}M^{+})CH_3$, and $CH_3$ $(CH_2)y$ $(CHOSO_3^{-}M^{+})$ $CH_2CH_3$, wherein x and (y+1) are integers of at least about 7, preferably at least about 9, and M is a water-solubilizing cation, especially sodium, the $C_{10}$-$C_{18}$ alkyl alkoxy sulfates (especially EO 1-7 ethoxy sulfates), $C_{10}$-$C_{18}$ alkyl alkoxy carboxylates (especially the EO 1-7 ethoxycarboxylates), the $C_{10}$-$C_{18}$ alkyl polyglycosides, and their corresponding sulfated polyglycosides, $C_{12}$-$C_{18}$ alpha-sulfonated fatty acid esters, $C_{12}$-$C_{18}$ alkyl and alkyl phenol alkoxylates (especially ethoxylates and mixed ethoxy/propoxy), $C_{12}$-$C_{18}$ betaines and sulfobetaines ("sultaines"), $C_{10}$-$C_{18}$ amine oxides, $C_8$-$C_{24}$ sarcosinates (especially oleoyl sarcosinate), and the like. The alkyl alkoxy sulfates (AES) and alkyl alkoxy carboxylates (AEC) are preferred herein. Furthermore, use of such surfactants in combination with the aforesaid amine oxide and/or betaine or sultaine surfactants is also preferred, depending on the desires of the formulator. Other conventional useful surfactants are known to those in the art, including, but not limited to the particularly useful surfactants such as the $C_{10}$-$C_{18}$ N-methyl glucamides (See, U.S. Pat. No. 5,194,639, incorporated herein by reference).

In some embodiments, the compositions of the present invention comprise member(s) of the class of nonionic surfactants which are condensates of ethylene oxide with a hydrophobic moiety to provide a surfactant having an average hydrophilic-lipophilic balance (HLB) in the range from 5 to 17, preferably from 6 to 14, more preferably from 7 to 12. The hydrophobic (lipophilic) moiety may be aliphatic or aromatic in nature and the length of the polyoxyethylene group which is condensed with any particular hydrophobic group can be readily adjusted to yield a water-soluble compound having the desired degree of balance between hydrophilic and hydrophobic elements. Especially preferred are the $C_9$-$C_{15}$ primary alcohol ethoxylates (or mixed ethoxy/propoxy) containing 3-8 moles of ethylene oxide per mole of alcohol, particularly the $C_{14}$-$C_{15}$ primary alcohols containing 6-8 moles of ethylene oxide per mole of alcohol, the $C_{12}$-$C_{15}$ primary alcohols containing 35 moles of ethylene oxide per mole of alcohol, and mixtures thereof.

A wide variety of other ingredients useful in detergent cleaning compositions find use in the compositions herein, including other active ingredients, carriers, hydrotropes, processing aids, dyes or pigments, solvents for liquid formulations, etc. For an additional increment of sudsing, suds boosters such as the $C_{10}$-$C_{16}$ alkolamides can be incorporated into the compositions, typically at about 1% to about 10% levels. The $C_{10}$-$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, from about 0.1% to about 2%, to provide additional sudsing.

The liquid detergent compositions herein typically contain water and other solvents as carriers. Low molecular weight primary or secondary alcohols (e.g., methanol, ethanol, propanol, and isopropanol) are suitable. Monohydric alcohols are preferred for solubilizing surfactants, but polyols such as those containing from about 2 to about 6 carbon atoms and from about 2 to about 6 hydroxy groups (e.g., 1,3-propanediol, ethylene glycol, glycerine, and 1,2-propanediol) also find use in the detergents of the present invention. In some embodiments, the compositions contain about 90%, or from about 10% to about 50% of such carriers.

The detergent compositions herein are preferably formulated such that during use in aqueous cleaning operations, the wash water has a pH between about 6.8 and about 11.0. Thus, finished products are typically formulated at this range. Techniques for controlling pH at recommended usage levels include the use of buffers, alkalis, acids, etc., and are well known to those skilled in the art.

When formulating the hard surface cleaning compositions and fabric cleaning compositions of the present invention, the formulator may wish to employ various builders at levels from about 5% to about 50% by weight. Typical builders include the 1-10 micron zeolites, polycarboxylates such as citrate and oxydisuccinates, layered silicates, phosphates, and the like. Other conventional builders are known to those in the art and are suitable for inclusion in the compositions of the present invention.

Likewise, the formulator may wish to employ various additional enzymes, such as cellulases, lipases, amylases, peroxidases, and proteases in such compositions, typically at levels of from about 0.001% to about 1% by weight. Various detersive and fabric care enzymes are well-known in the laundry detergent art and are suitable for inclusion in the compositions of the present invention.

Various bleaching compounds, such as the percarbonates, perborates and the like, also find use in the compositions of the present invention. These bleaching compounds are typically present at levels from about 1% to about 15% by weight. If desired, such compositions can also contain bleach activators such as tetraacetyl ethylenediamine, nonanoyloxybenzene sulfonate, and the like, which are also known in the art. Usage levels of such compounds typically range from about 1% to about 10% by weight.

Various soil release agents, especially of the anionic oligoester type, various chelating agents, especially the aminophosphonates and ethylenediaminedisuccinates, various clay soil removal agents, especially ethoxylated tetraethylene pentamine, various dispersing agents, especially polyacrylates and polyasparatates, various brighteners, especially anionic brighteners, various dye transfer inhibiting agents, such as polyvinyl pyrrolidone, various suds suppressors, especially silicones and secondary alcohols, various fabric softeners, especially smectite clays and clay floculating polymers (e.g., poly(oxy ethylene)), and the like all find use in the compositions of the present invention, most typically at levels ranging from about 1% to about 35% by weight.

Enzyme stabilizers also find use in the cleaning compositions of the present invention. Such enzyme stabilizers include, but are not limited to propylene glycol (preferably from about 1% to about 10%), sodium formate (preferably from about 0.1% to about 1%) and calcium formate (preferably from about 0.1% to about 1%).

1. Hard Surface Cleaning Compositions

In preferred embodiments, hard surface cleaning compositions of the present invention comprise an effective amount of one or more protease enzymes, preferably from about 0.0001% to about 10%, more preferably from about 0.001% to about 5%, more preferably still from about 0.001% to about 1% by weight of active protease enzyme of the composition. In addition to comprising one or more protease enzymes, such hard surface cleaning compositions typically comprise a surfactant and a water-soluble sequestering builder. However, in certain specialized products such as spray window cleaners, the surfactants are sometimes not used since they may produce a filmy/streaky residue on the glass surface.

The surfactant component, when present, may comprise as little as 0.1% of the compositions herein, but typically the compositions will contain from about 0.25% to about 10%, more preferably from about 1% to about 5% of surfactant.

Typically the compositions will contain from about 0.5% to about 50% of a detergency builder, preferably from about 1% to about 10%. Preferably, the pH should be in the range of about 8 to 12. Conventional pH adjustment agents such as sodium hydroxide, sodium carbonate or hydrochloric acid can be used if adjustment is necessary.

In some embodiments, at least one solvent is included in the compositions. Useful solvents include, but are not limited to, glycol ethers such as diethyleneglycol monohexyl ether, diethyleneglycol monobutyl ether, ethyleneglycol monobutyl ether, ethyleneglycol monohexyl ether, propyleneglycol monobutyl ether, dipropyleneglycol monobutyl ether, and diols such as 2,2,4-trimethyl-1,3pentanediol and 2-ethyl-1,3-hexanediol. When used, such solvents are typically present at levels of from about 0.5% to about 15%, preferably from about 3% to about 11%.

Additionally, highly volatile solvents such as isopropanol or ethanol find use in the present compositions, in order to facilitate faster evaporation of the composition from surfaces when the surface is not rinsed after "full strength" application of the composition to the surface. When used, volatile solvents are typically present at levels of from about 2% to about 12% in the compositions.

The hard surface cleaning composition embodiment of the present invention is illustrated by the following nonlimiting examples. In the following examples, reference to "Protease #" in the examples is to the variant useful in the present invention compositions having a reduced immunogenic responding protease variant of percentages of 0.10, 0.20, 0.10, 0.05, 0.03, and 0.02.

Liquid Hard Surface Cleaning Compositions

| Component | Example No. | | | | | |
|---|---|---|---|---|---|---|
| | 1 | 2 | 3 | 4 | 5 | 6 |
| EDTA** | | | 2.90 | 2.90 | | |
| Na Citrate | | | | | 2.90 | 2.90 |
| NaC$_{12}$ Alkyl-benzene | 1.95 | | 1.95 | | 1.95 | |
| NaC$_{12}$ Alkylsulfate | | 2.20 | | 2.20 | | 2.20 |
| NaC$_{12}$ (ethoxy)*** | | 2.20 | | 2.20 | | 2.20 |
| C$_{12}$ Dimethylamine | | 0.50 | | 0.50 | | 0.50 |
| Na Cumene sulfonate | 1.30 | | 1.30 | | 1.30 | |
| Hexyl Carbitol*** | 6.30 | 6.30 | 6.30 | 6.30 | 6.30 | 6.30 |
| Water**** | Balance to 100% | | | | | |

**Na$_4$ Ethylenediamine diacetic acid
***Diethyleneglycol monohexyl ether
****All formulae adjusted to pH 7.

In some embodiments of the above examples, additional proteases useful in the present invention are substituted with substantially similar results. In addition, in some embodiments of the above examples, any combination of the reduced immunogenic proteases useful in the present invention are substituted in the above formulations with anticipated substantially similar results.

The following Table provides sample compositions suitable for cleaning hard surfaces and removing mildew. The product compositions are typically at approximately pH 7.

Spray Compositions for Cleaning Hard Surfaces and Removing Household Mildew

| Component | Example No. | | | | | |
|---|---|---|---|---|---|---|
| | 7 | 8 | 9 | 10 | 11 | 12 |
| Protease # | 0.20 | 0.05 | 0.10 | 0.30 | 0.20 | 0.30 |
| Protease # + 14 | | | | | 0.30 | 0.10 |
| Sodium octyl sulfate | 2.00 | 2.00 | 2.00 | 2.00 | 2.00 | 2.00 |
| Sodium dodecyl sulfate | 4.00 | 4.00 | 4.00 | 4.00 | 4.00 | 4.00 |
| NaOH | 0.80 | 0.80 | 0.80 | 0.80 | 0.80 | 0.80 |
| Silicate (Na) | 0.04 | 0.04 | 0.04 | 0.04 | 0.04 | 0.04 |
| Perfume | 0.35 | 0.35 | 0.35 | 0.35 | 0.35 | 0.35 |
| Water | Balance to 100% | | | | | |

In Examples 11 and 12, any combination of the protease enzymes useful in the present invention are substituted in with substantially anticipated similar results.

2. Dishwashing Compositions

In additional embodiments of the present invention, dishwashing compositions comprising one or more protease enzymes are provided. The dishwashing compositions embodiment of the present invention are illustrated below. Proteases are included with percentages at 0.5, 0.4, 0.1, 0.05, 0.03, and 0.02. In these compositions, the product pH is adjusted to 7.

Dishwashing Compositions

| Component | \multicolumn{6}{c}{Example No.} | | | | | |
|---|---|---|---|---|---|---|
| | 13 | 14 | 15 | 16 | 17 | 18 |
| $C_{12}$-$C_{14}$ N-methyl- | 0.90 | 0.90 | 0.90 | 0.90 | 0.90 | 0.90 |
| $C_{12}$ ethoxy (1) sulfate | 12.0 | 12.0 | 12.0 | 12.0 | 12.0 | 12.0 |
| 2-methyl undecanoic acid | 4.50 | 4.50 | | 4.50 | 4.50 | |
| $C_{12}$ ethoxy (2) carboxylate | 4.50 | 4.50 | 4.50 | 4.50 | 4.50 | 4.50 |
| $C_{12}$ alcohol ethoxylate (4) | 3.00 | 3.00 | 3.00 | 3.00 | 3.00 | 3.00 |
| $C_{12}$ amine oxide | 3.00 | 3.00 | 3.00 | 3.00 | 3.00 | 3.00 |
| Sodium cumene sulfonate | 2.00 | 2.00 | 2.00 | 2.00 | 2.00 | 2.00 |
| Ethanol | 4.00 | 4.00 | 4.00 | 4.00 | 4.00 | 4.00 |
| Mg Supp$^{++}$ (MgCl$_2$) | 0.20 | 0.20 | 0.20 | 0.20 | 0.20 | 0.20 |
| Ca Supp$^{++}$ (CaCl$_2$) | 0.40 | 0.40 | 0.40 | 0.40 | 0.40 | 0.40 |
| Water | \multicolumn{6}{c}{Balance to 100%} | | | | | |

In some embodiments of the immediately above examples the proteases useful in the present invention described above are substituted in the above formulations, with substantially similar results. Furthermore, in some embodiments of the immediately above examples, any combination of the protease enzymes useful in the present invention, among others, are substituted in the above formulations with substantially similar results.

Granular Automatic Dishwashing Compositions

| Component | Example A | Example B | Example C |
|---|---|---|---|
| Citric acid | 15.0 | | |
| Citrate | 4.0 | 29.0 | 15.0 |
| Acrylate/methacrylate copolymer | 6.0 | | 6.0 |
| Acrylic acid maleic acid copolymer | | 3.7 | |
| Dry add carbonate | 9.0 | | 20.0 |
| Alkali metal silicate | 8.5 | 17.0 | 9.0 |
| Paraffin | | 0.5 | |
| Benzotriazole | | 0.3 | |
| Termamyl 60T | 1.5 | 1.5 | 1.0 |
| Protease #4 (4.6% prill) | 1.6 | 1.6 | 1.6 |
| Percarbonate (AvO) | 1.5 | | |
| Perborate monohydrate | | 0.3 | 1.5 |
| Perborate tetrahydrate | | 0.9 | |
| Tetraacetylethylene diamine | 3.8 | 4.4 | |
| Diethylene triamine penta methyphosphonic acid (Mg salt) | 0.13 | 0.13 | 0.13 |
| Alkyl ethoxy sulphate--3x ethoxylated | 3.0 | | |
| Alkyl ethoxy propoxy nonionic surfactant | | | |
| Suds suppressor | 2.0 | | |
| Olin SLF18 nonionic surfactant | | | |
| Sulfate | | | |

In the immediately above formulations a reduced immunogenic protease useful in the present invention is substituted therein with substantially similar results. Also in the immediately above formulations, any combination of the proteases useful in the present invention recited herein can be substituted in with substantially anticipated similar results.

3. Fabric Cleaning Compositions

The present invention further provides fabric cleaning compositions comprising one or more protease enzymes.

a. Granular Fabric Cleaning

The granular fabric cleaning compositions of the present invention contain an effective amount of one or more protease enzymes, preferably from about 0.001% to about 10%, more preferably from about 0.005% to about 5%, more preferably from about 0.01% to about 1% by weight of active protease enzyme of the composition. In addition to one or more protease enzymes, the granular fabric cleaning compositions typically comprise at least one surfactant, one or more builders, and, in some cases, a bleaching agent. Granular fabric cleaning composition embodiments of the present invention are illustrated by the following examples.

Granular Fabric Cleaning Compositions

| Component | \multicolumn{4}{c}{Example No.} | | | |
|---|---|---|---|---|
| | 20 | 21 | 22 | 23 |
| Protease (4% Prill) | 0.10 | 0.20 | 0.03 | 0.05 |
| Protease (4% Prill) | | | 0.02 | 0.05 |
| $C_{13}$ linear alkyl benzene sulfonate | 22.0 | 22.0 | 22.0 | 22.0 |
| Phosphate (as sodium tripolyphosphates) | 23.0 | 23.0 | 23.0 | 23.0 |
| Sodium carbonate | 23.0 | 23.0 | 23.0 | 23.0 |
| Sodium silicate | 12.0 | 14.0 | 14.0 | 14.0 |
| Zeolite | 8.20 | 8.20 | 8.20 | 8.20 |
| Chelant (diethylaenetriamine-pentaacetic acid) | 0.40 | 0.40 | 0.40 | 0.40 |
| Sodium sulfate | 5.50 | 5.50 | 5.50 | 5.50 |
| Water | \multicolumn{4}{c}{Balance to 100%} | | | |

In the immediately above formulations a reduced immunogenic protease useful in the present invention is substituted therein with substantially similar results. Also in the immediately above formulations, any combination of the proteases useful in the present invention recited herein can be substituted in with substantially similar results.

| Granular Fabric Cleaning Composition | | | | |
|---|---|---|---|---|
| | Example No. | | | |
| Component | 24 | 25 | 26 | 27 |
| Protease #(4% Prill) | 0.10 | 0.20 | 0.03 | 0.05 |
| Protease # + 1 (4% Prill) | | | 0.02 | 0.05 |
| $C_{12}$ alkyl benzene sulfonate | 12.0 | 12.0 | 12.0 | 12.0 |
| Zeolite A (1-10 μm) | 26.0 | 26.0 | 26.0 | 26.0 |
| 2-butyl octanoic acid | 4.0 | 4.0 | 4.0 | 4.0 |
| $C_{12}$-$C_{14}$ secondary (2,3) | 5.0 | 5.0 | 5.0 | 5.0 |
| Sodium citrate | 5.0 | 5.0 | 5.0 | 5.0 |
| Optical brightener | 0.10 | 0.10 | 0.10 | 0.10 |
| Sodium sulfate | 17.0 | 17.0 | 17.0 | 17.0 |
| Fillers, water, minors | Balance to 100% | | | |

In the immediately above formulations a reduced immunogenic protease useful in the present invention is substituted therein with substantially similar results. Also in the immediately above formulations, any combination of the proteases useful in the present invention recited herein can be substituted in with substantially similar results.

| Granular Fabric Cleaning Compositions | | |
|---|---|---|
| | Example No. | |
| Component | 28 | 29 |
| Linear alkyl benzene sulphonate | 11.4 | 10.7 |
| Tallow alkyl sulphate | 1.8 | 2.4 |
| $C_{14-15}$ alkyl sulphate | 3.0 | 3.10 |
| $C_{14-15}$ alcohol 7 times ethoxylated | 4.0 | 4.0 |
| Tallow alcohol 11 times ethoxylated | 1.8 | 1.8 |
| Dispersant | 0.07 | 0.1 |
| Silicone fluid | 0.80 | 0.80 |
| Trisodium citrate | 14.0 | 15.0 |
| Citric acid | 3.0 | 2.5 |
| Zeolite | 32.5 | 32.1 |
| Maleic acid acrylic acid copolymer | 5.0 | 5.9 |
| Diethylene triamine penta methylene | 1.0 | 0.20 |
| Protease # (4% Prill) | 0.30 | 0.30 |
| Lipase | 0.36 | 0.40 |
| Amylase | 0.30 | 0.30 |
| Sodium silicate | 2.0 | 2.5 |
| Sodium sulphate | 3.5 | 5.2 |
| Polyvinyl pyrrolidone | 0.3 | 0.5 |
| Perborate | 0.5 | 1 |
| Phenol sulphonate | 0.1 | 0.2 |
| Peroxidase | 0.1 | 0.1 |
| Minors | Up to 100 | |

| | Example No. | |
|---|---|---|
| Component | 30 | 31 |
| Sodium linear $C_{12}$ alkyl benzene sulphonate | 6.5 | 8.0 |
| Sodium sulphate | 15.0 | 18.0 |
| Zeolite | 26.0 | 22.0 |
| Sodium nitrilotriacetate | 5.0 | 5.0 |
| Polyvinyl pyrrolidone | 0.5 | 0.7 |
| Tetraacetylethylene diamine | 3.0 | 3.0 |
| Boric acid | 4.0 | |
| Perborate | 0.5 | 1 |
| Phenol sulphonate | 0.1 | 0.2 |
| Protease #4 (4% Prill) | 0.4 | 0.4 |
| Fillers (e.g., silicates, carbonates, perfumes) | Up to 100 | |

In additional embodiments, compact granular fabric cleaning compositions such as the following are provided. The ingredients are provided in terms of the weight percent. Composition 1: alkyl sulphate (8.0), alkyl ethoxy sulphate (2.0), a mixture of C25 and C45 alcohol 3 and 7 times ethoxylated (6.0), polyhydroxy fatty acid amide (2.5), Zeolite (17.0), layered silicate/citrate (16.0), carbonate (7.0), maleic acid acrylic acid copolymer (5.0), soil release polymer (0.4), carboxymethyl cellulose (0.4), poly(4-vinylpyridine)-N-oxide (0.1), copolymer of vinylimidazole and vinylpyrrolidone (0.1), PEG-2000 (0.2), protease # (4% Prill) (0.5), lipase (0.2), cellulase (0.2), tetraacetylethylene diamine (6.0), percarbonate (22.0), ethylene diamine disuccinic acid (0.3), suds suppressor (3.5), disodium-4,4'-bis(2-morpholino-4-anilino-s-triazin-6-ylamino)stilbene-2,2'-disulphonate (0.25), Disodium-4,4'-bis(2-sulfostyril)biphenyl (0.05), and a combination of water, perfume and minors (up to 100).

In an alternative granular fabric cleaning composition, the following ingredients are is provided. The ingredients are provided in terms of the weight percent. Composition 2: linear alkyl benzene sulphonate (7.6), $C_{16}$-$C_{18}$ alkyl sulfate (1.3), $C_{14-15}$ alcohol 7 times ethoxyiated (4.0), coco-alkyl-dimethyl hydroxyethyl ammonium chloride (1.4), dispersant (0.07), silicone fluid (0.8), trisodium citrate (5.0), Zeolite 4A (15.0), maleic acid acrylic acid copolymer (4.0), diethylene triamine penta methylene phosphonic acid (0.4), perborate (15.0), tetraacetylethylene diamine (5.0), smectite clay (10.0), poly (oxy ethylene) (MW 300,000) (0.3), protease # (4% Prill) (0.4), lipase (0.2), amylase (0.3), cellulase (0.2), sodium silicate (3.0), sodium carbonate (10.0), carboxymethyl cellulose (0.2), brighteners (0.2), and a mixture of water, perfume and minors (up to 100).

In yet another alternative granular fabric cleaning composition, the following ingredients are provided. The ingredients are provided in terms of the weight percent. Composition 2: linear alkyl benzene (6.92), tallow alkyl sulfate (2.05), $C_{14-15}$ alcohol 7 times ethoxylated (4.4), $C_{12-15}$ alkyl ethoxy sulfate—3 times ethoxylated (0.16), Zeolite (20.2), citrate (5.5), carbonate (15.4), silicate (3.0), maleic acid acrylic acid copolymer (4.0), carboxymethyl cellulase (0.31), soil release polymer (0.30), protease # (4% Prill) (0.2), lipase (0.36), cellulase (0.13), perborate tetrahydrate (11.64), perborate monohydrate (8.7), tetraacetylethylene diamine (5.0), diethylene tramine penta methyl phosphonic acid (0.38), magnesium sulfate (0.40), brightener (0.19), a mixture of perfume, silicone, and suds suppressors (0.85), and minors (up to 100).

In the immediately above formulations a reduced immunogenic protease useful in the present invention is substituted therein with substantially similar results.

Also in the immediately above formulations, any combination of the proteases useful in the present invention recited herein can be substituted in with substantially similar results.

b. Liquid Fabric Cleaning Compositions

Liquid fabric cleaning compositions of the present invention comprise an effective amount of one or more protease enzymes, preferably from about 0.0001% to about 10%, more preferably from about 0.001% to about 1%, and most preferably from about 0.001% to about 0.1%, by weight of active protease enzyme of the composition. Such liquid fabric cleaning compositions typically additionally comprise an anionic surfactant, a fatty acid, a water-soluble detergency builder and water. The liquid fabric cleaning composition embodiment of the present invention is illustrated by the following examples.

Liquid Fabric Cleaning Compositions

| Component | Example No. | | | | |
|---|---|---|---|---|---|
| | 35 | 36 | 37 | 38 | 39 |
| Protease # | 0.05 | 0.03 | 0.30 | 0.03 | 0.10 |
| Protease # + 1 | | | | 0.01 | 0.20 |
| $C_{12}$-$C_{14}$ alkyl sulfate, Na | 20.0 | 20.0 | 20.0 | 20.0 | 20.0 |
| 2-butyl octanoic acid | 5.0 | 5.0 | 5.0 | 5.0 | 5.0 |
| Sodium citrate | 1.0 | 1.0 | 1.0 | 1.0 | 1.0 |
| $C_{10}$ alcohol ethoxylate (3) | 13.0 | 13.0 | 13.0 | 13.0 | 13.0 |
| Monethanolamine | 2.5 | 2.5 | 2.5 | 2.5 | 2.5 |
| Water/propylene glycol/ ethanol | Balance to 100% (100:1:1) | | | | |

In the immediately above formulations a reduced immunogenic protease useful in the present invention is substituted therein with substantially similar results. Also in the immediately above formulations, any combination of the proteases useful in the present invention recited herein can be substituted in with substantially similar results.

Liquid Fabric Cleaning Compositions

| Component | Example No. | |
|---|---|---|
| | 40 | 41 |
| $C_{12-14}$ alkyl succinic acid | 3.0 | 8.0 |
| Citric acid monohydrate | 10.0 | 15.0 |
| Sodium $C_{12-15}$ alkyl sulphate | 8.0 | 8.0 |
| Sodium sulfate of $C_{12-15}$ alcohol 2 times ethoxylated | | 3.0 |
| $C_{12-15}$ alcohol 7 times ethoxylated | | 8.0 |
| $C_{12-15}$ alcohol 5 times ethoxylated | 8.0 | |
| Diethylene triamine penta (methylene phosphonic acid) | 0.2 | |
| Oleic acid | 1.8 | |
| Ethanol | 4.0 | 4.0 |
| Propanediol | 2.0 | 2.0 |
| Protease # | 0.2 | 0.2 |
| Polyvinyl pyrrolidone | 1.0 | 2.0 |
| Suds suppressor | 0.15 | 0.15 |
| NaOH | | up to pH 7.5 |
| Perborate | 0.5 | 1.0 |
| Phenol sulphonate | 0.1 | 0.2 |
| Peroxidase | 0.4 | 0.1 |
| Water and minors | Up to 100 | |

In the immediately above formulations a reduced immunogenic protease useful in the present invention is substituted therein with substantially similar results. Also in the immediately above formulations, any combination of the proteases useful in the present invention recited herein can be substituted in with substantially similar results.

c. Bar Fabric Cleaning Compositions

Bar fabric cleaning compositions of the present invention suitable for hand-washing soiled fabrics contain an effective amount of one or more protease enzymes, preferably from about 0.001% to about 10%, more preferably from about 0.01% to about 1% by weight of the composition. The bar fabric cleaning composition embodiments of the present invention is illustrated by the following examples.

Bar Fabric Cleaning Composition

| Component | Example No. | | | |
|---|---|---|---|---|
| | 42 | 43 | 44 | 45 |
| Protease # | 0.3 | | 0.1 | 0.02 |
| Protease # + 1 | | | 0.4 | 0.03 |
| $C_{12}$-$C_{16}$ alkyl sulfate, Na | 20.0 | 20.0 | 20.0 | 20.0 |
| $C_{12}$-$C_{14}$—N-methyl glucamide | 5.0 | 5.0 | 5.0 | 5.0 |
| $C_{11}$-$C_{13}$ alkyl benzene sulfonate, Na | 10.0 | 10.0 | 10.0 | 10.0 |
| Sodium carbonate | 25.0 | 25.0 | 25.0 | 25.0 |
| Sodium pyrophosphate | 7.0 | 7.0 | 7.0 | 7.0 |
| Sodium tripolyphosphate | 7.0 | 7.0 | 7.0 | 7.0 |
| Zeolite A (0.1-10 μm) | 5.0 | 5.0 | 5.0 | 5.0 |
| Carboxymethylcellulose | 0.2 | 0.2 | 0.2 | 0.2 |
| Polyacrylate (MW 1400) | 0.2 | 0.2 | 0.2 | 0.2 |
| Coconut monethanolamide | 5.0 | 5.0 | 5.0 | 5.0 |
| Brightener, perfume | 0.2 | 0.2 | 0.2 | 0.2 |
| $CaSO_4$ | 1.0 | 1.0 | 1.0 | 1.0 |
| $MgSO_4$ | 1.0 | 1.0 | 1.0 | 1.0 |
| Water | 4.0 | 4.0 | 4.0 | 4.0 |
| Fillers (e.g., $CaCO_3$, talc, clay, silicates, etc.) | Balance to 100% | | | |

In the immediately above formulations a reduced immunogenic protease useful in the present invention is substituted therein with substantially similar results. Also in the immediately above formulations, any combination of the proteases useful in the present invention recited herein can be substituted in with substantially similar results.

d. Additional Cleaning Compositions

In addition to the hard surface cleaning, dishwashing and fabric cleaning compositions discussed above, one or more protease enzymes may be incorporated into a variety of other cleaning compositions where hydrolysis of an insoluble substrate is desired. Such additional cleaning compositions include, but are not limited to oral cleaning compositions, denture cleaning compositions, and contact lens cleaning compositions, as well as other personal care cleaning compositions.

1. Oral Cleaning Compositions

In additional embodiments of the present invention, pharmaceutically-acceptable amounts of one or more protease enzymes are included in compositions useful for removing proteinaceous stains from teeth or dentures. Preferably, oral cleaning compositions of the present invention comprise from about 0.0001% to about 20% of one or more protease enzymes, more preferably from about 0.001% to about 10%, more preferably still from about 0.01% to about 5%, by weight of the composition, and a pharmaceutically-acceptable carrier. Typically, the pharmaceutically-acceptable oral cleaning carrier components of the oral cleaning components of the oral cleaning compositions will generally comprise from about 50% to about 99.99%, preferably from about 65% to about 99.99%, more preferably from about 65% to about 99%, by weight of the composition.

The pharmaceutically-acceptable carrier components and optional components which may be included in the oral cleaning compositions of the present invention are well known to those skilled in the art. A wide variety of composition types, carrier components and optional components useful in the oral cleaning compositions are disclosed in U.S. Pat. No. 5,096,700; U.S. Pat. No. 5,028,414; and U.S. Pat. No. 5,028,415, all of which are incorporated herein by reference. Oral cleaning composition embodiments of the present invention are illustrated by the following examples.

Oral Dentrifice Cleaning Composition

| Component | Example No. | | | |
|---|---|---|---|---|
| | 46 | 47 | 48 | 49 |
| Protease # | 2.0 | 3.5 | 1.5 | 2.0 |
| Sorbitol (70% aq. soln.) | 35.0 | 35.0 | 35.0 | 35.0 |
| PEG-6* | 1.0 | 1.0 | 1.0 | 1.0 |
| Silica dental abrasive** | 20.0 | 20.0 | 20.0 | 20.0 |
| Sodium fluoride | 0.243 | 0.243 | 0.243 | 0.243 |
| Titanium oxide | 0.5 | 0.5 | 0.5 | 0.5 |
| Sodium saccharin | 0.286 | 0.286 | 0.286 | 0.286 |
| Sodium alkyl sulfate (27.9%) | 4.0 | 4.0 | 4.0 | 4.0 |
| Flavor | 1.04 | 1.04 | 1.04 | 1.04 |
| Carboxyvinyl polymer*** | 0.30 | 0.30 | 0.30 | 0.30 |
| Carrageenan**** | 0.8 | 0.8 | 0.8 | 0.8 |
| Water | Balance to 100% | | | |

*PEG-6--Polyethylene glycol, having MW of 600
**Precipitated silica identified as Zeodent 119 (J. M. Huber).
***Carbopol (B. F. Goodrich Chemical Co.)
****Iota carrageenan (Hercules Chemical Co.).

In the immediately above formulations a reduced immunogenic protease useful in the present invention is substituted therein with substantially similar results. Also in the immediately above formulations, any combination of the proteases useful in the present invention recited herein can be substituted in with substantially similar results.

Mouthwash Compositions

| Component | Example No. | | | |
|---|---|---|---|---|
| | 50 | 51 | 52 | 53 |
| Protease # | 3.0 | 7.5 | 1.0 | 5.0 |
| SDA 40 Alcohol | 8.0 | 8.0 | 8.0 | 8.0 |
| Flavor | 0.08 | 0.08 | 0.08 | 0.08 |
| Emulsifier | 0.08 | 0.08 | 0.08 | 0.08 |
| Sodium fluoride | 0.05 | 0.05 | 0.05 | 0.05 |
| Glycerin | 10.0 | 10.0 | 10.0 | 10.0 |
| Sweetener | 0.02 | 0.02 | 0.02 | 0.02 |
| Benzoic acid | 0.05 | 0.05 | 0.05 | 0.05 |
| NaOH | 0.20 | 0.20 | 0.20 | 0.20 |
| Dye | 0.04 | 0.04 | 0.04 | 0.04 |
| Water | Balance to 100% | | | |

In the immediately above formulations a reduced immunogenic protease useful in the present invention is substituted therein with substantially similar results. Also in the immediately above formulations, any combination of the proteases useful in the present invention recited herein can be substituted in with substantially similar results.

Lozenge Compositions

| Component | Example No. | | | |
|---|---|---|---|---|
| | 54 | 55 | 56 | 57 |
| Protease # | 0.01 | 0.03 | 0.10 | 0.02 |
| Sorbitol | 17.50 | 17.50 | 17.50 | 17.50 |
| Mannitol | 17.50 | 17.50 | 17.50 | 17.50 |
| Starch | 13.60 | 13.60 | 13.60 | 13.60 |
| Sweetener | 1.20 | 1.20 | 1.20 | 1.20 |
| Flavor | 11.7 | 11.7 | 11.7 | 11.7 |
| Color | 0.10 | 0.10 | 0.10 | 0.10 |
| Corn syrup | Balance to 100% | | | |

In the immediately above formulations a reduced immunogenic protease useful in the present invention is substituted therein with substantially similar results. Also in the immediately above formulations, any combination of the proteases useful in the present invention recited herein can be substituted in with substantially similar results.

Chewing Gum Compositions

| Component | Example No. | | | |
|---|---|---|---|---|
| | 58 | 59 | 60 | 61 |
| Protease # | 0.03 | 0.02 | 0.10 | 0.05 |
| Sorbitol crystals | 38.44 | 38.4 | 38.4 | 38.4 |
| Paloja-T gum base* | 20.0 | 20.0 | 20.0 | 20.0 |
| Sorbitol (70% aq. soln.) | 22.0 | 22.0 | 22.0 | 22.0 |
| Mannitol | 10.0 | 10.0 | 10.0 | 10.0 |
| Glycerine | 7.56 | 7.56 | 7.56 | 7.56 |
| Flavor | 1.0 | 1.0 | 1.0 | 1.0 |
| Corn syrup | Balance to 100% | | | |

*Supplied by L. A. Dreyfus Co.

In the immediately above formulations a reduced immunogenic protease useful in the present invention is substituted therein with substantially similar results. Also in the immediately above formulations, any combination of the proteases useful in the present invention recited herein can be substituted in with substantially similar results.

2. Denture Cleaning Compositions

In yet additional embodiments, the present invention provides various denture cleaning compositions for cleaning dentures outside of the oral cavity comprise one or more protease enzymes. Such denture cleaning compositions comprise an effective amount of one or more protease enzymes, preferably from about 0.0001% to about 50% of one or more protease enzymes, more preferably from about 0.001% to about 35%, more preferably still from about 0.01% to about 20%, by weight of the composition, and a denture cleansing carrier. Various denture cleansing composition formats such as effervescent tablets and the like are well known in the art (See e.g., U.S. Pat. No. 5,055,305, incorporated herein by reference), and are generally appropriate for incorporation of one or more protease enzymes for removing proteinaceous stains from dentures.

The denture cleaning composition embodiments of the present invention is illustrated by the following examples.

Two-Layer Effervescent Denture Cleansing Table Composition

| Component | Example No. | | | |
|---|---|---|---|---|
| | 62 | 63 | 64 | 65 |
| Acidic Layer: | | | | |
| Protease # | 1.0 | 1.5 | 0.01 | 0.05 |
| Tartaric acid | 24.0 | 24.0 | 24.0 | 24.0 |
| Sodium carbonate | 4.0 | 4.0 | 4.0 | 4.0 |
| Sulphamic acid | 10.0 | 10.0 | 10.0 | 10.0 |
| PEG 20,000 | 4.0 | 4.0 | 4.0 | 4.0 |
| Sodium bicarbonate | 24.5 | 24.5 | 24.5 | 24.5 |
| Potassium persulfate | 15.0 | 15.0 | 15.0 | 15.0 |
| Sodium acid pyrophosphate | 7.0 | 7.0 | 7.0 | 7.0 |
| Pyrogenic silica | 2.0 | 2.0 | 2.0 | 2.0 |
| Tetracetylethylene diamine | 7.0 | 7.0 | 7.0 | 7.0 |
| Ricinoleylsulfosuccinate | 0.5 | 0.5 | 0.5 | 0.5 |
| Flavor | 1.0 | 1.0 | 1.0 | 1.0 |
| Alkaline Layer: | | | | |
| Sodium perborate monohydrate | 32.0 | 32.0 | 32.0 | 32.0 |
| Sodium bicarbonate | 19.0 | 19.0 | 19.0 | 19.0 |
| EDTA | 3.0 | 3.0 | 3.0 | 3.0 |
| Sodium tripolyphosphate | 12.0 | 12.0 | 12.0 | 12.0 |
| PEG 20,000 | 2.0 | 2.0 | 2.0 | 2.0 |
| Potassium persulfate | 26.0 | 26.0 | 26.0 | 26.0 |
| Sodium carbonate | 2.0 | 2.0 | 2.0 | 2.0 |
| Pyrogenic silica | 2.0 | 2.0 | 2.0 | 2.0 |
| Dye/flavor | 2.0 | 2.0 | 2.0 | 2.0 |

In the immediately above formulations a reduced immunogenic protease useful in the present invention is substituted therein with substantially similar results. Also in the immediately above formulations, any combination of the proteases useful in the present invention recited herein can be substituted in with substantially similar results.

3. Personal Cleansing Compositions

In additional embodiments of the present invention, personal cleaning compositions for cleaning the skin comprise one or more of the protease enzymes. Such compositions typically comprise from about 0.001% to about 5% protease enzyme, preferably from about 0.005% to about 2%, and most preferably from about 0.01% to about 0.8% by weight of the composition. Preferred personal cleansing compositions into which can be included protease enzymes as described herein include, but are not limited to those described in U.S. patent application Ser. Nos. 08/121,623 and 08/121,624. Although various compositions are contemplated by the present invention, one liquid personal cleaning composition containing a soap component includes (weight %): soap (K or Na) (15.00), 30% laurate, 30% myristate, 25% palmitate, 15% stearate, fatty acids (above ratios) (4.50), Na lauryl sarcosinate (6.00), sodium laureth-3 sulfate (0.66), cocamidopropylbetaine (1.33), glycerine (15.00), propylene glycol (9.00), polyquaternium 10 (0.80), ethylene glycol distearate (EDTA) (1.50), propylparaben (0.10), methylparaben (0.20), protease # (0.10), KOH or NaOH (if necessary to adjust pH), calcium sulfate (3), acetic acid (3), and water (balance to 100).

In another embodiment, personal cleansing bars are provided by the present invention. Although various compositions are contemplated by the present invention, one bar personal cleaning composition containing a soap component includes (weight sodium cocoyl isethionate (47.20), sodium cetearyl sulfate (9.14), paraffin (9.05), sodium soap (in situ) (3.67), sodium isethionate (5.51), sodium chloride (0.45), titanium dioxide (0.4), trisodium EDTA (0.1), trisodium etidronate (0.1), perfume (1.20), $Na_2SO_4$ (0.87), protease # (0.10), and a mixture of water and minors (balance to 100).

In the immediately above formulations a reduced immunogenic protease useful in the present invention is substituted therein with substantially similar results. Also in the immediately above formulations, any combination of the proteases useful in the present invention recited herein can be substituted in with substantially similar results.

Example 14

Wash Performance Test

The wash performance of the variants useful in the present invention compositions may be evaluated by any suitable means known in the art. One suitable method for measuring the removal of stain from EMPA 116(blood/milk/carbon black on cotton) cloth swatches (Testfabrics, Inc., Middlesex, N.J. 07030) is described in this Example. Six EMPA 116 swatches, cut to 3.times.4½ inches with pinked edges, are placed in each pot of a Model 7243S Terg-O-Tometer (United States Testing Co., Inc., Hoboken, N.J.) containing 1000 ml of water, 15 gpg hardness (Ca++:Mg++:: 3:1::w:w), 7 g of detergent, and enzyme as appropriate. The detergent base is WFK1 detergent from wfk—Testgewebe GmbH, (Krefeld, Germany) and has the following components (% of final formulation): Zeolite A (25%), sodium sulfate (25%), soda ash (10%), linear alkylbenzenesulfonate (8.8%), alcohol ethoxylate (7-8 EO) (4.5%), sodium soap (3%), and sodium silicate ($SiO_2:Na_2O::3.3:1$)(3%).

To this base detergent, the following additions are made (% of final formulation): sodium perborate monohydrate (13%), copolymer (Sokalan CP5) (4%), TAED (Mykon ATC Green) (3%), enzyme (0.5%), and whitener (Tinopal AMS-GX) (0.2%).

Sodium perborate monohydrate can be obtained from various commercial sources, including Degussa Corporation, Ridgefield-Park. Sokalan CP5 is obtained from BASF Corporation, Parsippany, N.J. Mykon ATC Green (TAED, tetraacetylethylenediamine) can be obtained from Warwick International, Limited, England. T inopal AMS GX can be obtained from Ciba-Geigy Corporation, Greensboro, N.C.

In one suitable testing method, six EMPA 116 swatches are washed in detergent with enzyme for 30 min at 60° C., rinsed twice for 5 minutes each time in 1000 ml water. Enzymes are added at final concentrations of 0.05 to 1 ppm for standard curves, and 0.25 ppm for routine analyses. Swatches are dried and pressed, and the reflectance from the swatches is measured using the L value on the L*a*b* scale of a Minolta Chroma Meter, Model CR-200 (Minolta Corporation, Ramsey, N.J.). In some embodiments, the performance of the test enzyme is reported as a percentage of the performance of B. amyloliquefaciens (BPN') protease and is calculated by dividing the amount of B. amyloliquefaciens (BPN') protease by the amount of variant protease that is needed to provide the same stain removal performance-.times.100.

Example 15

Protease Stability in a Liquid Detergent Formulation

This example provides a means for comparison of protease stability toward inactivation in a liquid detergent formulation is made for *Bacillus amyloliquefaciens* subtilisin and its variant enzymes. As other methods find use with the present invention, it is not intended that the present invention be limited to this method.

In this method, the detergent formulation for the study is a commercially available laundry detergent (e.g., Tide Ultra liquid laundry detergent (Proctor & Gamble)). In some embodiments, heat treatment of the detergent formulation is necessary to inactivate in-situ protease. This is accomplished by incubating the detergent at 96° C. for a period of 4.5 hours. Concentrated preparations of the *B. amyloliquefaciens* subtilisin and variant to be tested, in the range of 20 grams/liter enzyme, are then added to the heat-treated detergent, at room-temperature to a final concentration of 0.3 grams/liter enzyme in the detergent formulation. The heat-treated detergent with protease added is then incubated in a water bath at 50° C. Aliquots are removed from the incubation tubes at 0, 24, 46, 76, and 112 hour time intervals and assayed for enzyme activity by addition to a 1 cm cuvette containing 1.2 mM of the synthetic peptide substrate suc-Ala-Ala-Pro-phe-p-nitroanilide dissolved in 0.1M Tris-HCL buffer, pH 8.6, and at 25° C. The initial linear reaction velocity is followed spectrophotometrically by monitoring the absorbance of the reaction product p-nitroaniline at 410 nm as a function of time. In preferred embodiments, the preferred variant(s) are observed to have significantly greater stability towards inactivation than the native *B. amyloliquefaciens* enzyme. Estimated half-lives for inactivation in the laundry detergent formulation for the two enzymes are determined under the specified test conditions.

While particular embodiments of the subject invention have been described, it will be obvious to those skilled in the art that various changes and modifications of the subject invention can be made without departing from the spirit and scope of the invention. Having described the preferred embodiments of the present invention, it will appear to those ordinarily skilled in the art that various modifications may be made to the disclosed embodiments, and that such modifications are intended to be within the scope of the present invention.

---

The invention claimed is:

1. A variant of a subtilisin comprising a T-cell epitope, wherein said subtilisin variant has proteolytic activity and an amino acid sequence at least 85% identical to the amino acid sequence set forth in SEQ ID NO:2 and differs from said subtilisin by having an altered T-cell epitope such that said subtilisin variant exhibits an altered immunogenic response from said subtilisin in a human; wherein said altered T-cell epitope of said subtilisin variant comprises an amino acid substitution of glycine, isoleucine, leucine, methionine, phenylalanine, proline, tryptophan, or tyrosine at an amino acid position corresponding to position 26 of SEQ ID NO:2.

2. The variant of claim 1 wherein said immunogenic response produced by said subtilisin variant is less than said immunogenic response produced by said subtilisin.

3. The variant of claim 2, wherein said immunogenic response produced by said subtilisin variant is characterized by an in vivo reduction in allergenicity, as compared to said subtilisin.

4. The variant of claim 2, wherein said immunogenic response produced by said subtilisin variant is characterized by an in vitro reduction in human peripheral blood mononuclear cell proliferation, as compared to said subtilisin.

5. The variant of claim 1 wherein said immunogenic response produced by said subtilisin variant is greater than said immunogenic response produced by said subtilisin.

6. A composition selected from the group consisting of cleaning compositions, and personal care products, wherein said composition comprises the subtilisin variant of claim 1.

7. A skin care composition comprising a variant of a subtilisin comprising a T-cell epitope, wherein said subtilisin variant has proteolytic activity and an amino acid sequence at least 85% identical to the amino acid sequence set forth in SEQ ID NO:2 and differs from said subtilisin by having an altered T-cell epitope such that said subtilisin variant and said subtilisin produce different immunogenic responses in a human; wherein said altered T-cell epitope of said subtilisin variant comprises an amino acid substitution of glycine, isoleucine, leucine, methionine, phenylalanine, proline, tryptophan, or tyrosine at an amino acid position corresponding to position 26 of SEQ ID NO:2.

8. The skin care composition of claim 7, further comprising a cosmetically acceptable carrier.

9. The skin care composition of claim 8, wherein said carrier comprises at least one hydrophilic diluent selected from the group consisting of water, propylene glycol, ethanol, propanol, glycerol, butylene glycol, polyethylene glycol having a molecular weight from about 200 to about 600, and polypropylene glycol having a molecular weight from about 425 to about 2025.

10. The skin care composition of claim 7, further comprising at least one skin care active.

11. The skin care composition of claim 10, wherein said skin care active is selected from the group consisting of Vitamin B3 component, panthenol, Vitamin E, Vitamin E acetate, retinol, retinyl propionate, retinyl palmitate, retinoic acid, Vitamin C, theobromine, alpha-hydroxyacid, farnesol, phytrantriol, salicylic acid, and palmityl peptapeptide-3.

12. The skin care composition of claim 11, wherein said Vitamin B3 component is niacinamide.

13. The skin care composition of claim 7, further comprising glycerine.

14. A skin care composition comprising:
a) from about 0.00001% to about 1%, by weight, of a variant of a subtilisin comprising a T-cell epitope, wherein said subtilisin variant has proteolytic activity and an amino acid sequence at least 85% identical to the amino acid sequence set forth in SEQ ID NO:2 and differs from said subtilisin by having an altered T-cell epitope such that said subtilisin variant and said subtilisin produce different immunogenic responses in a human; wherein said T-cell epitope of said protease of interest comprises an amino acid substitution of glycine, isoleucine, leucine, methionine, phenylalanine, proline, tryptophan, or tyrosine at an amino acid position corresponding to position 26 of SEQ ID NO:2;
b) from about 0.01% to about 20%, by weight, of a humectant;
c) from about 0.1% to about 20%, by weight, of a skin care active;
d) from about 0.05% to about 15%, by weight, of a surfactant; and
e) from about 0.1% to about 20%, by weight, of silicone.

15. A cleaning composition comprising at least one variant of a subtilisin comprising a T-cell epitope, wherein said subtilisin variant has proteolytic activity and an amino acid sequence at least 85% identical to the amino acid sequence set forth in SEQ ID NO:2 and differs from said subtilisin by having an altered T-cell epitope such that said subtilisin variant and said subtilisin produce different immunogenic responses in a human; wherein said altered T-cell epitope of said subtilisin variant comprises an amino acid substitution of glycine, isoleucine, leucine, methionine, phenylalanine, proline, tryptophan, or tyrosine at an amino acid position corresponding to position 26 of SEQ ID NO:2.

16. A nucleic acid encoding the subtilisin variant of claim 1.

17. An expression vector comprising the nucleic acid of claim 16.

18. A host cell transformed with the expression vector of claim 17.

* * * * *

SEQUENCE LISTING

```
<160> NUMBER OF SEQ ID NOS: 11

<210> SEQ ID NO 1
<211> LENGTH: 1494
<212> TYPE: DNA
<213> ORGANISM: Bacillus amyloliquefaciens

<400> SEQUENCE: 1
ggtctactaa aatattattc catactatac aattaataca cagaataatc tgtctattgg      60
ttattctgca aatgaaaaaa aggagaggat aaagagtgag aggcaaaaaa gtatggatca     120
gtttgctgtt tgctttagcg ttaatcttta cgatggcgtt cggcagcaca tcctctgccc     180
aggcggcagg gaaatcaaac ggggaaaaga aatatattgt cgggtttaaa cagacaatga     240
gcacgatgag cgccgctaag aagaaagatg tcatttctga aaaaggcggg aaagtgcaaa     300
agcaattcaa atatgtagac gcagcttcag ctacattaaa cgaaaaagct gtaaaagaat     360
tgaaaaaaga cccgagcgtc gcttacgttg aagaagatca cgtagcacat gcgtacgcgc     420
agtccgtgcc ttacggcgta tcacaaatta aagcccctgc tctgcactct caaggctaca     480
ctggatcaaa tgttaaagta gcggttatcg acagcggtat cgattcttct catcctgatt     540
taaaggtagc aggcggagcc agcatggttc cttctgaaac aaatccttc caagacaaca     600 actctcacgg aactcacgtt gccggcacag ttgcggctct taataactca atcggtgtat     660
taggcgttgc gccaagcgca tcactttacg ctgtaaaagt tctcggtgct gacggttccg     720
gccaatacag ctggatcatt aacggaatcg agtgggcgat cgcaaacaat atggacgtta     780
ttaacatgag cctcggcgga ccttctggtt ctgctgcttt aaaagcggca gttgataaag     840
ccgttgcatc cggcgtcgta gtcgttgcgg cagccggtaa cgaaggcact tccggcagct     900
caagcacagt gggctaccct ggtaaatacc cttctgtcat tgcagtaggc gctgttgaca     960
gcagcaacca aagagcatct ttctcaagcg taggacctga gcttgatgtc atggcacctg    1020
gcgtatctat ccaaagcacg cttcctggaa acaaatacgg ggcgtacaac ggtacgtcaa    1080
```

```
tggcatctcc gcacgttgcc ggagcggctg ctttgattct ttctaagcac ccgaactgga    1140
caaacactca agtccgcagc agtttagaaa acaccactac aaaacttggt gattctttct    1200
actatggaaa agggctgatc aacgtacagg cggcagctca gtaaaacata aaaaaccggc    1260
cttggccccg ccggtttttt attttcttc ctccgcatgt tcaatccgct ccataatcga    1320
cggatggctc cctctgaaaa ttttaacgag aaacggcggg ttgacccggc tcagtcccgt    1380
aacggccaag tcctgaaacg tctcaatcgc cgcttcccgg tttccggtca gctcaatgcc    1440
gtaacggtcg gcggcgtttt cctgataccg ggagacggca ttcgtaatcg gatc          1494
```

<210> SEQ ID NO 2
<211> LENGTH: 382
<212> TYPE: PRT
<213> ORGANISM: Bacillus amyloliquefaciens

<400> SEQUENCE: 2

```
Met Arg Gly Lys Lys Val Trp Ile Ser Leu Leu Phe Ala Leu Ala Leu
  1               5                  10                  15

Ile Phe Thr Met Ala Phe Gly Ser Thr Ser Ser Ala Gln Ala Ala Gly
             20                  25                  30

Lys Ser Asn Gly Glu Lys Lys Tyr Ile Val Gly Phe Lys Gln Thr Met
         35                  40                  45

Ser Thr Met Ser Ala Ala Lys Lys Lys Asp Val Ile Ser Glu Lys Gly
     50                  55                  60

Gly Lys Val Gln Lys Gln Phe Lys Tyr Val Asp Ala Ala Ser Ala Thr
 65                  70                  75                  80

Leu Asn Glu Lys Ala Val Lys Glu Leu Lys Lys Asp Pro Ser Val Ala
                 85                  90                  95

Tyr Val Glu Glu Asp His Val Ala His Ala Tyr Ala Gln Ser Val Pro
            100                 105                 110

Tyr Gly Val Ser Gln Ile Lys Ala Pro Ala Leu His Ser Gln Gly Tyr
        115                 120                 125

Thr Gly Ser Asn Val Lys Val Ala Val Ile Asp Ser Gly Ile Asp Ser
    130                 135                 140

Ser His Pro Asp Leu Lys Val Ala Gly Gly Ala Ser Met Val Pro Ser
145                 150                 155                 160

Glu Thr Asn Pro Phe Gln Asp Asn Asn Ser His Gly Thr His Val Ala
                165                 170                 175

Gly Thr Val Ala Ala Leu Asn Asn Ser Ile Gly Val Leu Gly Val Ala
            180                 185                 190

Pro Ser Ala Ser Leu Tyr Ala Val Lys Val Leu Gly Ala Asp Gly Ser
        195                 200                 205

Gly Gln Tyr Ser Trp Ile Ile Asn Gly Ile Glu Trp Ala Ile Ala Asn
    210                 215                 220

Asn Met Asp Val Ile Asn Met Ser Leu Gly Gly Pro Ser Gly Ser Ala
225                 230                 235                 240

Ala Leu Lys Ala Ala Val Asp Lys Ala Val Ala Ser Gly Val Val Val
                245                 250                 255

Val Ala Ala Ala Gly Asn Glu Gly Thr Ser Gly Ser Ser Ser Thr Val
            260                 265                 270

Gly Tyr Pro Gly Lys Tyr Pro Ser Val Ile Ala Val Gly Ala Val Asp
        275                 280                 285

Ser Ser Asn Gln Arg Ala Ser Phe Ser Ser Val Gly Pro Glu Leu Asp
    290                 295                 300
```

```
Val Met Ala Pro Gly Val Ser Ile Gln Ser Thr Leu Pro Gly Asn Lys
305                 310                 315                 320

Tyr Gly Ala Tyr Asn Gly Thr Ser Met Ala Ser Pro His Val Ala Gly
                325                 330                 335

Ala Ala Ala Leu Ile Leu Ser Lys His Pro Asn Trp Thr Asn Thr Gln
            340                 345                 350

Val Arg Ser Ser Leu Glu Asn Thr Thr Thr Lys Leu Gly Asp Ser Phe
        355                 360                 365

Tyr Tyr Gly Lys Gly Leu Ile Asn Val Gln Ala Ala Gln
370                 375                 380

<210> SEQ ID NO 3
<211> LENGTH: 274
<212> TYPE: PRT
<213> ORGANISM: Artificial Sequence
<220> FEATURE:
<223> OTHER INFORMATION: precursor protease P1

<400> SEQUENCE: 3

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Leu Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Gln
```

```
<210> SEQ ID NO 4
<211> LENGTH: 15
<212> TYPE: PRT
<213> ORGANISM: Artificial Sequence
<220> FEATURE:
<223> OTHER INFORMATION: constructed peptide epitope

<400> SEQUENCE: 4

Asn Val Lys Val Ala Val Ile Asp Ser Gly Ile Asp Ser Ser His
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: constructed peptide epitope

<400> SEQUENCE: 5

Ala Ser Leu Tyr Ala Val Lys Val Leu Gly Ala Asp Gly Ser Gly
 1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: constructed peptide epitope

<400> SEQUENCE: 6

Gly Asn Glu Gly Thr Ser Gly Ser Ser Ser Thr Val Gly Tyr Pro
 1               5                  10                  15

<210> SEQ ID NO 7
<211> LENGTH: 15
<212> TYPE: PRT
<213> ORGANISM: Artificial Sequence
<220> FEATURE:
<223> OTHER INFORMATION: constructed peptide epitope

<400> SEQUENCE: 7

Gly Ser Ser Ser Thr Val Gly Tyr Pro Gly Lys Tyr Pro Ser Val
 1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: constructed peptide epitope

<400> SEQUENCE: 8

Ser Thr Val Gly Tyr Pro Gly Lys Tyr Pro Ser Val Ile Ala Val
 1               5                  10                  15

<210> SEQ ID NO 9
<211> LENGTH: 15
<212> TYPE: PRT
<213> ORGANISM: Artificial Sequence
<220> FEATURE:
<223> OTHER INFORMATION: constructed peptide epitope

<400> SEQUENCE: 9

Asp Ser Ser Asn Gln Arg Ala Ser Phe Ser Ser Val Gly Pro Glu
 1               5                  10                  15

<210> SEQ ID NO 10
```

```
-continued

<211> LENGTH: 15
<212> TYPE: PRT
<213> ORGANISM: Artificial Sequence
<220> FEATURE:
<223> OTHER INFORMATION: synthetic modified peptide

<400> SEQUENCE: 10

Asn Gly Lys Val Ala Val Ile Asp Ser Gly Ile Asp Ser Ser His
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: synthetic modified peptide

<400> SEQUENCE: 11

Asn Ala Lys Val Ala Val Ile Asp Ser Gly Ile Asp Ser Ser His
1               5                   10                  15
```